United States Patent [19]

Mookherjee et al.

[11] Patent Number: 4,865,853
[45] Date of Patent: Sep. 12, 1989

[54] FLAVORING WITH SCHIFF BASE REACTION PRODUCTS OF ALDEHYDES AND ALKYL ANTHRANILATES

[75] Inventors: Braja D. Mookherjee, Holmdel; Robert W. Trenkle, Point Pleasant, both of N.J.; Nicholas Calderone, Laurel Hollow, N.Y.; Keith P. Sands, Marlboro; Myrna L. Hagedorn, Edison, both of N.J.

[73] Assignee: International Flavors & Fragrances Inc., New York, N.Y.

[21] Appl. No.: 323,951

[22] Filed: Mar. 15, 1989

Related U.S. Application Data

[62] Division of Ser. No. 202,046, Jun. 3, 1988, Pat. No. 4,840,801, which is a division of Ser. No. 114,247, Oct. 29, 1987, Pat. No. 4,775,720.

[51] Int. Cl.$^4$ .................. A23G 3/30; A23L 1/226
[52] U.S. Cl. ............................... 426/3; 426/538
[58] Field of Search ............................ 426/3, 538

[56] References Cited

PUBLICATIONS

Arctander, Perfume and Flavor Chemicals, vol. II, 1969, published by the author: Montclair, N.J., Monograph No. 1910.

*Primary Examiner*—Joseph Golian
*Attorney, Agent, or Firm*—Arthur L. Liberman

[57] ABSTRACT

Described are schiff base reaction products of alkyl anthanilates having the structure:

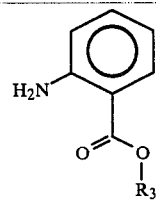

wherein $R_3$ represents methyl or ethyl and aldehydes of the generic structure:

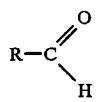

wherein R represents unsaturated hydrocarbyl and alkoxy hydrocarbyl moieties or mixtures of aldehydes having the structures:

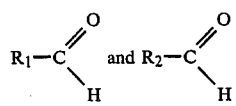

wherein $R_1$ and $R_2$ are different alkoxy hydrocarbyl moieties and hydrocarbyl moieties including the aldehydes:
(a) bergamal having the structure:

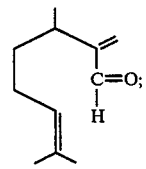

(b) floralozone having the structure:

(Abstract continued on next page.)

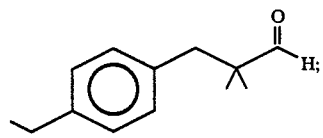

(c) pino acetaldehyde having the structure:

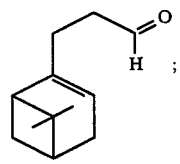

(d) pino isobutyraldehyde having the structure:

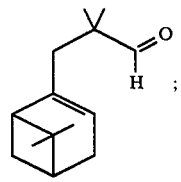

(e) melonal having the structure:

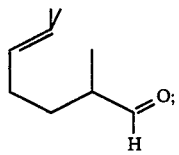

and
(f) canthoxal having the structure:

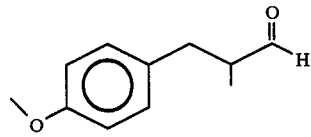

and organoleptic uses thereof in augmenting or enhancing the aroma or taste of consumable materials including perfume compositions, colognes, perfumed articles, foodstuffs, chewing gums and beverages.

1 Claim, 25 Drawing Sheets

GLC PROFILE FOR EXAMPLE I.

NMR SPECTRUM FOR EXAMPLE I.

GLC PROFILE FOR EXAMPLE I.

FIG. 4 NMR SPECTRUM FOR EXAMPLE II.

GLC PROFILE FOR EXAMPLE III.

NMR SPECTRUM FOR EXAMPLE III.

FIG. 7 NMR SPECTRUM FOR EXAMPLE III.

GLC PROFILE FOR EXAMPLE IV.

GLC PROFILE FOR EXAMPLE V.

FIG. 10 NMR SPECTRUM FOR EXAMPLE V.

NMR SPECTRUM FOR EXAMPLE V.

GLC PROFILE FOR EXAMPLE VI

GLC PROFILE FOR EXAMPLE VI.

NMR SPECTRUM FOR PEAK 1303 OF FIG.13 OF EXAMPLE VI.

NMR SPECTRUM FOR PEAK 1301 OF FIG. 13 OF EXAMPLE VI.

FIG. 16 NMR SPECTRUM FOR PEAK 1302 OF FIG. 13 OF EXAMPLE VI.

GLC PROFILE FOR EXAMPLE VII.

FIG. 18 NMR SPECTRUM FOR EXAMPLE VII.

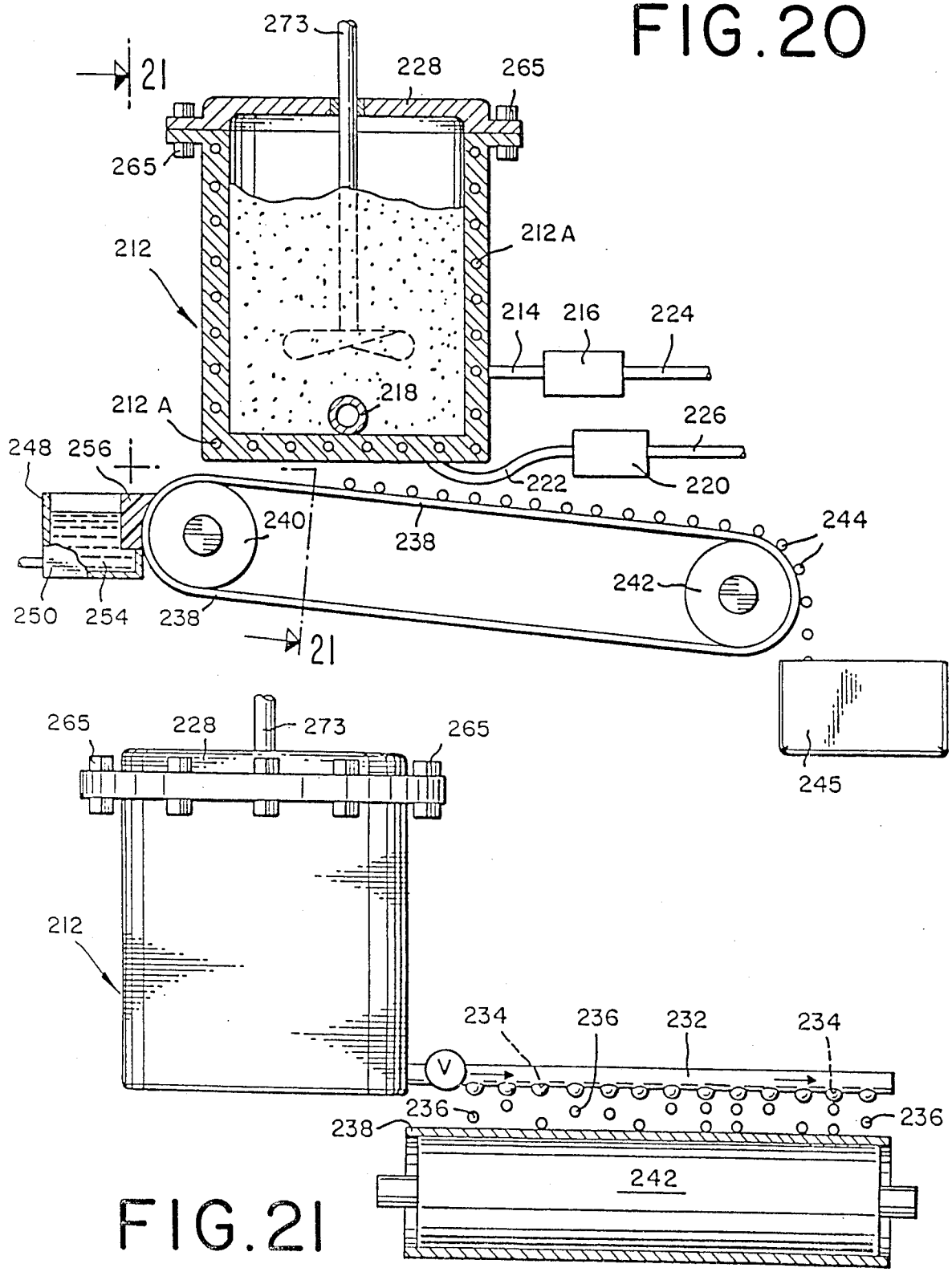

GLC PROFILE FOR EXAMPLE VIII
CRUDE

GLC PROFILE FOR EXAMPLE VIII DISTILLATE

FIG. 24 NMR SPECTRUM FOR EXAMPLE VIII

GLC PROFILE FOR EXAMPLE IX.
CRUDE

2501

NMR SPECTRUM FOR EXAMPLE IX.

FLAVORING WITH SCHIFF BASE REACTION PRODUCTS OF ALDEHYDES AND ALKYL ANTHRANILATES

This is a divisional of application Ser. No. 202,046, filed 6/3/88, now U.S. Pat. No. 4,840,801 which in turn, is a streamline divisional application of application for U.S. Ser. No. 114,247 filed on Oct. 29, 1987, now U.S. Pat. No. 4,775,720 issued on Oct. 4, 1988.

BACKGROUND OF THE INVENTION

Our invention relates to novel reaction products which are schiff bases of aldehydes and alkyl anthranilates and organoleptic uses thereof in augmenting or enhancing the aroma or taste of perfume compositions, colognes, perfumed articles, foodstuffs, chewing gums and beverages.

Inexpensive chemical compositions of matter which can provide lemony, floral, green, ozoney, fruity, melony, citrus, piney, grape-like, woody, sweet and muguet aromas with anisic, fresh cut wood, ozoney, fresh air, floral and orange flower topnotes and anisic, woody, floral, green and citrus undertones are highly desirable in the art of perfumery. Many of the natural materials which provide such fragrances and contribute desired nuances to perfumery compositions as well as perfumed articles including solid or liquid anionic, cationic, nonionic or zwitterionic detergents, fabric softener compositions and fabric softener articles are high in cost, vary in quality from one batch to another and/or are generally subject to the usual variations of natural products.

By the same token, materials which can provide intense grape-like aromas and tastes are highly useful and are well known in the art of flavoring for foodstuffs, toothpastes, chewing gums, medicinal products and chewing tobaccos. Many of the natural materials which provide such flavor nuances and contribute desired nuances to flavoring compositions are high in cost, vary in quality from one batch to another and/or are generally subject to the usual variations of natural products.

There is, accordingly, a continuing effort to find synthetic materials which will replace, enhance or augment the essential flavor and fragrance notes provided by natural essential oils or compositions thereof. Unfortunately, many of the synthetic materials either have the desired nuances only to a relatively small degree or else contribute undesirable or unwanted odor to the compositions. The search for materials which provide, for example, a more refined grape-like flavor or more refined lemon flavor, for example, has been difficult and relatively costly in the areas of both natural products and synthetic products. By the same token, the search for materials which can provide a more refined lemony, floral, green, ozoney, fruity, melony, citrus, piney, grape-like, woody, sweet and muguet aroma, for example, has been difficult and relatively costly in the areas of both natural products and synthetic products.

Artificial flavoring agents for foodstuffs have received increasing attention for many years. For many years such food flavoring agents have been preferred over natural flavoring agents at least in part due to their diminished costs and their reproducible flavor qualities. For example, natural food flavoring agents such as extracts, concentrates and the like are often subject to wide variations due to changes in quality and type and treatment of the raw materials. Such variations can be reflected in the end products and result in unfavorable flavor characteristics in the end product. Additionally, the presence f the natural product in the ultimate food may be undesirable because of increasing tendency to spoil. This is particularly troublesome in food and food uses where such products as dips, soups, chips, sausages, gravies and desserts and the like are apt to be stored prior to use.

Even more desirable are products that can serve to substitute for difficult-to-obtain natural perfumery oils and, at the same time, substitute for natural flavoring ingredients in foodstuffs, chewing gums, medicinal products, toothpastes and chewing tobaccos.

Reaction products of carbonyl-containing compounds and amine-containing compounds are well known in the art of flavoring and in the art of of perfumery. Thus, U.S. Pat. No. 4,618,501 issued on Oct. 21, 1986 discloses the flavoring of foodstuffs with alpha,-beta-keto-amines and states that an alpha,beta-keto-amine having a nutty corn, cereal aroma may be used for flavoring compositions for foods having the structure:

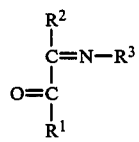

wherein $R_1$, $R_2$ and $R_3$ are selected from the group consisting of a saturated or unsaturated alkyl straight or branched chain hydrocarbons having from 1-3 carbon atoms.

U.S. Pat. No. 3,625,710, issued on Dec. 7, 1971 discloses the use of aldimines as chocolate-like flavors which aldimines are resulting from the reaction product of amines and aldehydes, for example, N-isobutylidenefurfurylamine, N-isopentylidenefurfurylamine, N-isopentylideneisopentylamine.

Schiff bases are also known in the art of perfumery. Thus, for example, Chemical Abstracts Volume 103, 1985, No. 123134z (Abstract of Japan Kokai No. 60/78951 discloses the use in perfumery of compounds having the structure:

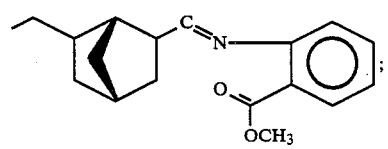

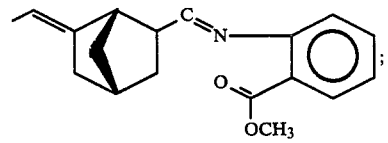

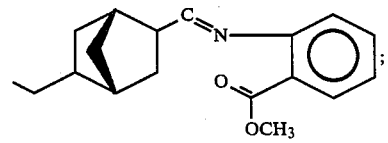

and

-continued

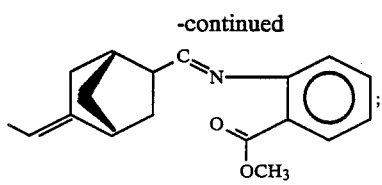

The book "Flavor & Fragrance Materials-1987" published by Allured Publishing Corporation, P.O. Box 318, Wheaton, Ill. 60189-0318 discloses on page 154 the commercial availability of the following schiff bases:
Methyl anthranilate and amyl cinnamic aldehyde;
Methyl anthranilate and hydroxy citronellal;
Methyl anthranilate and lilial;
Methyl anthranilate and anisic aldehyde;
Methyl anthranilate and decanal;
Methyl anthranilate and lyral;
Methyl anthranilate and iso-nonylaldede;
Methyl anthranilate and phenylacetaldehydel
Schiff bases are also known to be useful as intermediates in producing other fragrance materials. Thus, U.S. Pat. No. 3,898,283 issued on Aug. 5, 1975 discloses novel schiff base intermediates used in producing 4 or 5 phenylpentenals having the structure:

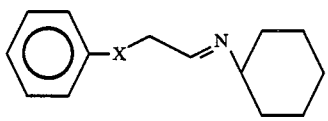

wherein X is a moiety selected from the group consisting of:

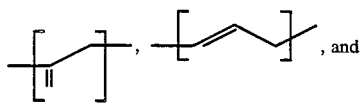

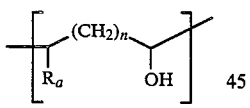

and wherein $R_a$ is hydrogen or methyl.

Nothing in the prior art however discloses the novel reaction products or reaction product mixtures of our invention having unobvious, unexpected and advantageous organoleptic properties.

Indeed, nothing in the prior art is indicative of the novel schiff base reaction products of our invention having deodorizing properties that is, having a deodorant value of 0.50 up to 3.5 as measured by the deodorant value test described in U.S. Pat. No. 4,304,679 incorporated by reference herein or having a Lipoxidase-inhibiting capacity of at least 50% and a Malodour reduction value of from 0.25 up to 3 as measured by the Malodour reduction value test disclosed in U.S. Pat. No. 4,663,063 incorporated by reference herein.

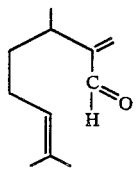

and methyl anthranilate having the structure:

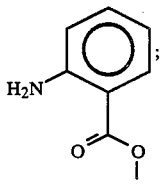

and the reaction products having the structures:

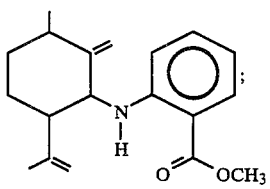

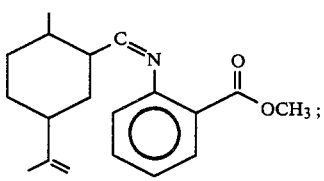

and

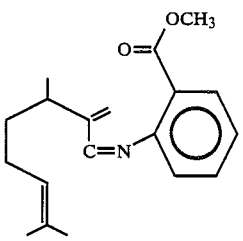

(Conditions: OV-1 fused silica column, 50 m×0.32 mm programmed at 60°-220° C. at 4° C. per minute).

Figure 2:
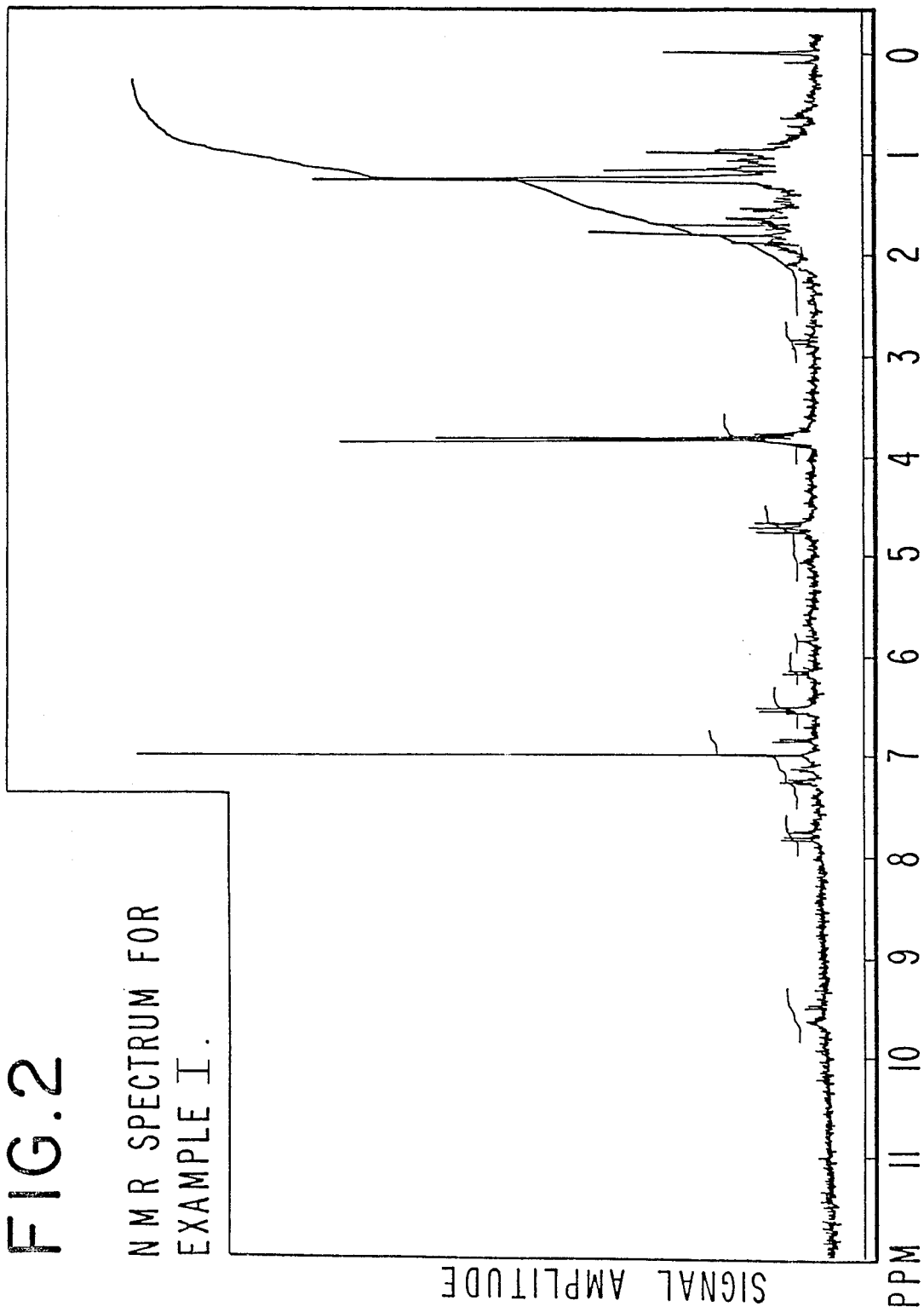

FIG. 2 is the NMR spectrum for the mixture of compounds having the structures:

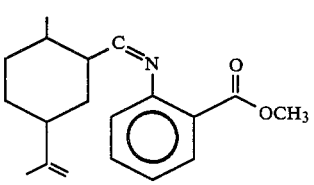

and

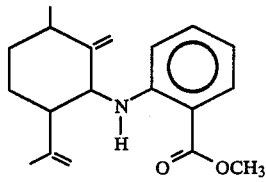

produced according to Example I.

Figure 3:
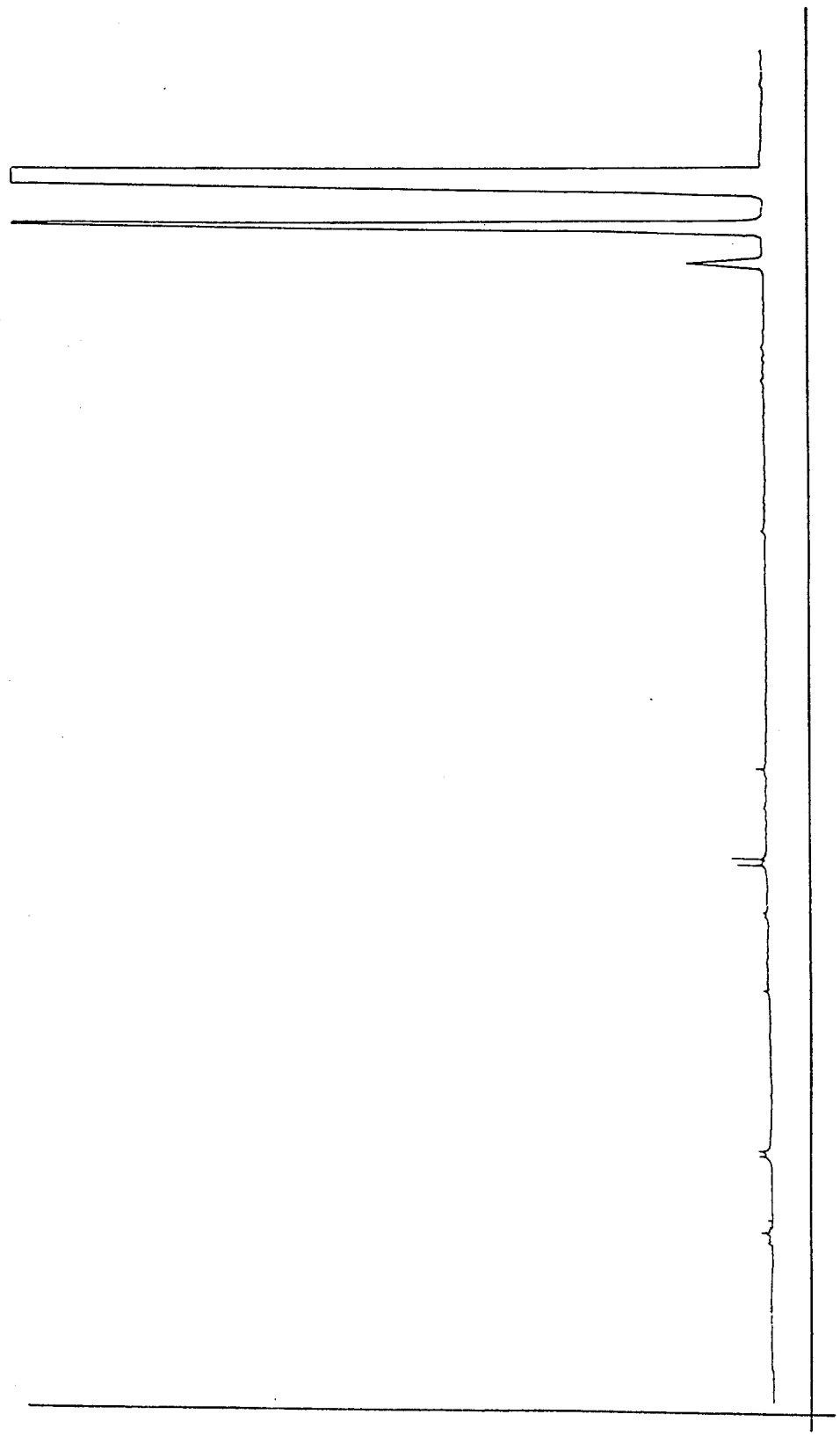

FIG. 3 is the GLC profile for the crude reaction product of Example II containing the compound having the structure.

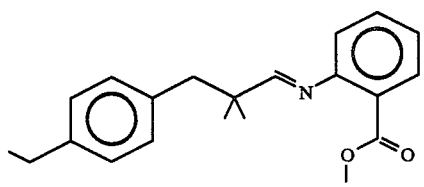

(Conditions: OV-1 fused silica column, 60 m×0.32 mm programmed at 60°–220° C. at 4° C. per minute).

Figure 4:
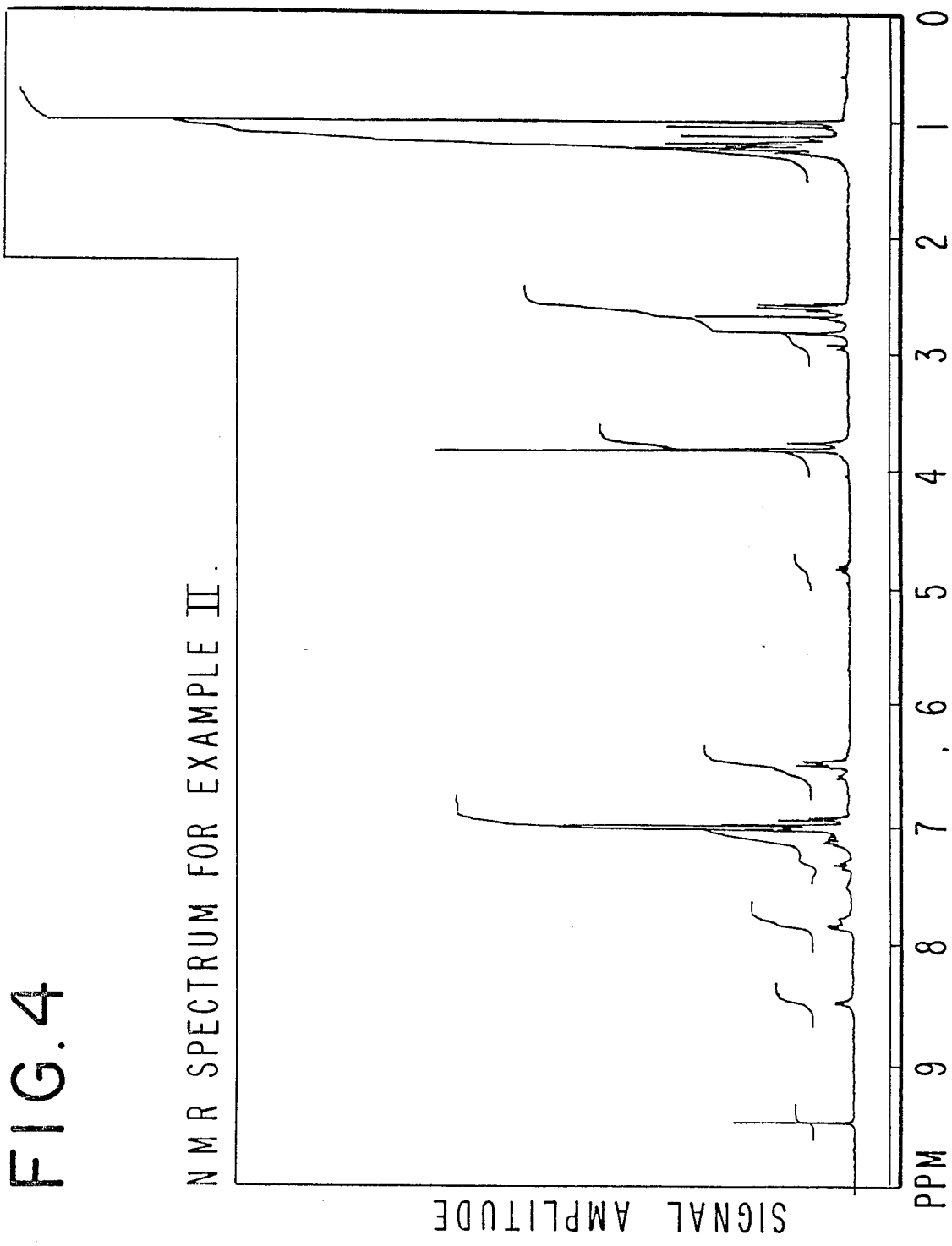

FIG. 4 is the NMR spectrum for the compound having the structure:

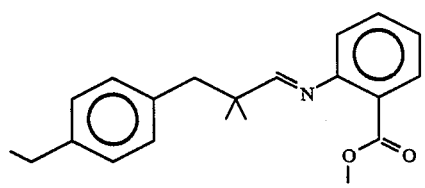

produced according to Example II.

Figure 5:
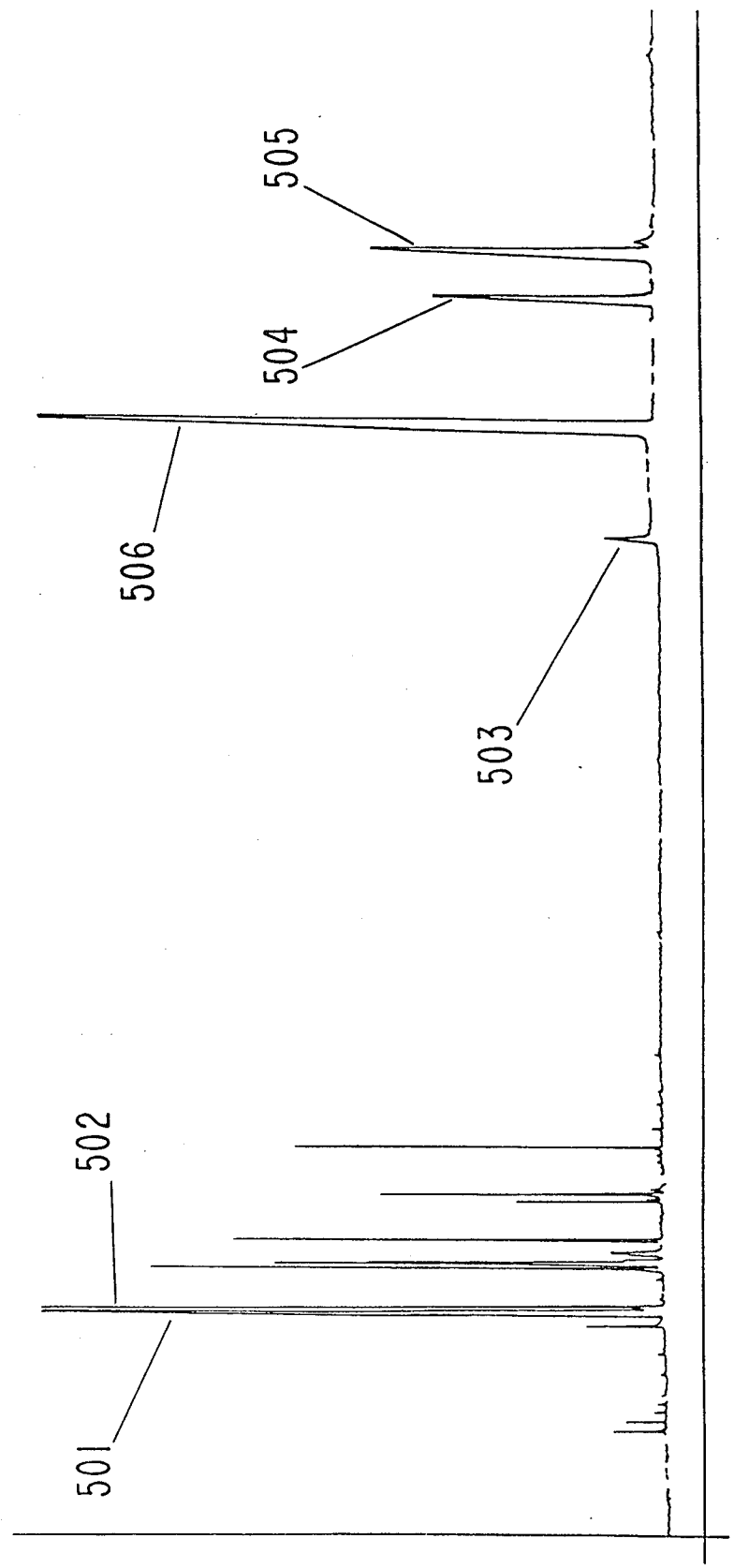

FIG. 5 is the GLC profile for the crude reaction product of Example III produced by reaction of pino acetaldehyde having the structure:

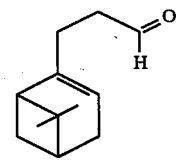

with methyl anthranilate having the structure:

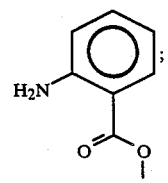

and containing products having the structures:

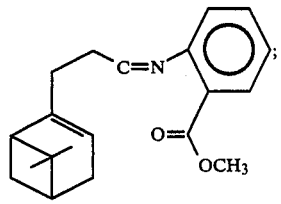

and

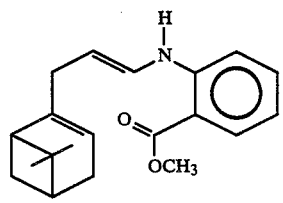

(Conditions: 50 m×0.32 mm OV-1 fused silica column, programmed at 60°–220° C. at 4° C. per minute).

Figure 6:
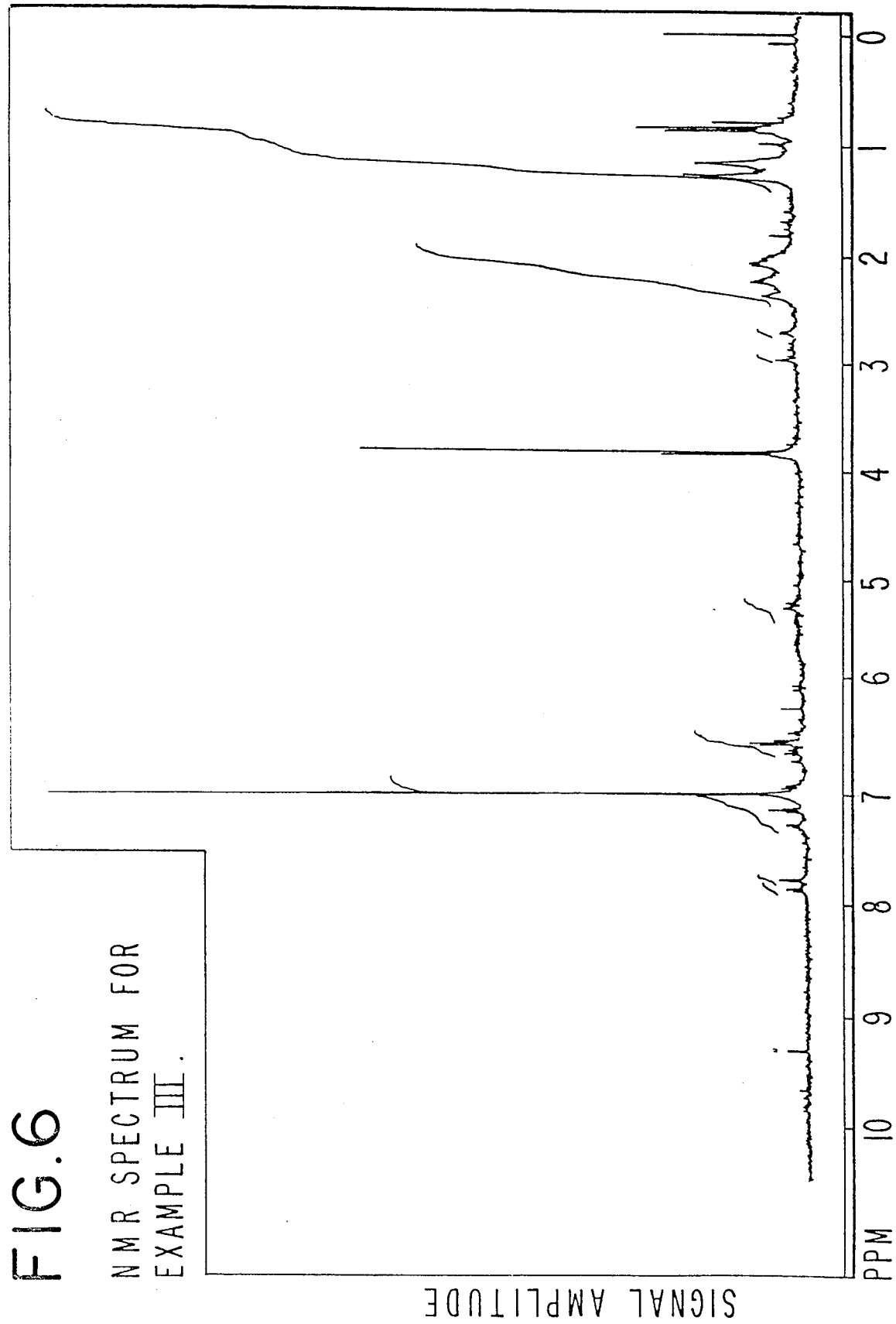

FIG. 6 is the NMR spectrum for the compound having the structure:

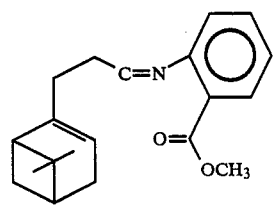

produced according to Example III.

Figure 7:
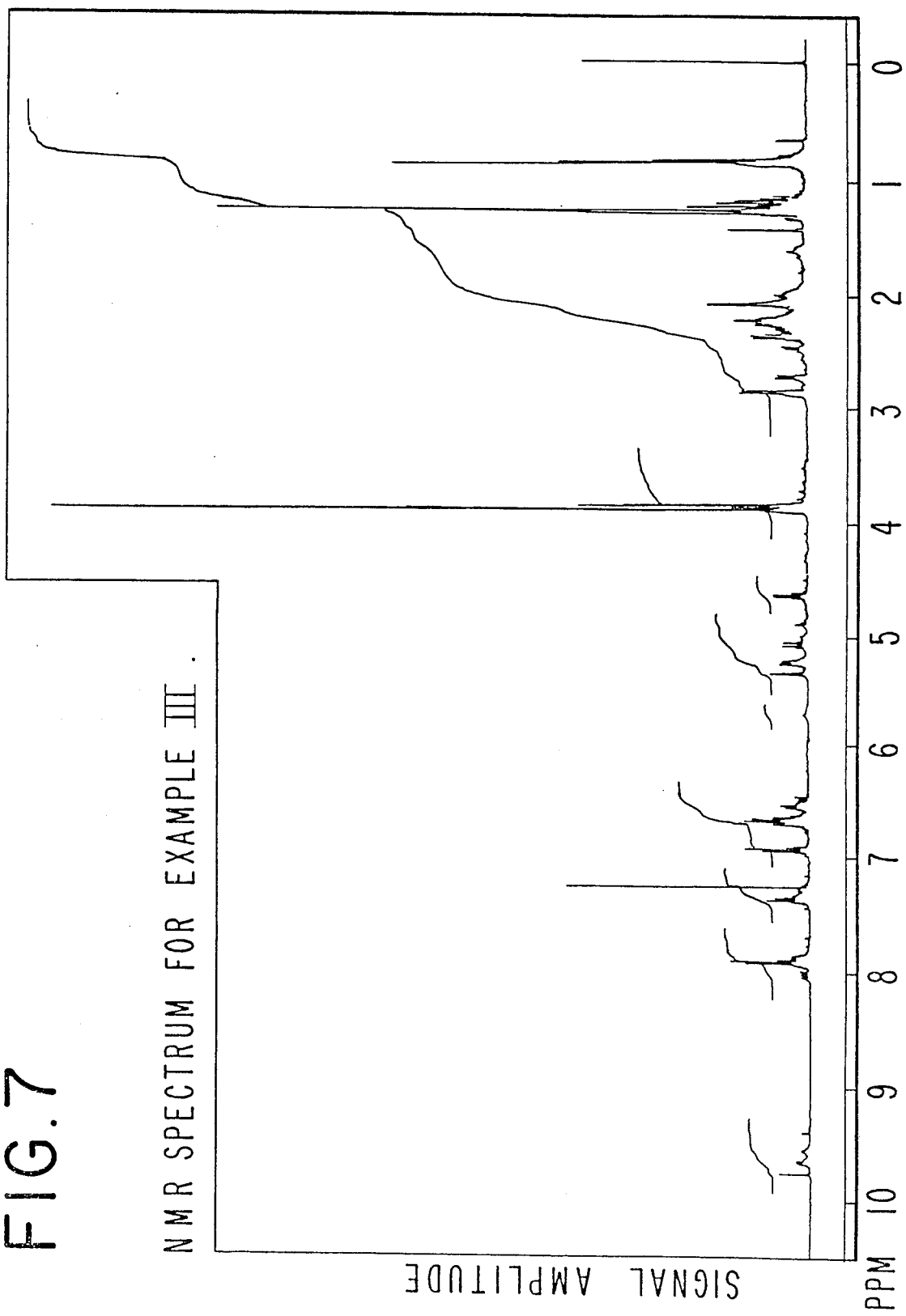

FIG. 7 is the NMR spectrum for the compound having the structure:

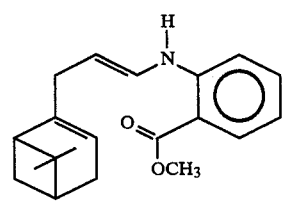

produced according to Example III.

Figure 8:
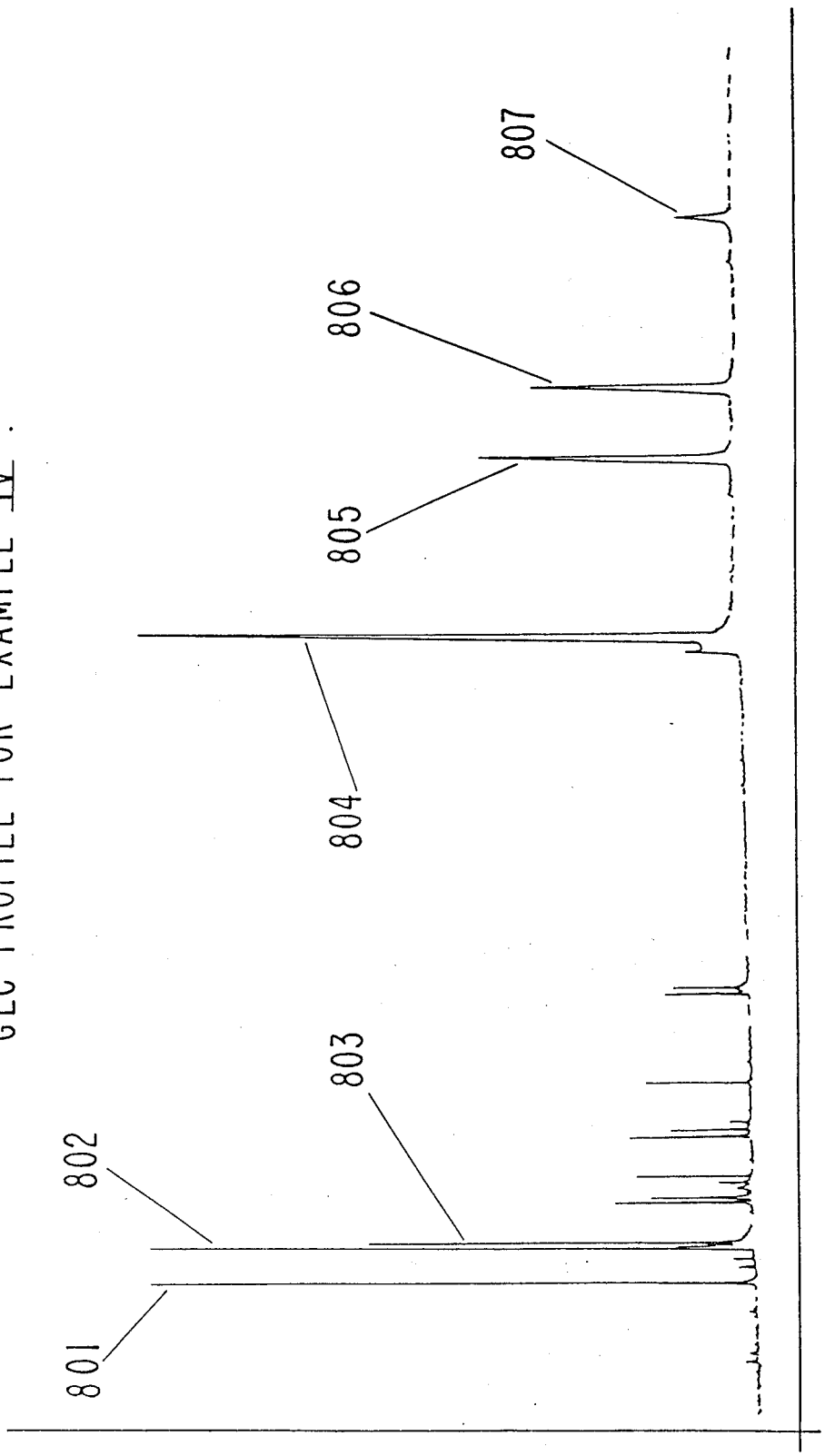

FIG. 8 is the GLC profile for the crude reaction product of Example IV resulting from the schiff base reaction of hydroxy citronellal and pino acetaldehyde with methyl anthranilate and containing the compounds having the structures:

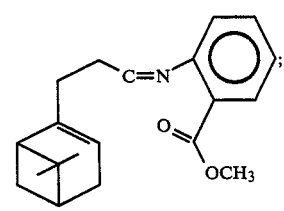

-continued

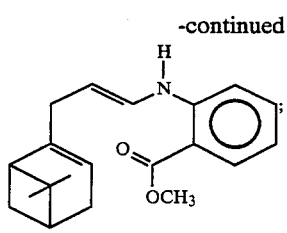

and

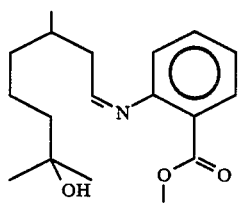

(Conditions: 50 m×0.32 mm OV-1 fused silica column, programmed at 60°-220° C. at 4° C. per minute).

Figure 9:
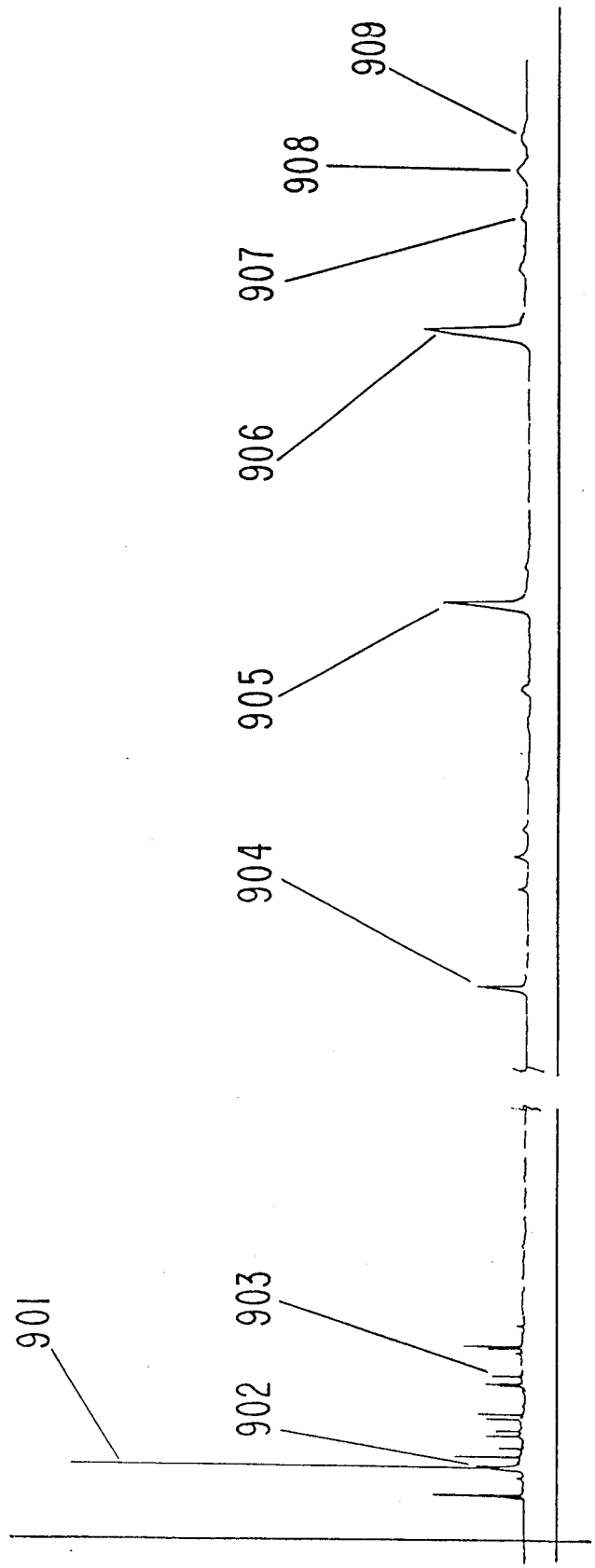

FIG. 9 is the GLC profile for the crude reaction product of Example V containing the schiff base reaction products of pino acetaldehyde and lilial having the structure:

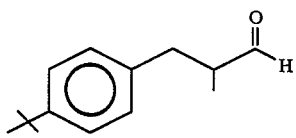

with methyl anthranilate and containing the compounds having the structures:

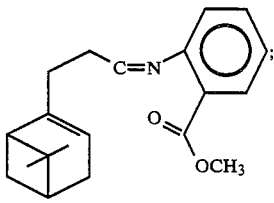

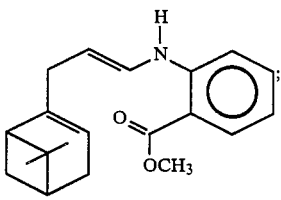

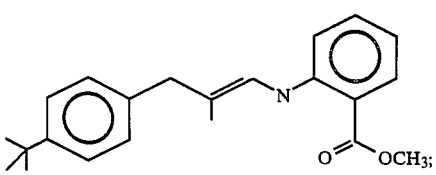

(mixture of E and Z isomers) and the compound having the structure:

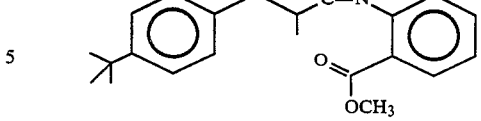

(Conditions: 50 m×0.32 mm OV-1 fused silica column, programmed at 60°-220° C. at 4° C. per minute).

Figure 10:
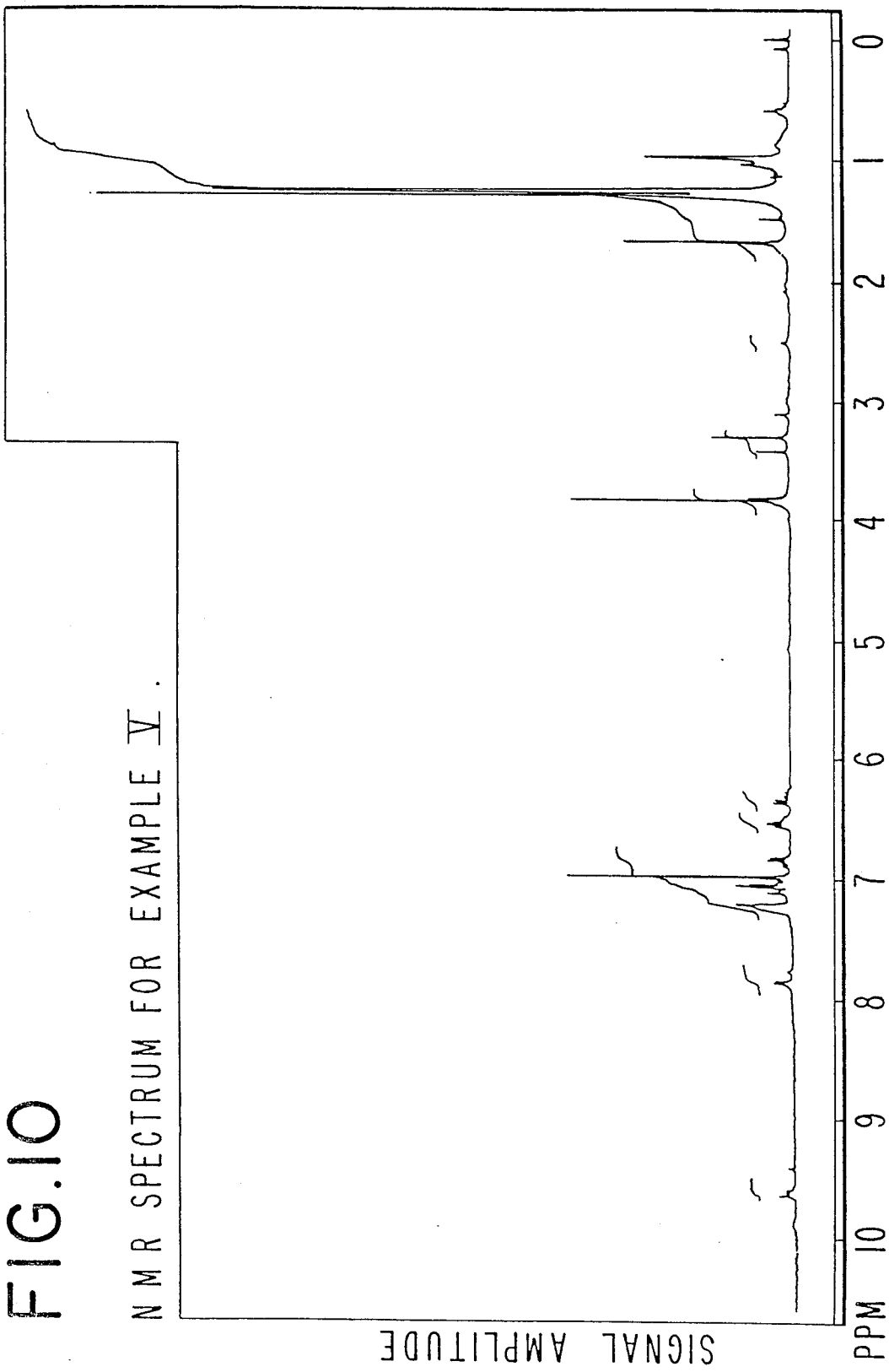

FIG. 10 is the NMR spectrum for the mixture of E and Z isomers having the structure:

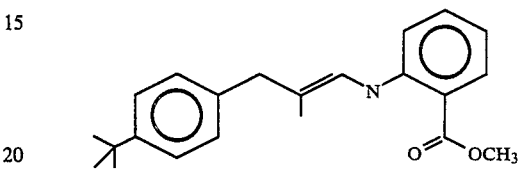

produced according to Example V.

Figure 11:
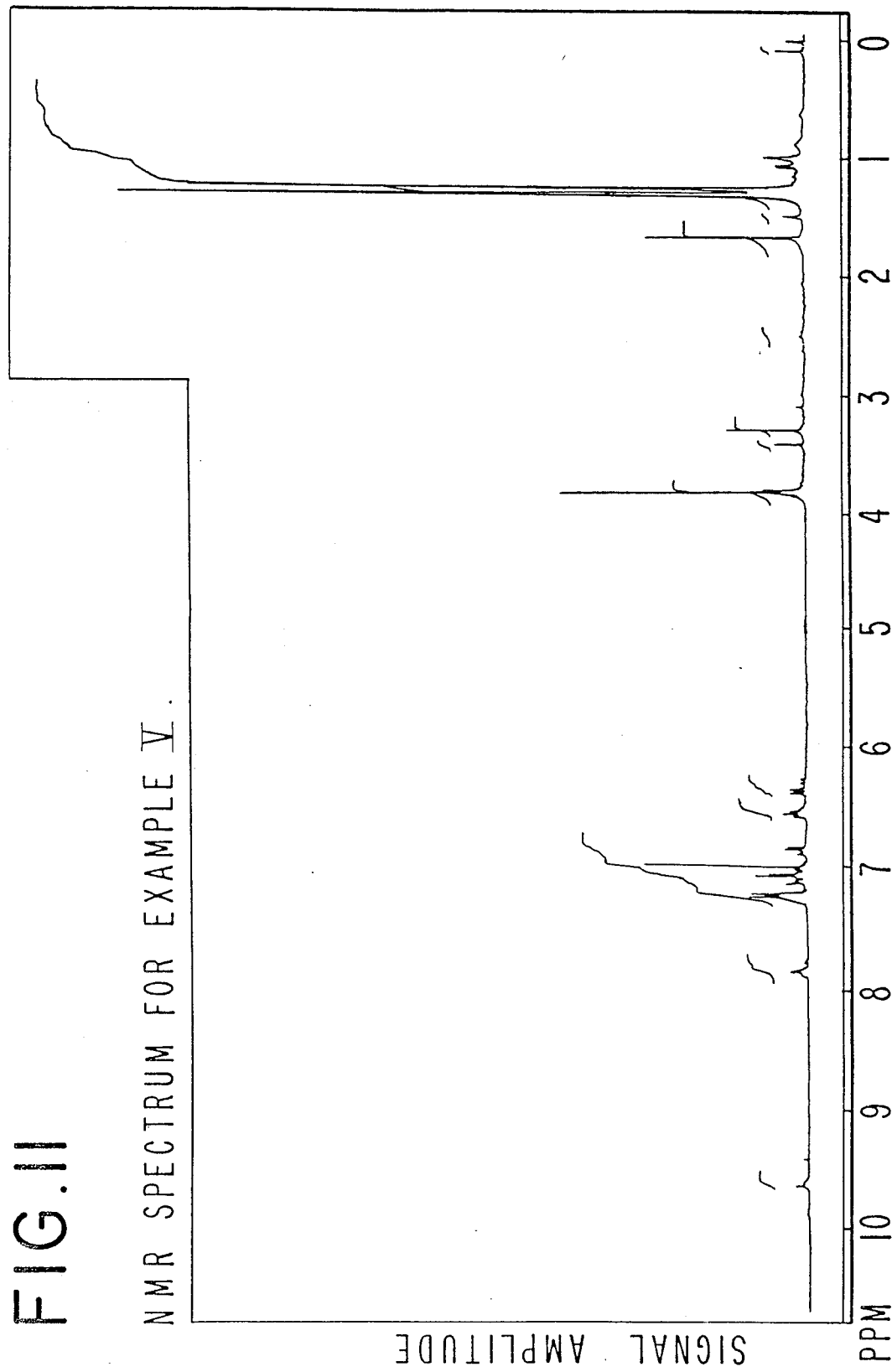

FIG. 11 is a confirmatory NMR spectrum for the compound having the structure:

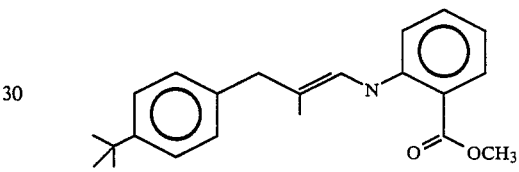

(mixture of E and Z isomers) produced according to Example V.

Figure 12:
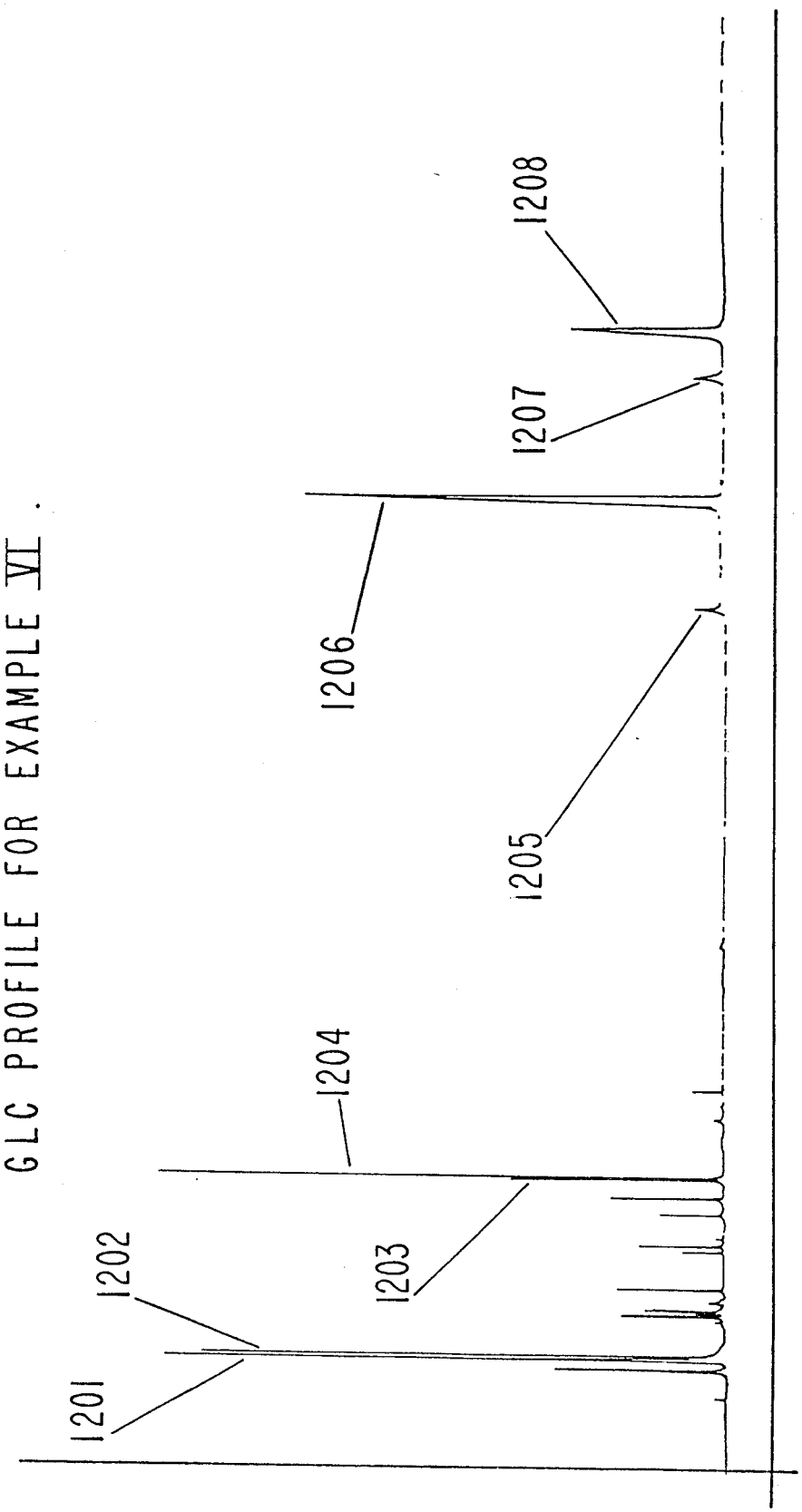

FIG. 12 is the GLC profile for the crude reaction product of Example VI(A), the reaction products of pino acetaldehyde and lyral, the mixture of compounds having the structures:

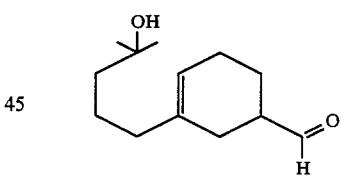

and

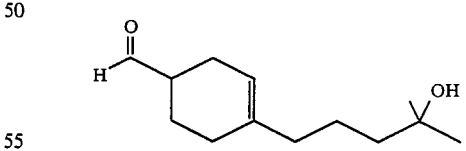

with methyl anthranilate and contains the compounds having the structures:

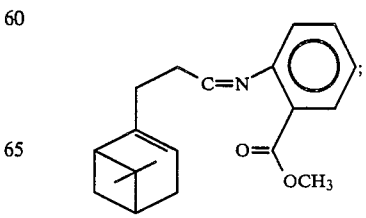

-continued

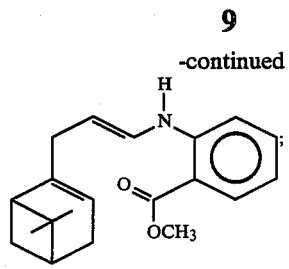

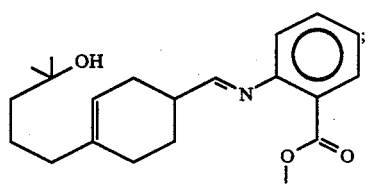

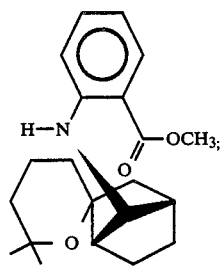

and

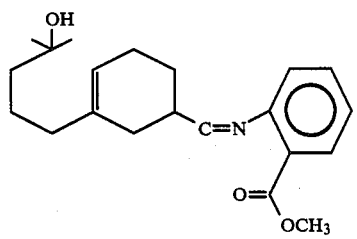

(Conditions: 50 m×0.32 mm OV-1 fused silica column, programmed at 60°–220° C. at 4° C. per minute).

Figure 13:
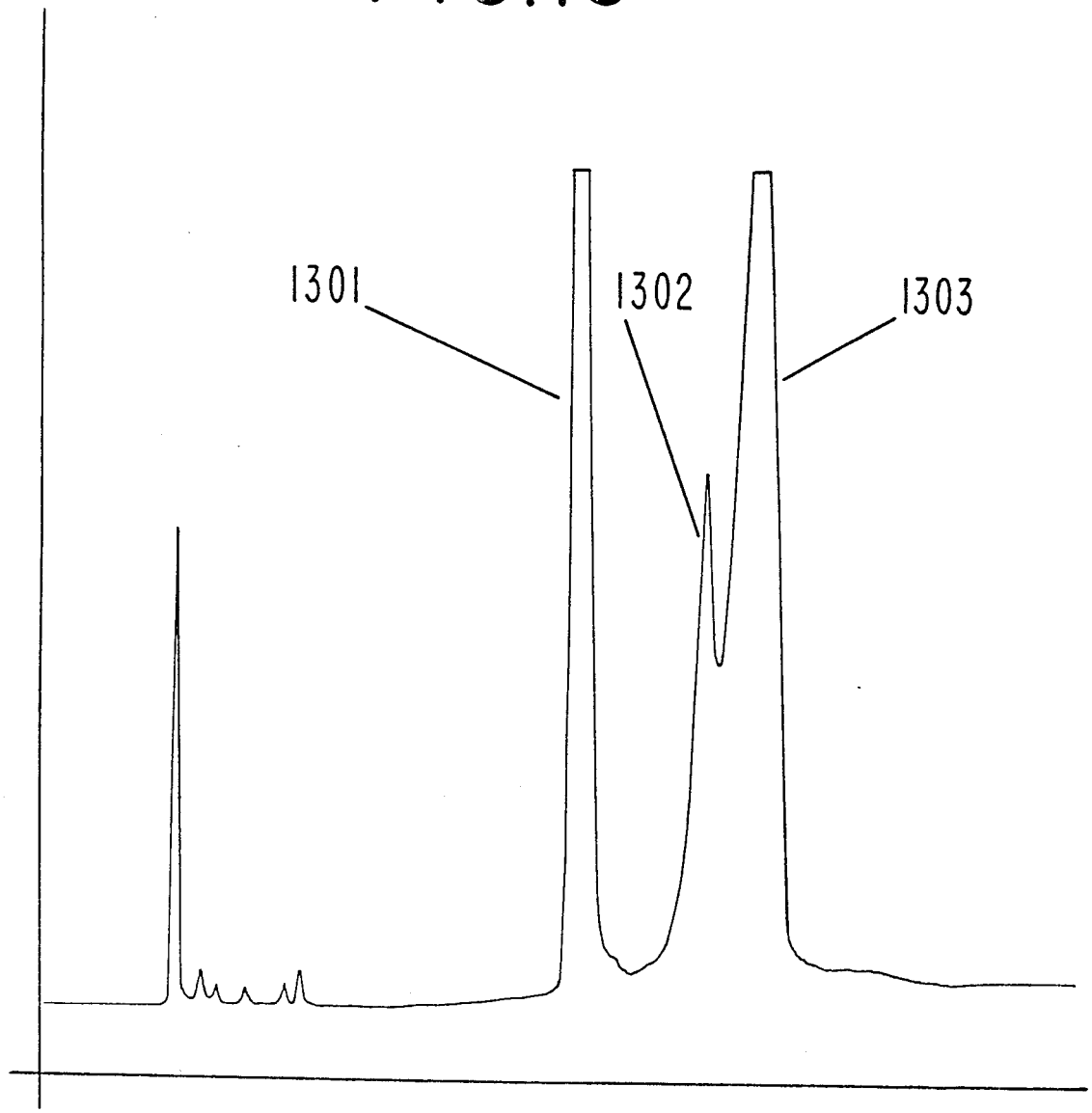

FIG. 13 is the GLC profile for the crude reaction product of Example VI(B), the reaction product of pino acetaldehyde and lyral with methyl anthranilate (with the mole ratio of pino acetaldehyde:lyral:methyl anthranilate being 1:1:2) and containing the compounds having the structures:

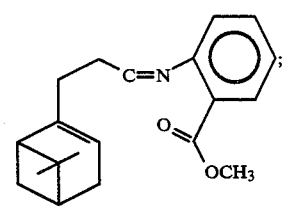

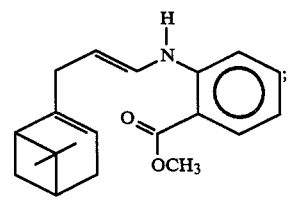

-continued

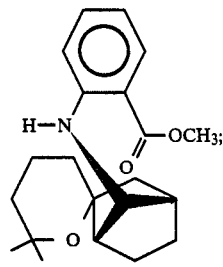

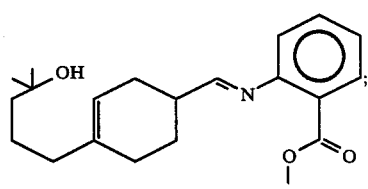

and

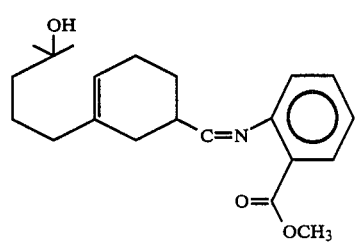

(Conditions: 3'×0.125" 10% SE-30 column programmed at 6° C. per minute).

Figure 14:
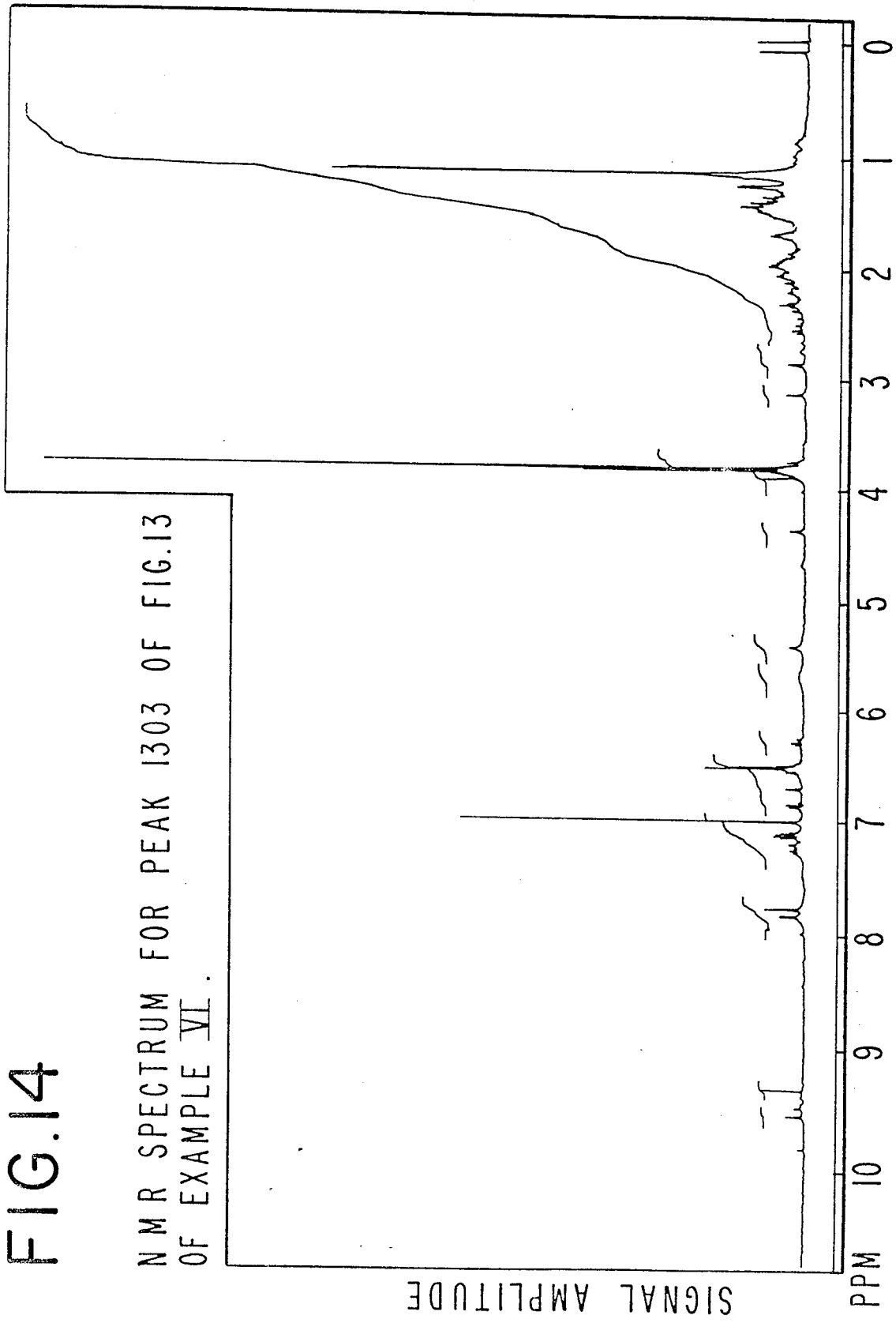

FIG. 14 is the NMR spectrum for the peak indicated by reference numeral 1303 of the GLC profile of FIG. 13 and is for, primarily, the compound having the structure:

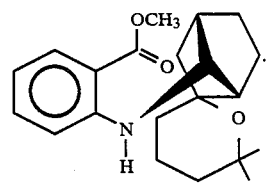

Figure 15:
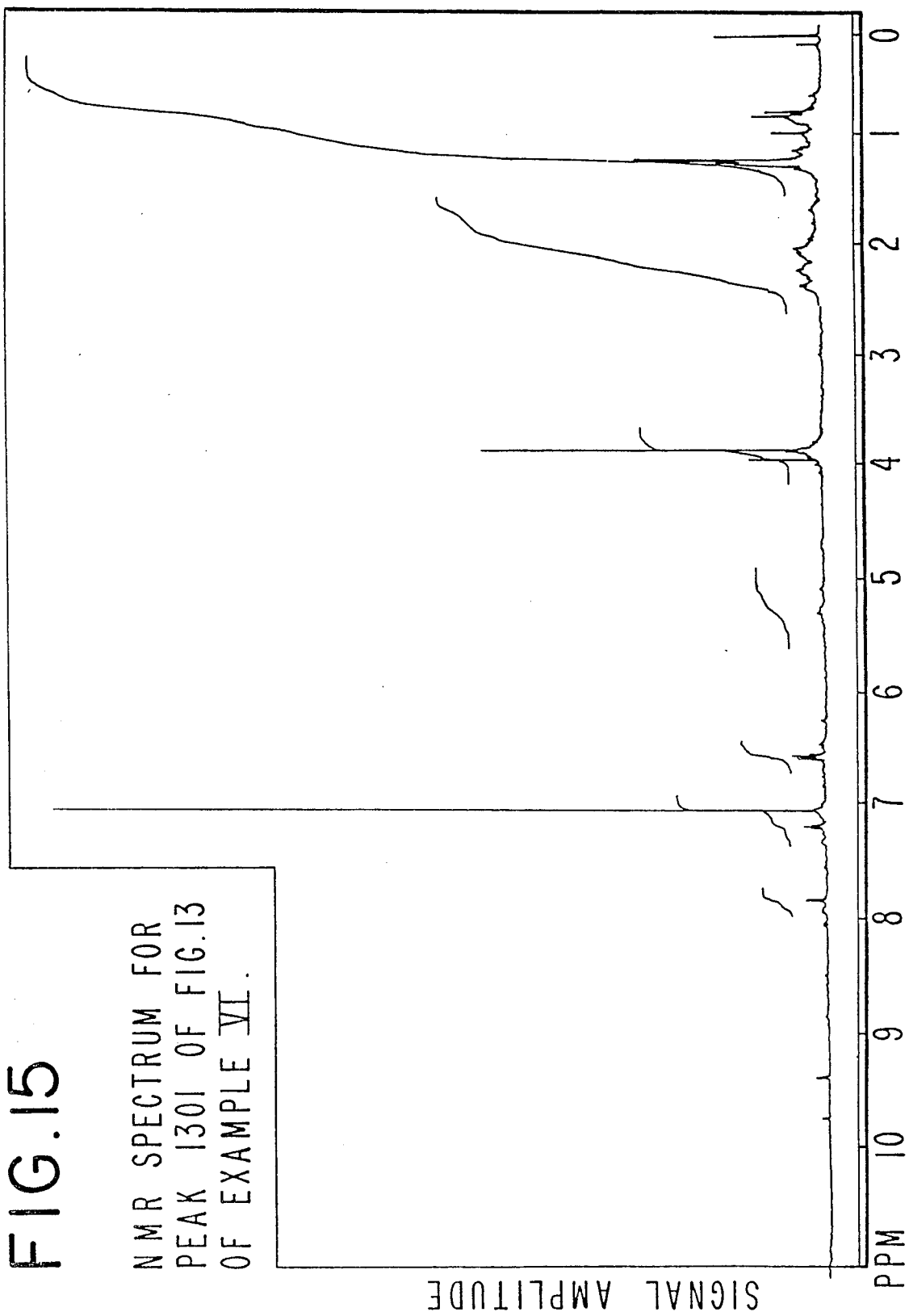

FIG. 15 is the NMR spectrum for the peak indicated by reference numeral 1301 on FIG. 13 and is for a mixture of compounds having the structures:

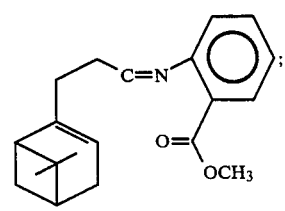

-continued

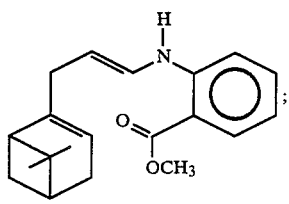

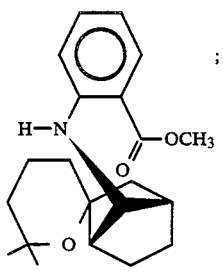

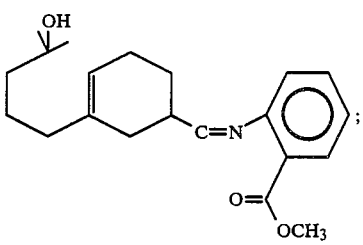

and

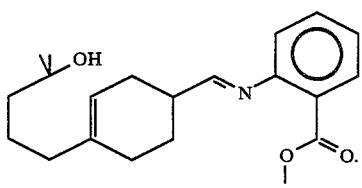

Figure 16:
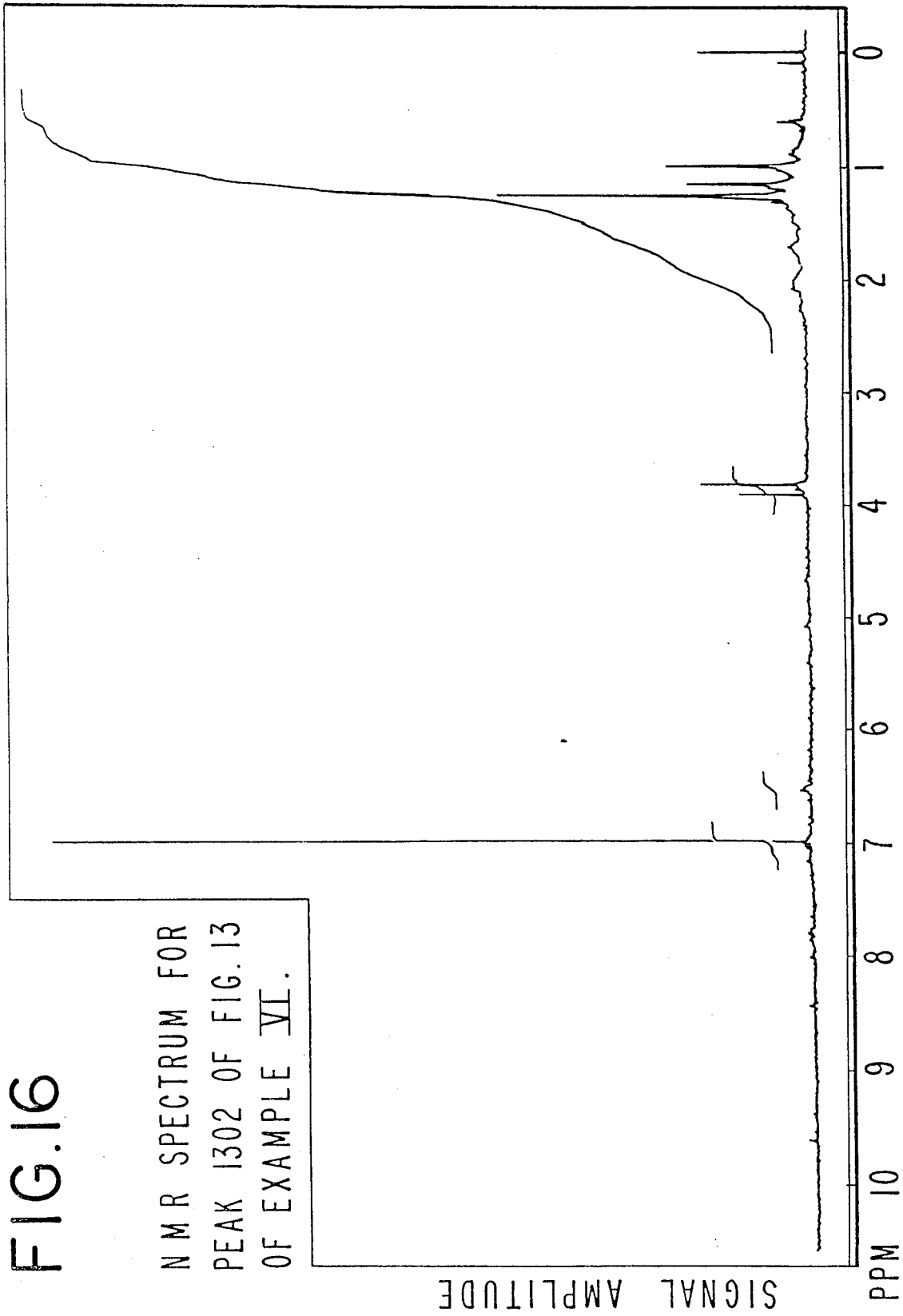

FIG. 16 is the NMR spectrum for the peak indicated by reference numeral 1302 on the GLC profile of FIG. 13 and is also for a mixture of compounds having the structures:

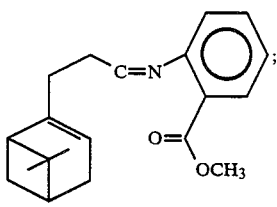

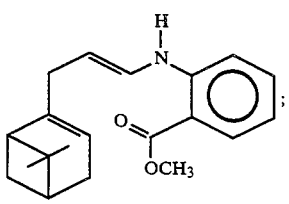

-continued

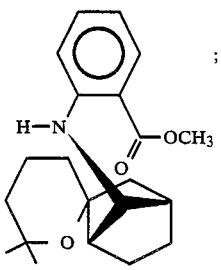

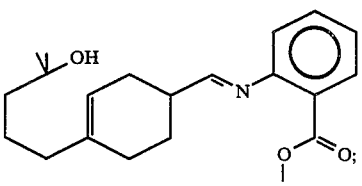

and

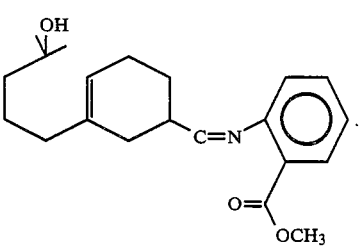

Figure 17:
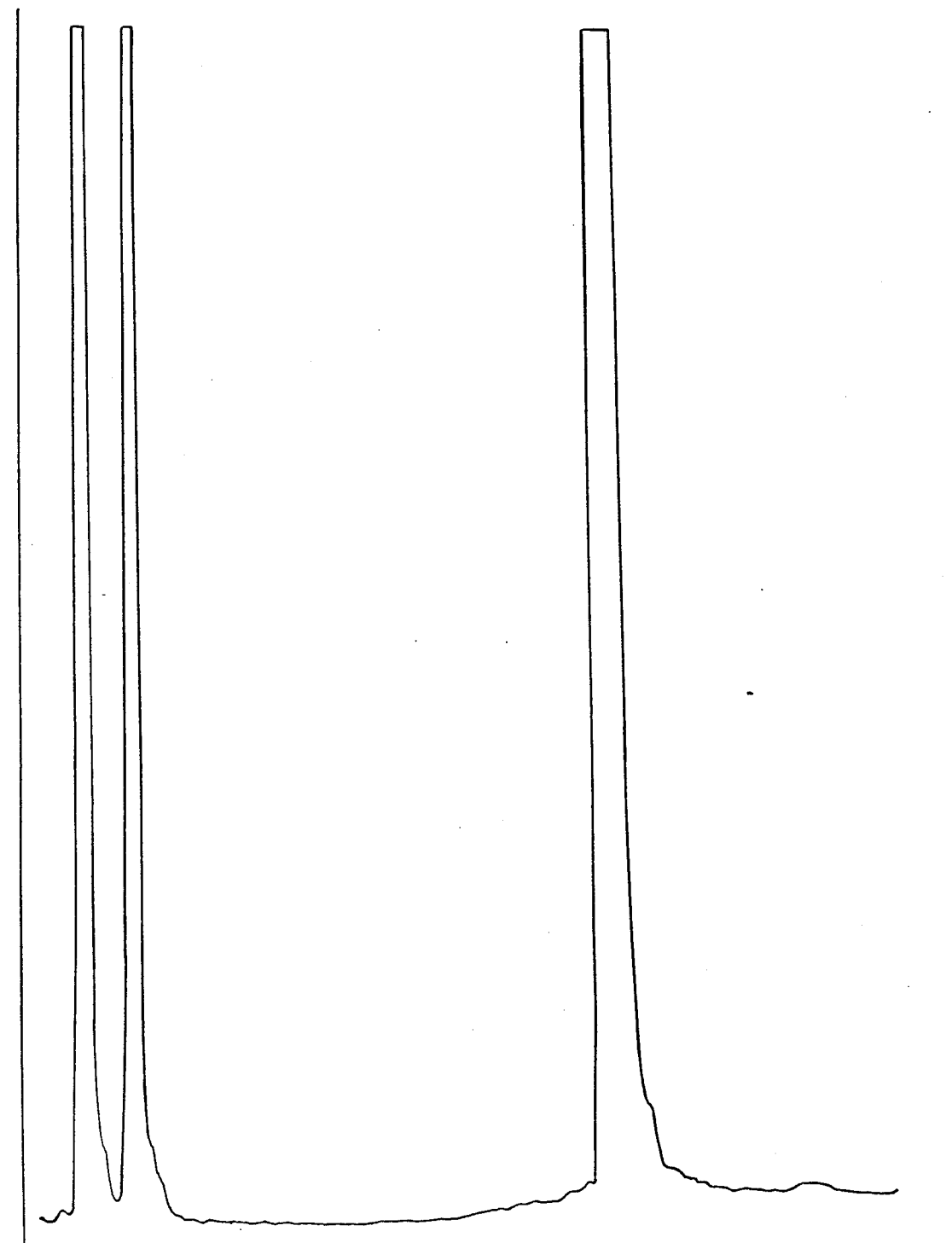

FIG. 17 is the GLC profile for the crude reaction product of Example VII containing the compound having the structure:

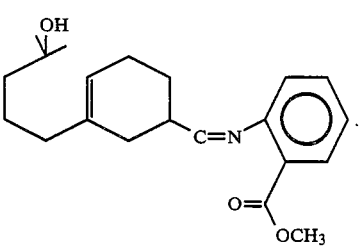

(Conditions: 3'×0.125" 10% SE-30 column).

Figure 18:
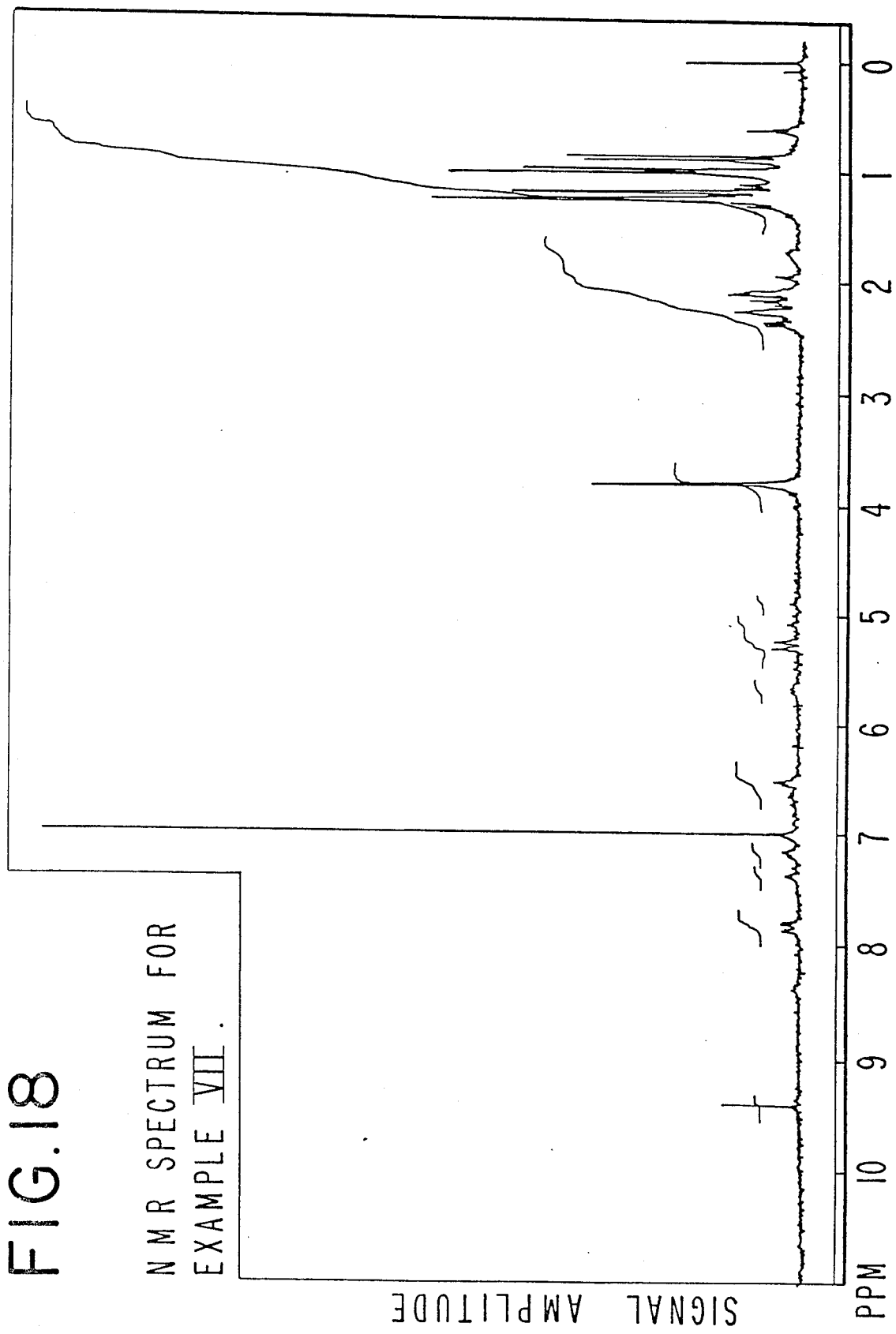

FIG. 18 is the NMR spectrum for the compound having the structure:

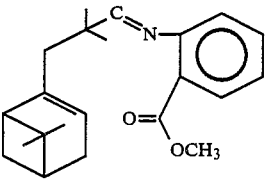

produced according to Example VII.

Figure 19:
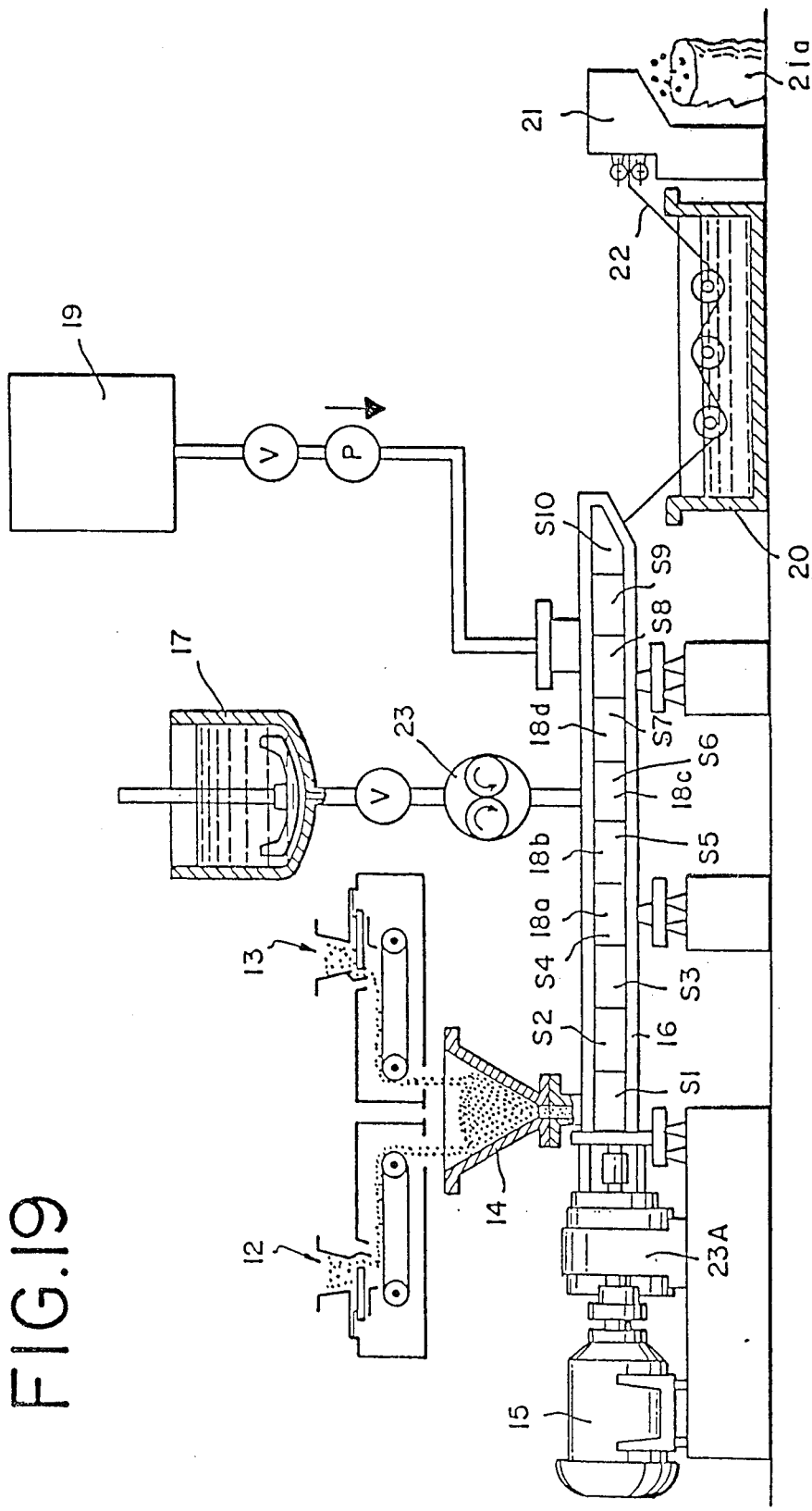

FIG. 19 is a cut-away side elevation schematic diagram of a screw extruder during the compounding of a resin with one of the schiff base compounds of our invention while simultaneously adding foaming agent into the hollow portion of the barrel of the extruder and incorporates the pelletizing apparatus used in pelletizing the extruded foamed tow produced as a result of the extrusion operation.

FIG. 20 represents a cut-away side elevation view of apparatus used in forming perfumed polymers which contain imbedded therein at least one of the schiff base compounds of our invention.

FIG. 21 is a front view of the apparatus of FIG. 20 looking in the direction of the arrows.

Figure 22:
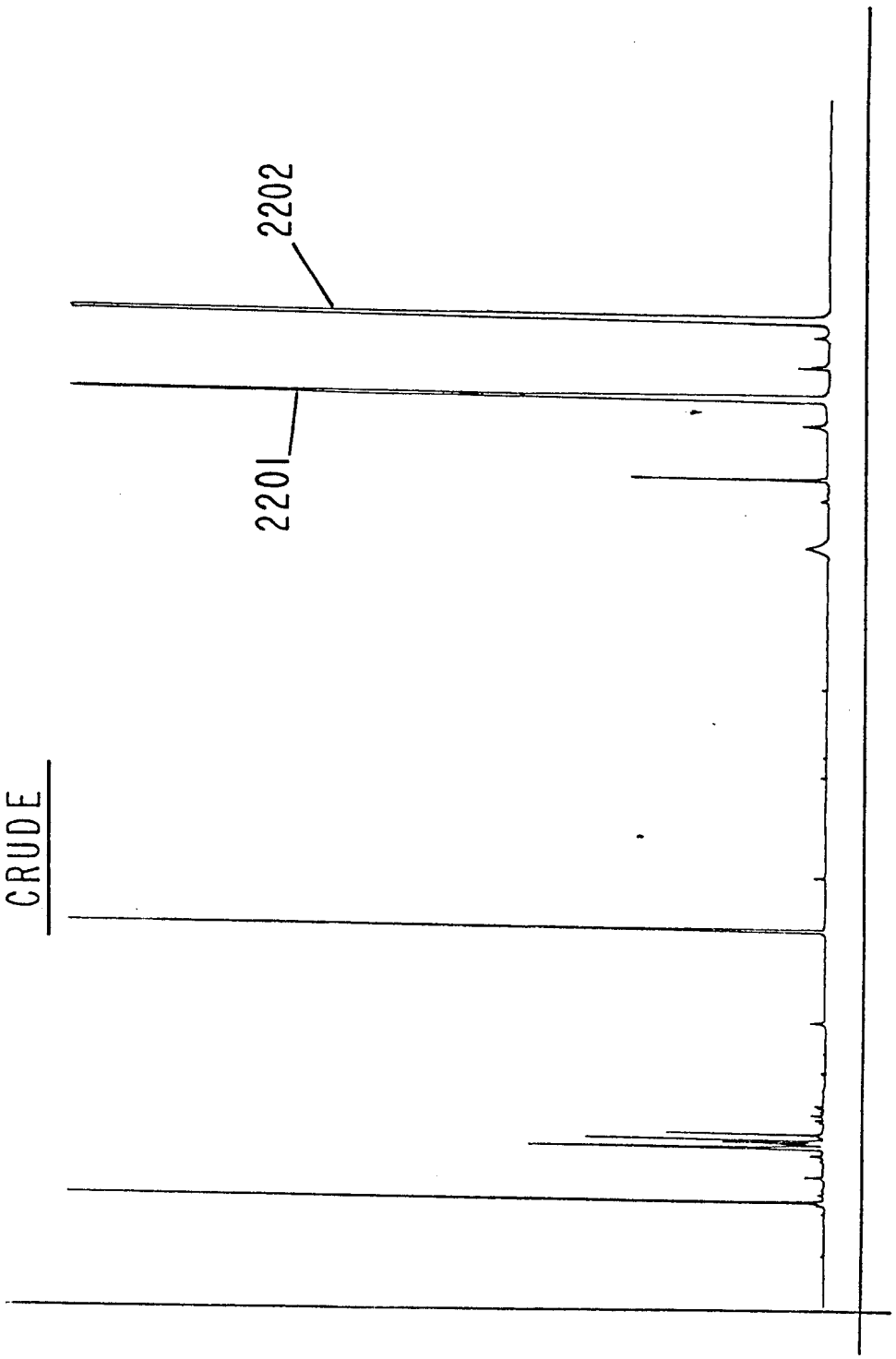

FIG. 22 is the GLC profile for the crude reaction product produced according to Example VIII containing the compound having the structure:

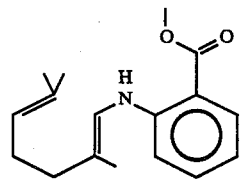

(Conditions: 50 m×0.32 mm OV-1 column, programmed at 60°–220° C. at 4° C. per minute).

Figure 23:
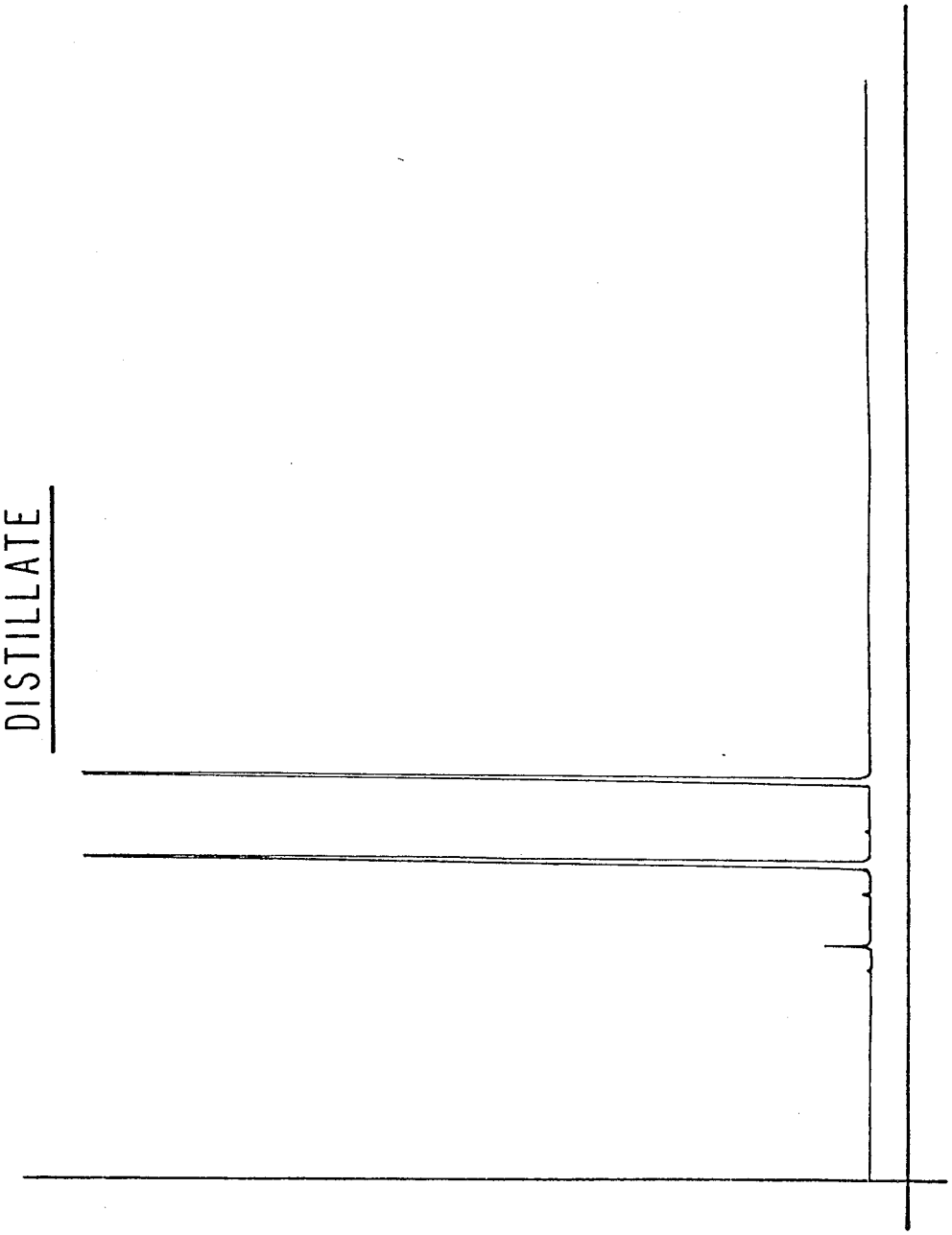

FIG. 23 is the GLC profile for the distillation product of the reaction product of Example VIII containing the compound having the structure:

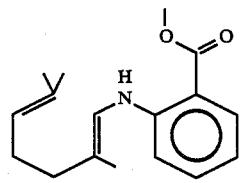

(Conditions: 50 m×0.32 mm OV-1 column, programmed at 60°–220° C. at 4° C. per minute).

Figure 24:
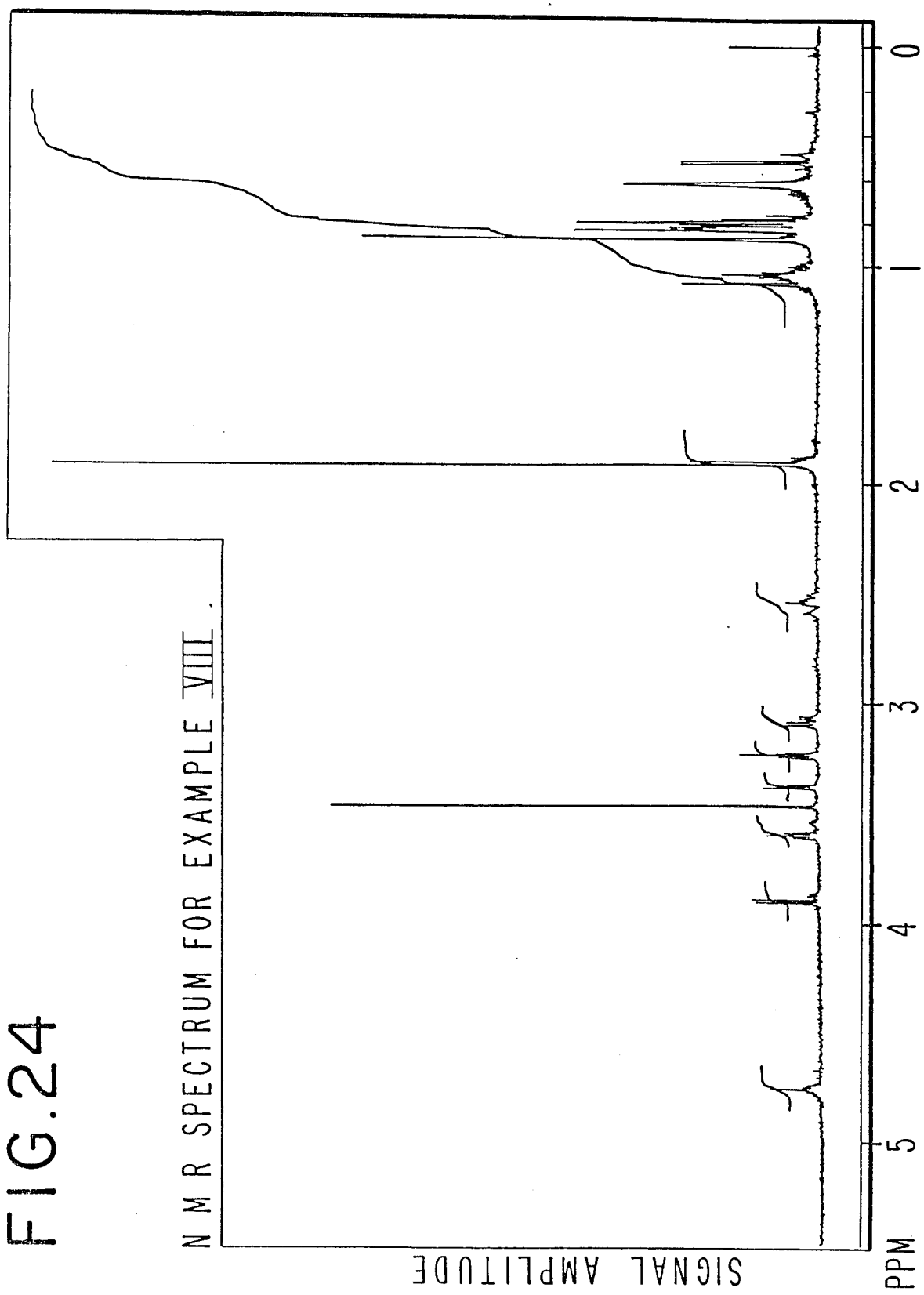

FIG. 24 is the NMR spectrum for the compound having the structure:

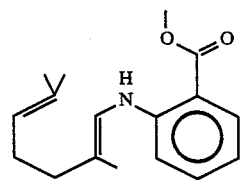

produced according to Example VIII.

Figure 25:
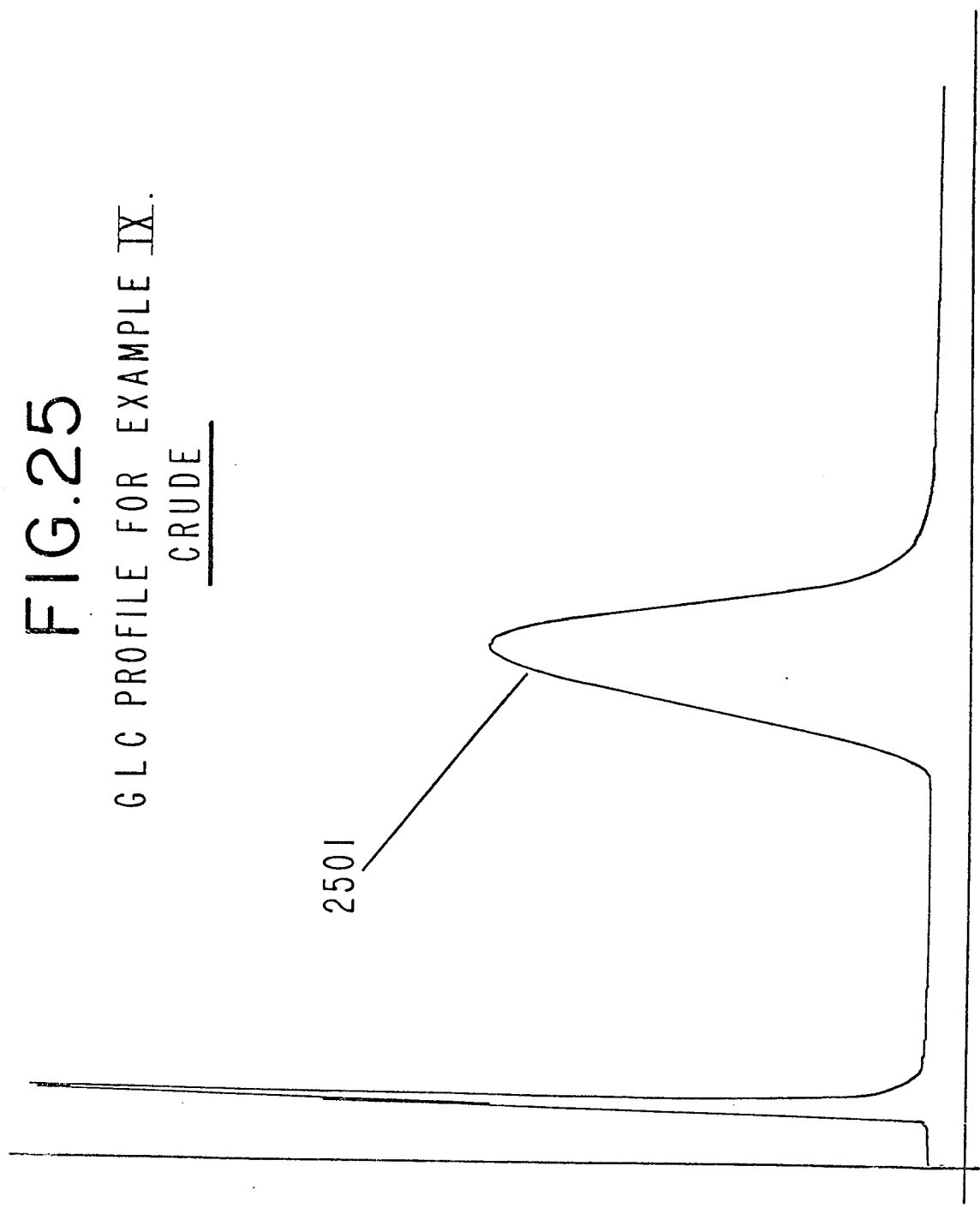

FIG. 25 is the GLC profile for the crude reaction product of Example IX containing the compound having the structure:

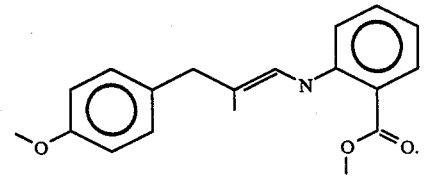

Figure 26:
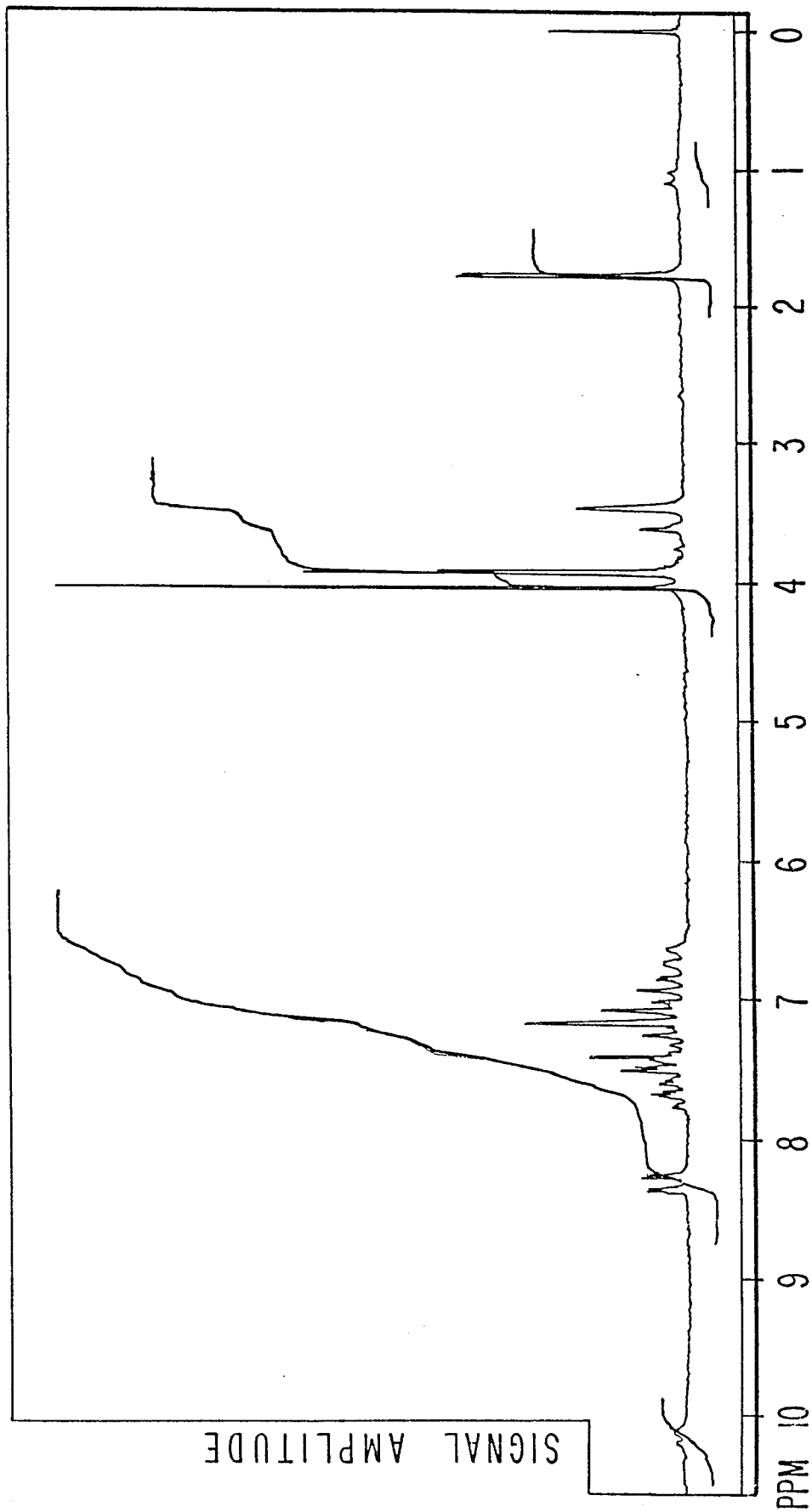

FIG. 26 is the NMR spectrum for the compound having the structure:

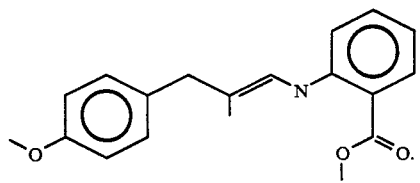

produced according to Example IX.

DETAILED DESCRIPTION OF THE DRAWINGS

Figure 1:
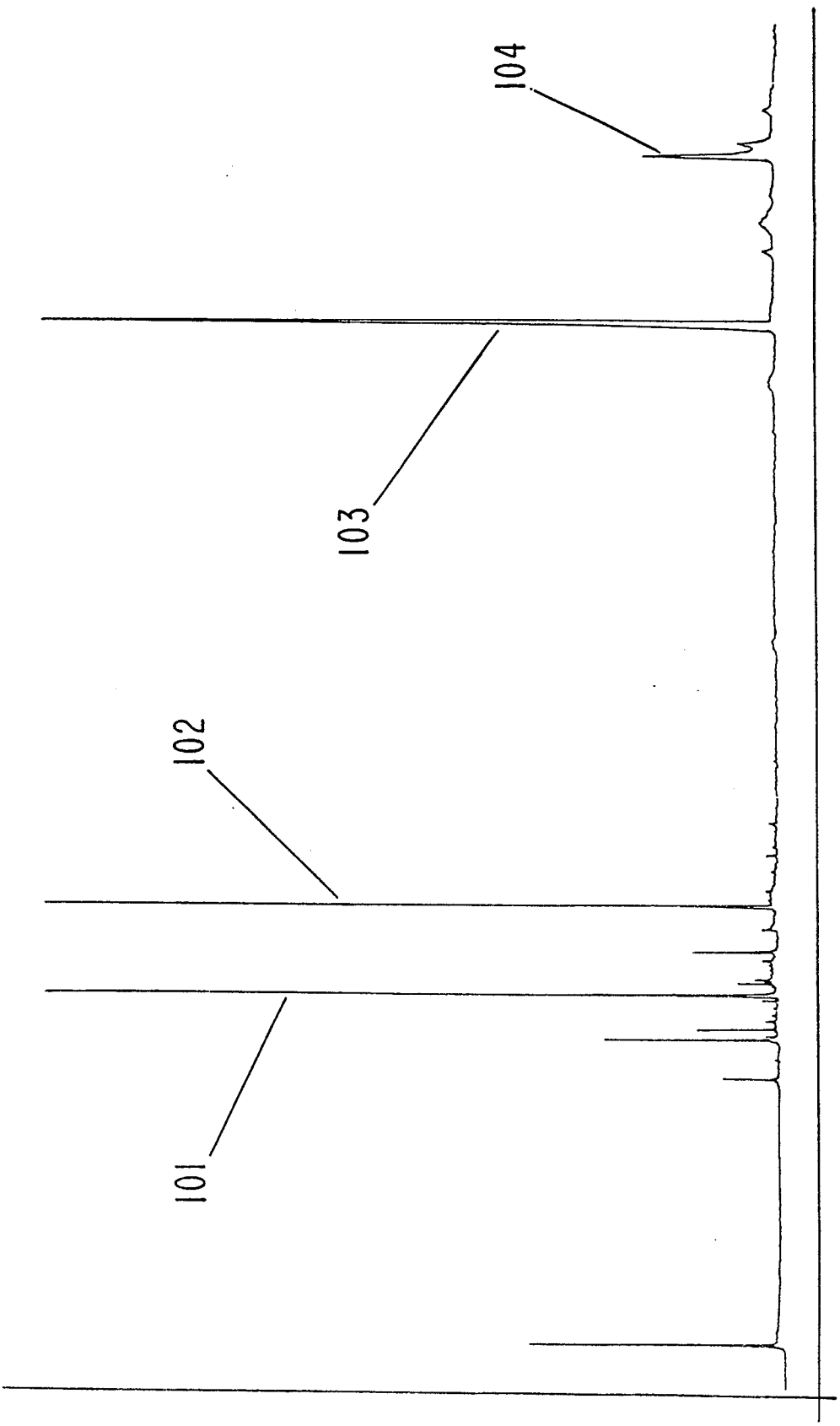
FIG. 1 is the GLC profile for the crude reaction product of Example I containing the reaction products of bergamal and methyl anthranilate, "bergamal" being the compound having the structure.

FIG. 1 is the GLC profile for the crude reaction product of Example I (Conditions: 50 m×0.32 mm OV-1 fused silica column, programmed at 60°–220° C. at 4° C. per minute). The peak indicated by reference numeral 1 is the peak for Bergamal having the structure:

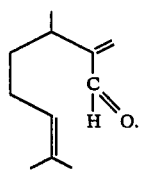

The peak indicated by reference numeral 102 is the peak for methyl anthranilate having the structure:

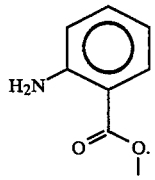

The peaks indicated by reference numerals 103 and 104 are peaks for the schiff base reaction products having the structures:

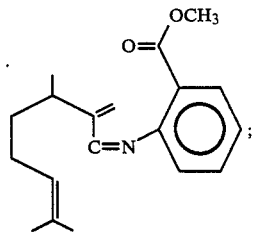

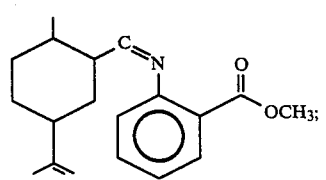

and

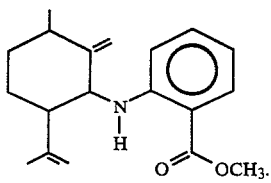

FIG. 3 is the GLC profile for the crude reaction product of Example II (Conditions: 60 m×0.32 mm OV-1 fused silica column, programmed at 60°-220° C. at 4° C. per minute). The peak indicated by reference numeral 30I is the peak for the reaction product, the schiff base having the structure

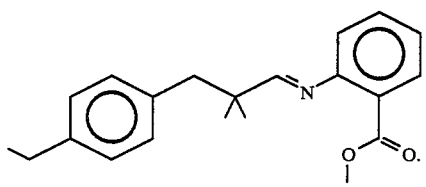

FIG. 5 is the GLC profile for the crude reaction product of Example III (Conditions: 50 m×0.32 mm OV-1 fused silica column, programmed at 60°-220° C. at 4.0° C. per minute). The peak indicated by reference numeral 501 is the peak for methyl anthranilate having the structure:

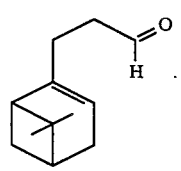

The peak indicated by reference numeral 502 is the peak for the starting material, pino acetaldehyde having the structure:

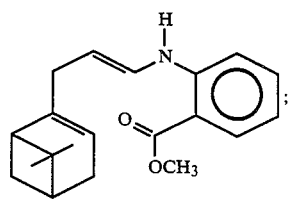

The peaks indicated by reference numerals 503, 504, 505 and 506 are for the schiff base products of pino acetaldehyde and methyl anthranilate having the structures:

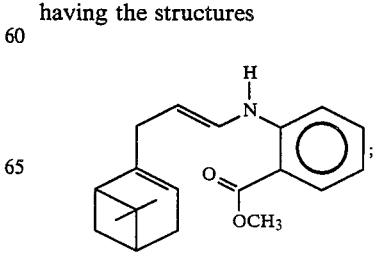

and

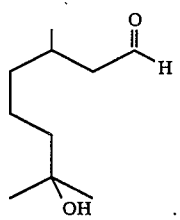

(E and Z isomers).

FIG. 8 is the GLC profile for the crude reaction product of Example IV(A) (mole ratio pino acetaldehyde:hydroxy citronellal:methyl anthranilate =1:2:3))(Conditions: 50 m×0.32 mm OV-1 fused silica column, programmed at 60°-220° C. at 4° C. per minute). The peak indicated by reference numeral 801 is the peak for the hydroxy citronellal reactant having the structure:

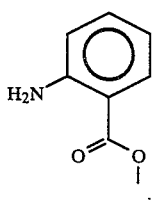

The peak indicated by reference numeral 802 is the peak for the methyl anthranilate reactant having the structure:

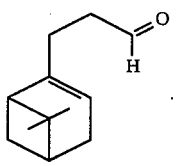

The peak indicated by reference numeral 803 is the peak for the pino acetaldehyde starting material having the structure:

The peaks indicated by reference numerals 804, 805, 806 and 807 are peaks for the schiff base reaction products having the structures -continued

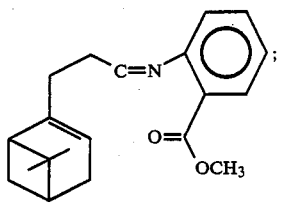

and

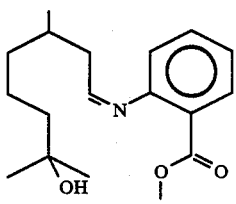

FIG. 9 is the GLC profile for the crude reaction product of Example V, the schiff base reaction product of pino acetaldehyde and lilial with methyl anthranilate with the mole ratio of pino acetaldehyde:lilial:methyl anthranilate being 1:2:3 (Conditions: 50 m×0.32 mm OV-1 fused silica column, programmed at 60°-220° C. at 4° C. per minute). The peak indicated by reference numeral 901 is the peak for the methyl anthranilate having the structure:

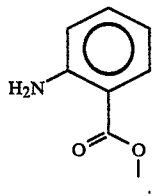

The peak indicated by reference numeral 902 is the peak for the pino acetaldehyde reactant having the structure:

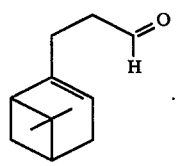

The peak indicated by reference numeral 903 is the peak for the lilial reactant having the structure:

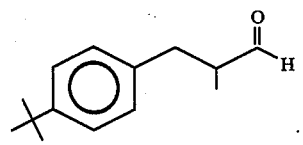

The peaks indicated by reference numerals 904, 905, 906, 907, 908 and 909 are peaks for the schiff base reaction products having the structures:

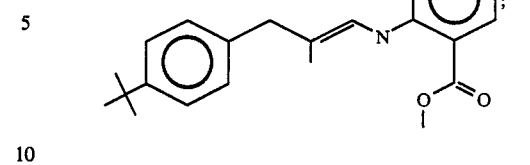

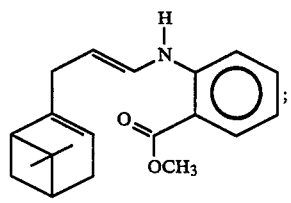

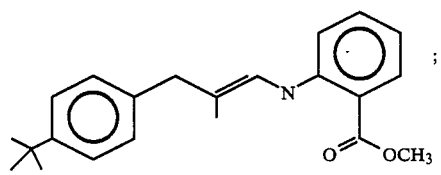

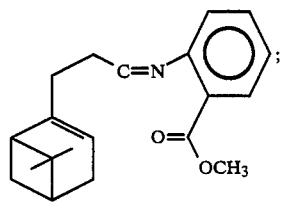

and

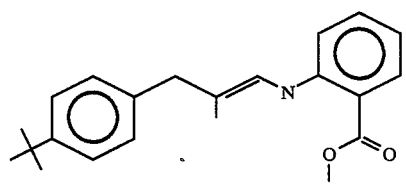

FIG. 12 is the GLC profile for the crude reaction product of Example VI(A) the schiff base reaction product of pino acetaldehyde, lyral and methyl anthranilate with the mole ratio of pino acetaldehyde:lyral:methyl anthranilate being 1:2:3 (Conditions: 50 m×0.32 mm OV-1 fused silica column, programmed at 60°-220° C. at 4° C. per minute). The peak indicated by reference numeral 1201 is the peak for the methyl anthranilate reactant having the structure:

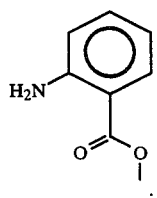

The peak indicated by reference numeral 1202 is the peak for the pino acetaldehyde reactant having the structure:

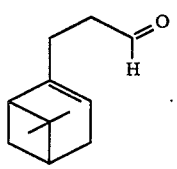

The peak indicated by reference numeral 1203 and the peak indicated by reference numeral 1204 are the peaks for the lyral reactant, lyral being a mixture of two isomers having the structures:

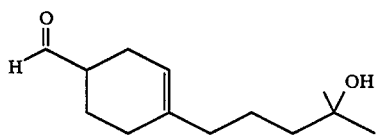

and

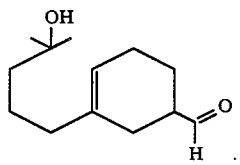

The peaks indicated by reference numerals 1205, 1206, 1207 and 1208 are the peaks for the schiff base reaction products having the structures:

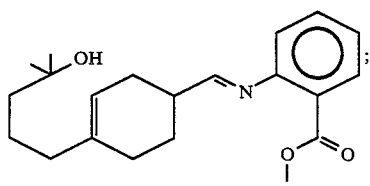

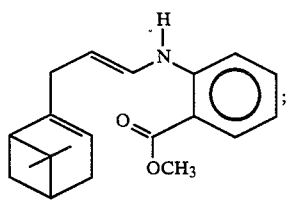

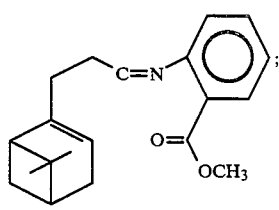

-continued

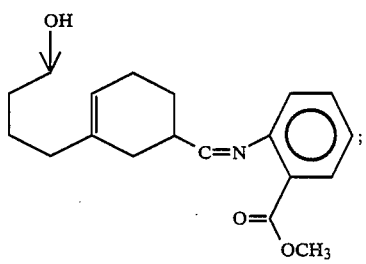

and

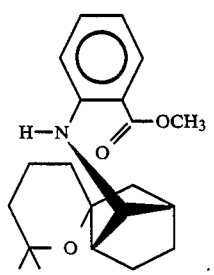

FIG. 13 is the GLC profile for the crude reaction product of Example VI(B), containing the schiff base reaction product of pino acetaldehyde and lyral with methyl anthranilate, the mole ratio of pino acetaldehyde:lyral:methyl anthranilate being 1:1:2 (Conditions: 3'×0.125" 10% SE-30 column programmed at 6° C. per minute). The peaks indicated by reference numerals 1301, 1302 and 1303 are peaks for schiff base reaction products. The peak indicated by reference numeral 1303 is the peak for a mixture of compounds containing more than 50% of the compound having the structure:

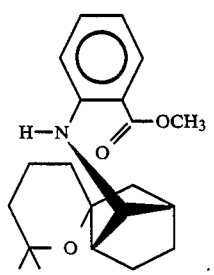

The peaks indicated by reference numerals 1301 and 1302 are for the compounds having the structures:

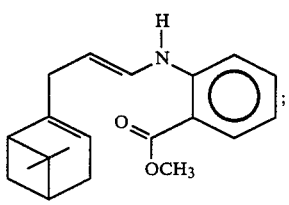

-continued

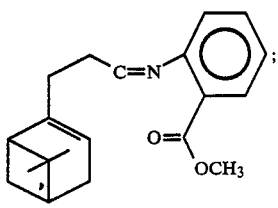

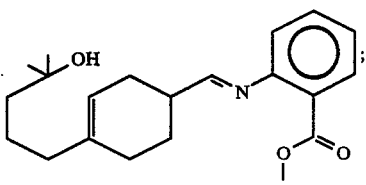

and

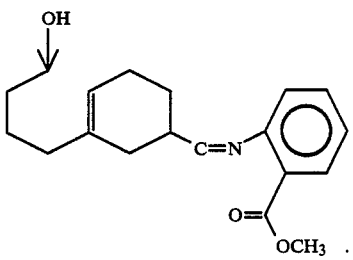

Referring to FIG. 19 is a schematic cut-away elevation diagram of the extrusion and pelletizing apparatus useful in carrying out a process for incorporation of the schiff bases of our invention into polymers during the operation of said apparatus. Motor 15 drives the extruder screws located at 23A in barrel 16, the extruder being operated at temperatures in the range of about 150° up to about 250° C. At the beginning of the barrel resin at source 12 together with additives, e.g., opacifiers, processing aids, colors, pearlescent agents and densifiers at location 13 is added via addition funnel 14 into the extruder. Simultaneously (when the operation reaches "steady state", one or more of the schiff bases of our invention is added to the extruder at one, two or more of barrel segments 3–8 of the extruder (which may be a twin screw or single screw extruder) at locations 18a, 18b, 18c and 18d by means of gear pump 23 from source 17. From source 19 into barrel segments 5–10, the gaseous or liquid blowing agents, e.g., nitrogen, carbon dioxide and the like are added simultaneously with the addition of the schiff base of our invention. The feed rate range of the resin is about 80–300 pounds per hour. The feed rate range of the schiff base taken alone or further together with other perfumant is between 1 and 45% of the feed rate range of the resin. The blowing agent rate range is such that the pressure of the gas or the pressure over the liquid being fed into the extruder is between about 50 and 200 psig. If desired, the extruded ribbon or cylinder may be passed through water bath 20 and pelletizer 21 into collection apparatus 21a.

Referring to FIGS. 20 and 21, there is provided a process for forming scented polymer pellets (wherein the polymer may be thermoplastic polymers such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating cetain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 20 and 21, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymer and the perfuming substance which is at least one of the schiff bases of our invention or mixtures of schiff bases and other compatible perfumes is placed. The container is closed by means of an air-tight lid 228 container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower thereto through a connecting wire 212 portion of the container 212 within a temperature range of 220°–270° C.

Thus, the polymer or mixture of polymers added to the container 212 is heated from 10–12 hours, whereafter the perfume composition or perfume material which contains one or more of the schiff bases of our invention is quickly added to the melt. Generally, about 10–45 percent by weight of the resulting mixture of the perfumery substance is added to the polymer.

After the perfume material containing the schiff base of our invention is added to the container 212 the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the schiff bases of our invention or mixture of perfume substance and one or more of the schiff bases of our invention, will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which is all or which contains one or more of the schiff bases of our invention, through the orifices 234 at a rate which will insure the formation of droplets 236 which will fall downwardly onto a moving conveyor belt 238 to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

FIG. 22 is the GLC profile for the crude reaction product of Example VIII. (Conditions: 50 m×0.32 mm OV-1 column, programmed at 60°-220° C. at 4° C. per minute). The peak indicated by reference numeral 2201 and the peak indicated by reference numeral 2202 are for the compound having the structure:

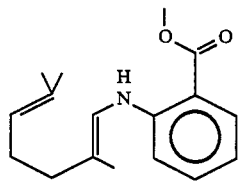

and isomers thereof.

FIG. 25 is the GLC profile for the crude reaction product of Example IX. (Conditions: 2'×0.125" 5% SE-30 column programmed at 230° C. isothermal). The peak indicated by reference numeral 2501 is the peak for the compound having the structure:

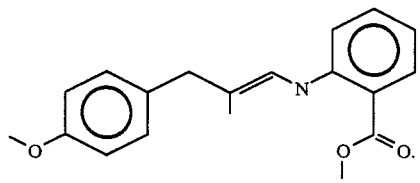

THE INVENTION

Our invention provides schiff base compounds and compositions of matter produced by means of the reaction of alkyl anthranilates having the structure:

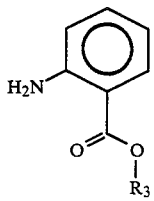

wherein $R_3$ is methyl or ethyl, for example, methyl anthranilate having the structure

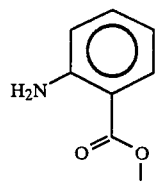

with aldehydes having the structure:

or mixtures of aldehydes having the structures:

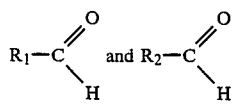

wherein R, $R_1$ and $R_2$ represent alkaryl, aralkyl, alkadienyl, hydroxyalkyl, alkenylcycloalkyl, hydroxyalkyl cycloalkenyl and alkoxyaralkyl.

More specifically, the novel compounds of our invention are produced by reaction of alkyl anthranilates having the structure:

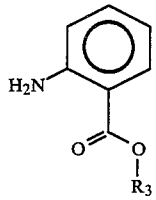

with aldehydes having the structure:

wherein such aldehydes have the structures:

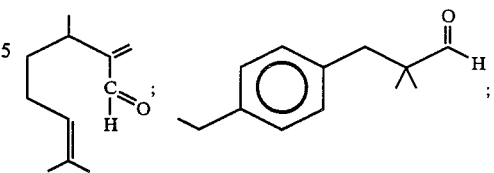

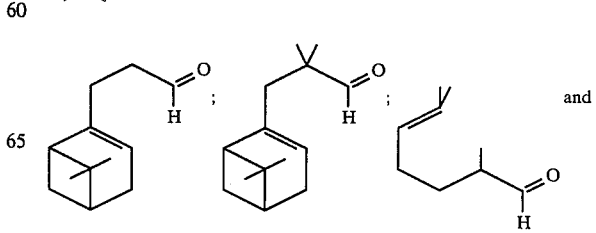

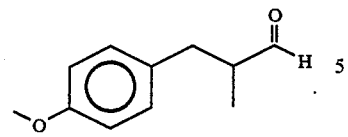

Furthermore, the mixtures of aldehydes having the structures:

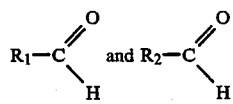

include the compound having the structure:

as specified, supra, taken further together with at least one of the following aldehydes having the following structures:
(i) the compound having the structure:

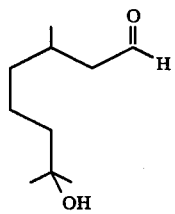

(hydroxy citronellal);
(ii) the compound having the structure:

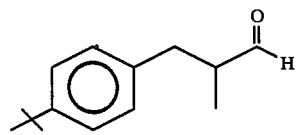

("lilial"); and
(iii) the mixture of compounds having the structures:

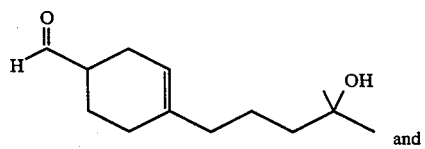

and

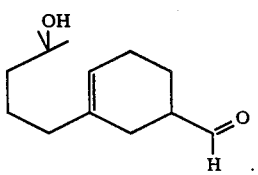

The reaction products of our invention are collectively termed "schiff bases"; but not all of the products produced according to the "schiff base" reaction set forth, supra, and specifically set forth, infra, contain the moiety:

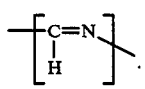

Thus, as will be seen, infra, the reaction of the compound having the structure:

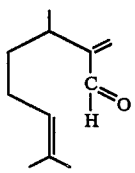

(also denoted herein as "Bergamal") with the compound having the structure:

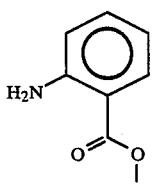

yields a small amount of the compound having the structure:

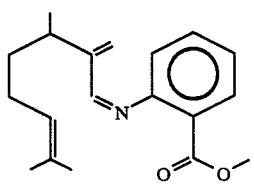

and larger amounts of the compounds having the structures:

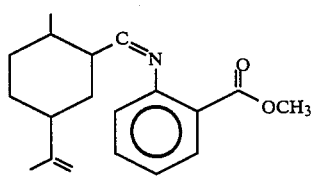

and

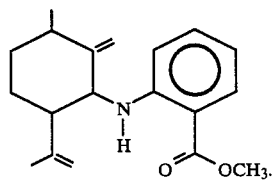

resulting schiff bases of our invention produced according to the process of our invention are capable of augmenting or enhancing grape aromas and tastes of foodstuffs, chewing gums, toothpastes, medicinal products and chewing tobaccos.

The schiff bases of our invention as well as mixtures thereof produced according to the process of our invention are also capable of modifying or enhancing the aroma characteristics of perfume compositions, colognes and perfumed articles (including soaps, anionic, cationic, nonionic or zwitterionic detergents, fabric softener compositions, optical brightener compositions and drier-added fabric softener articles) and perfumed polymers by imparting thereto intense lemony, floral, green, ozoney, fruity, melony, citrus, piney, grape-like, woody, sweet and muguet aromas with anisic, fresh cut wood, ozoney, fresh air, floral and orange flower topnotes as well as anisic, woody, floral, green and citrus undertones, thus fulfilling a need in the field of perfumery and detergent and cosmetics manufacture.

The schiff bases of our invention are also capable of deodorizing detergent powders suitable for use in the washing of fabrics as well as detergent powders as well as hand soaps. Such detergent powders include bleaching compositions, for example, bleaching compositions comprising a peroxy bleach compound. The schiff bases of our invention have deodorancy as measured by having a Lipoxidase-inhibiting capacity of at least 50% and a Raoult Variance ratio of at least 1.1 and a malodour reduction value of between about 0.25 up to 3.0 as measured by the malodour reduction value test disclosed in U.S. Pat. No. 4,663,068 the specification for which is incorporated by reference herein; and in addition, a deodorant value of from 0.50 up to 3.5 as measured by the deodorant value test disclosed in U.S. Pat. No. 4,304,679 the specification for which is incorporated by reference herein.

The reaction to form the schiff base between the aldehyde having the structure:

or the mixture of aldehydes having the structures:

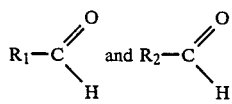

wherein $R_1$, $R_2$ and R are defined, supra, and the alkyl anthranilate having the structure:

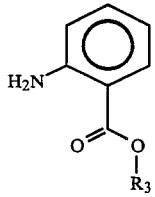

wherein $R_3$ is methyl or ethyl are as follows:
(i) the temperature of the reaction is in the range of from about 90° C. up to about 150° C.;
(ii) the pressure over the reaction mass may vary from about 3 mm/Hg. (vacuum) up to about 1 atmosphere with a preferable pressure of between about 5 and about 100 mm/Hg. pressure;
(iii) the time of reaction may vary from about 5 up to about 15 hours with a preferred time of reaction of between about 6 and about 12 hours; (iv) the mole ratio of aldehyde having the structure:

or mixture of aldehydes having the structure:

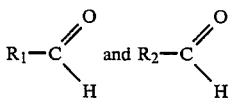

to alkyl anthranilate having the structure:

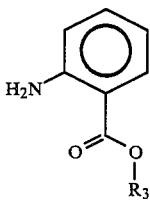

may vary from about 1:1 up to about 1.25:1 of total aldehyde:alkyl anthranilate with a preferred mole ratio of between about 1:1 and about 1.1:1 aldehyde:alkyl anthranilate.

At the end of the reaction, the reaction mass may be separated and the reaction product purified as by fractional distillation of the schiff base or schiff base reaction product. From a practical standpoint when a reaction mixture is created which gives rise to preferred perfumery properties subsequent fractional distillation to the point of yielding an odor acceptable product is what is desired.

The following table sets forth reactants, schiff base reaction product structures (to the extent known) and organoleptic properties of the resulting products.

TABLE I

| Reactants | Schiff Base Reaction Product Structures (to the extent known) | Organoleptic Properties; Perfumery & Flavor |
|---|---|---|
| Bergamal having the structure: | Product produced according to Example | A lemony and floral aroma |

TABLE I-continued

| Reactants | Schiff Base Reaction Product Structures (to the extent known) | Organoleptic Properties; Perfumery & Flavor |
|---|---|---|
| *(structure of citronellal-like aldehyde)* and methyl anthranilate having the structure: *(structure of methyl anthranilate, H₂N-C₆H₄-COOCH₃)* | I containing the compounds having the structures: *(Schiff base structure with OCH₃ group)* *(cyclized product structure with OCH₃)* *(N-H cyclized product with OCH₃)* | profile. |
| Floralozone having the structure: *(structure of Floralozone: 4-ethylphenyl-CH₂-C(CH₃)₂-CHO)* and methyl anthranilate having the structure: *(structure of methyl anthranilate)* | The compound having the structure: *(Schiff base structure with C=N and OCH₃)* produced according to Example II. | A green, floral and ozoney aroma anisic topnotes. |
| Pino acetaldehyde having the structure: | Compounds having the structures: | A melony and floral aroma profile. |

TABLE I-continued

| Reactants | Schiff Base Reaction Product Structures (to the extent known) | Organoleptic Properties; Perfumery & Flavor |
|---|---|---|
| and methyl anthranilate having the structure: <br> Pino acetaldehyde having the structure: | and <br> Compounds having the structures: | A citrus, green and piney aroma with anisic, woody and floral undertones. |
| hydroxy citronellal having the structure: <br> and methyl anthranilate having the structure: <br> with the mole ratio of pino acetaldehyde: hydroxy citronellal: | and <br> prepared according to Example IV (A). | |

TABLE I-continued

| Reactants | Schiff Base Reaction Product Structures (to the extent known) | Organoleptic Properties; Perfumery & Flavor |
|---|---|---|
| methyl anthranilate being 1:2:3. Pino acetaldehyde having the structure: 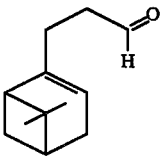 hydroxy citronellal having the structure: 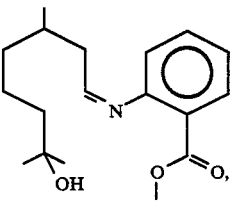 and methyl anthranilate having the structure: 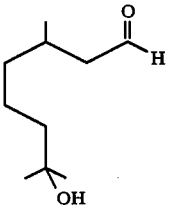 with the mole ratio of pino acetaldehyde: hydroxy citronellal: methyl anthranilate being 1:1:2. | Compounds having the structures: 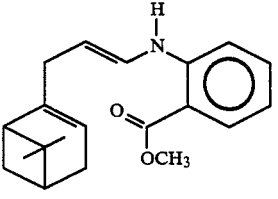 and 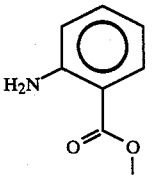 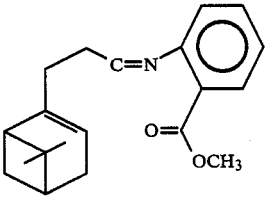 prepared according to Example IV(B). | A floral, ozoney, green and grape-like aroma profile. |
| Mixture of Pino acetaldehyde having the structure: 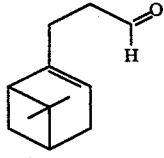 lilial having the structure: | Mixture of compounds having the structures: 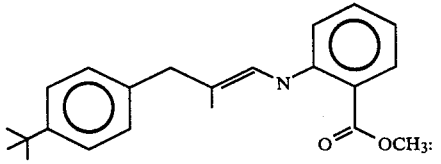 | A floral and grape-like aroma with green and citrus under-tones. |

TABLE I-continued

| Reactants | Schiff Base Reaction Product Structures (to the extent known) | Organoleptic Properties; Perfumery & Flavor |
|---|---|---|
| 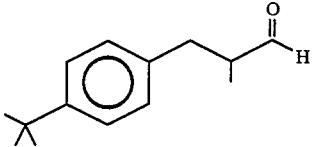 and methyl anthranilate having the structure: 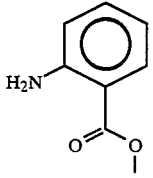 with the mole ratio of pino acetaldehyde:lilial:methyl anthranilate being 1:2:3. | 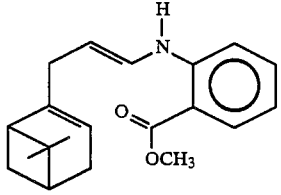 and 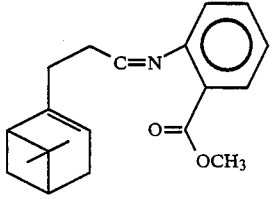 prepared according to Example V(A). | |
| Mixture of Pino acetaldehyde having the structure: 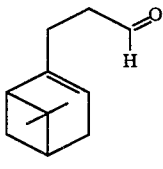 lilial having the structure: 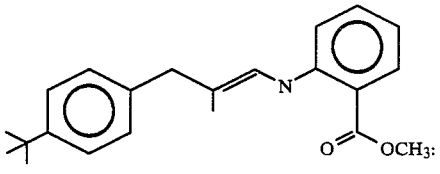 and methyl anthranilate having the structure: 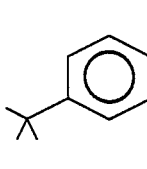 with the mole ratio of pino acetaldehyde lilial:methyl:anthranilate being 1:1:2. | Mixtures of compounds having the structures: 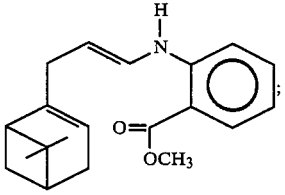 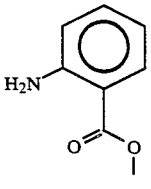 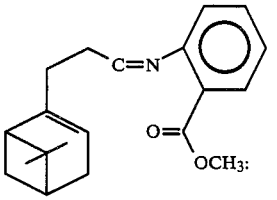 prepared according to Example V(B). | A woody, piney, and grape-like aroma with fresh cut wood and ozoney topnotes. |
| Mixture of pino acetaldehyde having the | A mixture of compounds having the structures: structures: | A citrus, green and floral aroma profile with |

TABLE I-continued

| Reactants | Schiff Base Reaction Product Structures (to the extent known) | Organoleptic Properties; Perfumery & Flavor |
|---|---|---|
| structure: 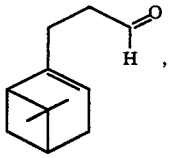 lyral, a mixture of compounds having the structures: 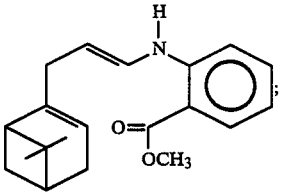 and 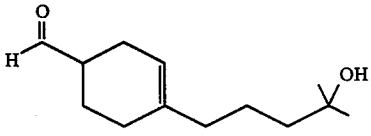 and methyl anthranilate having the structure: 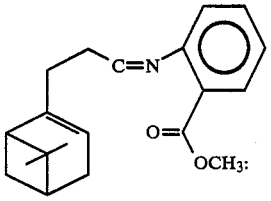 with the mole ratio of pino acetaldehyde:lyral:methyl anthranilate being 1:2:3. | 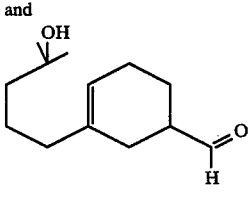 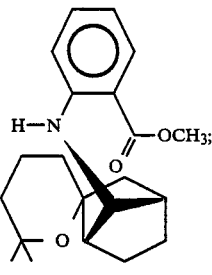 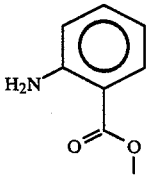 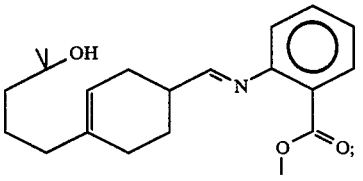 and 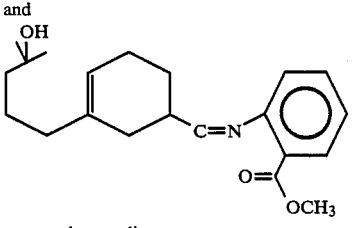 prepared according to Example VI(A). | fresh air and ozoney topnotes. |
| A mixture of pino acetaldehyde having the structure: | A mixture of compounds having the structures: | A sweet, citrus, green and melony aroma profile with ozoney and floral topnotes. |

TABLE I-continued

| Reactants | Schiff Base Reaction Product Structures (to the extent known) | Organoleptic Properties; Perfumery & Flavor |
|---|---|---|
| [structure: pino acetaldehyde] ; lyral a mixture of compounds having the structures: [structure with CHO and OH]; and [structure with OH and CHO]; and methyl anthranilate having the structure: [methyl anthranilate structure]; with the mole ratio of pino acetaldehyde:lyral:methyl anthranilate being 1:1:2. | [Schiff base structure with OH, N, OCH₃ ester]; [cage-like structure with H—N, OCH₃]; [structure with N—H, OCH₃]; and [C=N structure with OCH₃]; and [OH structure with C=N, OCH₃] prepared according to Example VI(B). Compound having the structure: | |
| Mixture of pino isobutyraldehyde having the structure: | | A fresh and green aroma profile. |

TABLE I-continued

| Reactants | Schiff Base Reaction Product Structures (to the extent known) | Organoleptic Properties; Perfumery & Flavor |
|---|---|---|
| 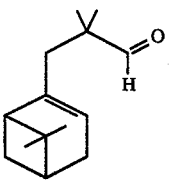 and methyl anthranilate having the structure: 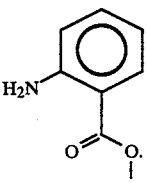 | 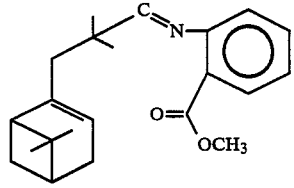 prepared according to Example VII. | |
| Mixture of melonal having the structure: 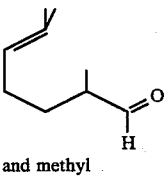 and methyl anthranilate having the structure: 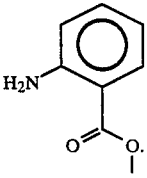 | The compound having the structure: 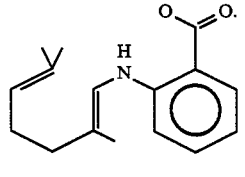 | A muguet, fruity, green, melony and grape-like aroma with orange flower topnotes. |
| Mixture of canthoxal having the structure: 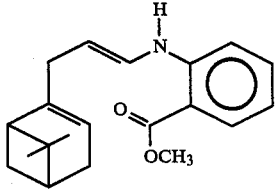 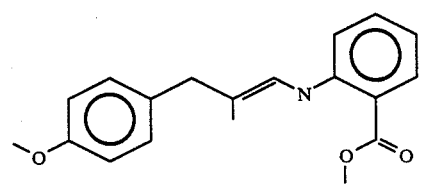 and methyl anthranilate having the structure: | Compound having the structure: 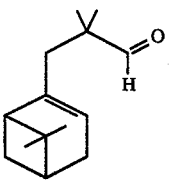 producted according to Example IX. | A sweet floral fruity and ozoney aroma with anisic topnotes; and a grape flavor at 0.1 ppm causing it to be useful in grape and mandarin flavored beverages. |
| 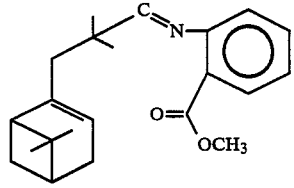 | | |

TABLE I-continued

| Reactants | Schiff Base Reaction Product Structures (to the extent known) | Organoleptic Properties; Perfumery & Flavor |
|---|---|---|
| (structure: 2-aminobenzoate with H$_2$N and O=C-O- groups on benzene ring) | | |

When one or more of the schiff bases and reaction products containing same of our invention is used as a food flavor adjuvant, the nature of the co-ingredients included with said schiff bases in formulating the product composition will also serve to alter the organoleptic characteristics of the ultimate foodstuffs treated therewith. As used herein in regard to flavors the term "alter" in its various forms means "supplying or imparting flavor character or notes to otherwise bland relatively tasteless substance or augmenting the existing flavor characteristic where a natural flavor is deficient in some regard or supplementing the existing flavor impression to modify its quality, character or taste".

As used herein, the term "foodstuff" includes both solid and liquid ingestible materials which usually do but need not have nutritional value. Thus, foodstuffs include soups, convenience foods, beverages, dairy products, candies, fruit cereals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3-tertiary butyl-4-hydroxyanisole), butylated hydroxy toluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agaragar; carrageenan; cellulose and cellulose derivatives such as carboxymethyl cellulose and methyl cellulose; natural and synthetic gums such as gum arabic, gum tragacanth; gelatin; proteinaceous materials; lipids; carbohydrates; starches, pectins, and emulisifiers, e.g., mono- and diglycerides of fatty acids, skim milk powder, hexoses, pentoses, disaccharides, e.g., sucrose, corn syrup solids and the like. Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, turmeric and curcumin and the like; firming agents such as aluminum sodium sulfate, calcium chloride and calcium gluconate; texturizers; anti-caking agents, e.g., aluminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, butyric acid, caproic acid, caprylic acid, formic acid, 2-hexenoic acid, 3-hexenoic acid, isobutyric acid, isovaleric acid, propionic acid and valeric acid; ketones and aldehydes, e.g., acetaldehyde, acetone, acetyl methyl carbinol, acrolein, diacetyl $\beta$, $\beta$-dimethylacrolein, hexanal, 2-hexenal, cis-3-hexenal, 4(p-hydroxyphenyl)-2-butanone, alpha-ionone, B-ionone, and 2-pentenal; alcohols, such as 1-butanol, trans-2-buten-1-ol, ethanol, geraniol, 1-hexanol, cis-3-hexen-1-ol, 3-methyl-3-buten-1-ol, 1-pentanol, 1-penten-3-ol; esters, such as butyl acetate, ethyl acetate, ethyl butyrate, ethyl crotonate, ethyl propionate, 2-hexenyl acetate, 2-hexenyl butyrate, hexyl acetate, hexyl butyrate, isoamyl acetate, isopropyl butyrate, methyl butyrate, methyl caproate, methyl caprylate, propyl acetate, amyl acetate, amyl butyrate, benzyl salicylate, dimethyl anthranilate, ethyl methylphenylglycidate, ethyl succinate, isobutyl cinnamate, and terpenyl acetate; essential oils such as jasmine absolute, rose absolute, orris absolute, lemon essential oil and vanilla; lactones; sulfides, e.g., methyl sulfide and other materials such as maltol and citral as well as natural raspberry oil, orange oil, mango extract, pickled mango extract and natural cranberry juice concentrate, strawberry juice concentrate.

The specific flavoring adjuvants selected for use may be either solid or liquid, depending upon the desired physical form of the ultimate product, i.e., foodstuff, whether simulated or natural, and should, in any event, be capable of providing an environment in which the schiff bases of our invention can be disbursed or admixed to provide a homogeneous medium. In addition, selection of one or more adjuvants, as well as the quantities thereof, will depend upon the precise organoleptic grape character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount in which the schiff bases of our invention employed in a particular instance can vary over a relatively wide range whereby its desired organoleptic effects (having reference to the nature of the product) are achieved. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for the purposes of enhancing the composition merely deficient in natural flavor or aroma. Thus, the primary requirements is that amount which is effective, i.e., sufficient to alter the organoleptic characteristics of the parent composition, whether foodstuff per se or flavoring composition. Thus, the use of insufficient quantities in which the schiff bases of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus and with respect to ultimate food compositions, it has been found that quantities in which the schiff bases of our invention ranging from a small but effective amount, e.g., 0.02 parts per million up to about 50 parts per million by weight based on total composition are suitable. Concentrations in excess of the maximum quantity stated are not normally recommended since they fail to provide commensurate enhancement of organoleptic properties. In those cases wherein in which the schiff bases of our invention is added to the foodstuff as an integral component of the flavoring composition, it is, of course, essential that the total quantity of flavoring composition employed be sufficient to yield an effective schiff base concentration in the foodstuff product.

The composition described herein can be prepared according to conventional techniques well known as typified by cake batters and fruit juices and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing the schiff bases of our invention with, for example, gum arabic, gum tragacanth, carrageenan and the like and thereafter spray-drying the resultant mixture whereby to obtain the particulate solid product. Prepared flavor mixes in powder form, e.g., a raspberry flavored powder are obtained by mixing dried solid, components, e.g., starch, sugar and the like and the schiff bases of our invention in a dry blender until the requisite degree of uniformity is achieved.

It is presently preferred to combine the schiff bases of our invention with the following adjuvants:
acetone;
Vanilin;
Maltol;
Alpha-Ionone;
Beta-Ionone;
Isobutyl acetate;
Ethyl butyrate;
Dimethyl sulfide;
Acetic acid;
Acetaldehyde;
4-(2,6,6-trimethyl-1,3-cyclohexadien-1-yl)-2-butanone;
4-(6,6-dimethyl-2-methylene-3-cyclohexen-1-yl)-2-butanone;
2-(4-hydroxy-4-methylpentyl)norbornadiene produced according to Example I of U.S. Pat. No. 3,911,028;
Beta-Damascone(1-crotonyl-2,6,6-trimethylcyclohex-1-ene)
Beta-Damascenone(1-crotonyl-2,6,6-trimethylcyclohexa-1,3-dien);
Beta-cyclohomocitral(2,6,6-trimethylcyclohex-1-ene carboxaldehyde);
Isoamyl butyrate;
Cis-3-hexenol-1;
Elemecine(4-allyl-1,2,6-trimethoxybenzene);
Isoelemecine(4-propenyl-1,2,6-trimethoxybenzene);
Ethyl ester of 2-hydroxy butyric acid;
Ethyl-2-methyl-3-pentenoate;
Ethyl ester of 3-hydroxy butyric acid;
Orange oil;
Lemon oil;
Grape juice concentrate;
Cranberry juice concentrate;
Mango extract; and
Pickled mango extract.

One or more schiff bases prepared in accordance with the of our invention and one or more auxiliary perfume ingredients including, for example, alcohols, aldehydes, ketones, terpinic hydrocarbons, nitriles, esters, lactones, natural essential oils and synthetic essential oils may be admixed so that the combined odors of the individual components produce a pleasant and desired fragrance, particularly, and preferably, in pine, floral and lavender fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the over-all sensory effect of the perfume composition will be at least the sum total of the effects of each of the ingredients Thus, schiff base derivatives prepared in accordance with the process of our invention, can be used to alter, modify or enhance the aroma characteristics of a perfume composition, for example, by utilizing or moderating the olfactory reaction contributed by another ingredient in the composition The mount of schiff base derivatives prepared in accordance with the process of our invention which will be effective in perfume compositions as well as in perfumed articles (e.g., anionic, nonionic, cationic and zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions containing as little as 0.01% of schiff base derivatives prepared in accordance with the process of our invention and less than 50% of schiff base derivatives prepared in accordance with the process of our invention or even less (e.g., 0.005%) can be used to impart lemony, floral, green, ozoney, fruity, melony, citrus, piney, grape-like, woody, sweet and muguet aroma with anisic, fresh cut wood, ozoney, fresh air, floral and orange flower topnotes and anisic, woody, floral, green and citrus undertones to solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

The schiff base derivatives prepared in accordance with the process of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, and perfumed polymers and articles of manufacture produce from said perfumed polymers. When used as (an) olfactory component(s) as little as 0.2% of schiff base derivatives prepared in accordance with the process of our invention will suffice to impart an intense lemony, floral, green, ozoney, fruity, melony, citrus, piney, grape-like, woody, sweet and muguet aroma with anisic, fresh cut wood, ozoney, fresh air, floral and orange flower topnotes and anisic, woody, floral, green and citrus undertones to floral, piney, lemony and rose and fresh air formulations. Generally, no more than 6% of one or more schiff bases of our invention based on the ultimate end product is required in the perfumed article composition. Accordingly, the range of schiff bases in the perfumed articles is from about 0.2% by weight of the schiff bases up to about 6% by weight based on the perfumed article. In addition, the perfume composition or fragrance composition of our invention can contain a vehicle or carrier for one or more of the schiff base derivatives prepared in accordance with the process of our invention. The vehicle can be a liquid, such as a non-toxic alcohol, e.g., ethyl alcohol, a non-toxic glycol, e.g., propylene glycol or the like. The carrier can also be an absorbent solid, such as a gum (e.g., gum arabic, guar gum or xanthan gum) or components for encapsulating the composition (such as gelatin) as by coacervation; or such as urea-formaldehyde polymer forming a capsule shell around a liquid perfumed center.

Our invention also relates to the utilization of controlled release technology for the controlled release of perfumes into gaseous environments from polymers such as mixtures of epsilon polycaprolactone polymers and polyethylene which polyepsilon caprolactone polymers are defined according to at least one of the structures:

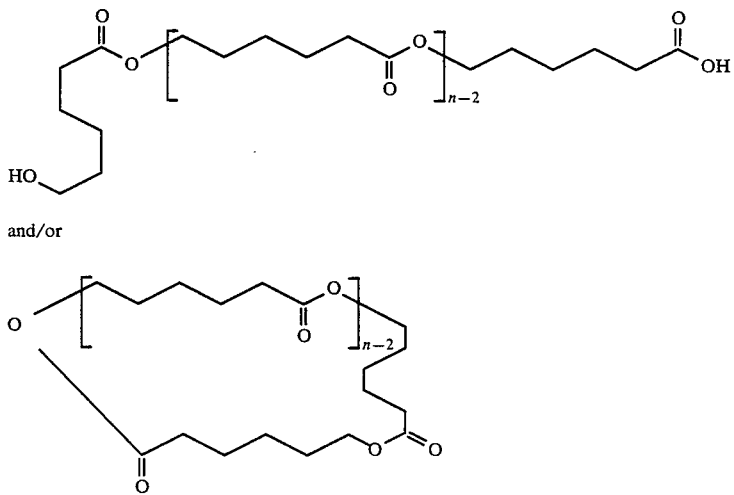

and/or wherein "n" is from about 50 up to about 1,200 with the proviso that the average "n" in the system varies from about 150 up to about 700 according to the mathematical statement:

$$[700 \geq \bar{n} \geq 150]$$

with the term $\bar{n}$ being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$\frac{dM_t}{dt} = k_1 e^{-k_2 t}$$

wherein $k_1$ and $k_2$ are constants. According to Kydonieus, "Controlled Release Technologies: Methods, Theory, and Applications" (cited, supra, the amount of perfume composition released is proportional to time as long as the concentration of perfume material present, e.g., the schiff bases of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release constant (zero order) as long as the surface area does not change during the erosion period. This is the case with the polymers containing the schiff bases of our invention.

The polyepsilon caprolactone polymers useful in practicing our invention are more specifically described in the brochure of the Union Carbide Corporation, 270 Park Avenue, New York, N.Y.10017, entitled "NEW POLYCAPROLACTONE TERMOPLASTIC POLYMERS PCL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such as hydroquinone or compounds having the formula:

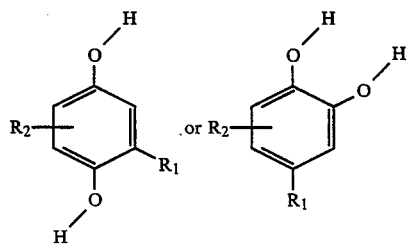

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfer with the functional fluids dissolved and/or adsorbed into the polymeric matrix. The method of incorporating the schiff bases of our invention or perfume compositions containing same into the polymers may be according to the technique of U.S. Pat. No. 3,505,432 issued on Apr. 7, 1970 (the specification for which is incorporated by reference herein) or U.S. Pat. No. 4,247,498 issued on Jan. 7, 1981, the disclosure of which is incorporated by reference herein.

Thus, for example, a first amount of liquid polyethylene-polyepsilon caprolactone polymer mixture (50:50) is mixed with one of the schiff bases of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus in accordance with one aspect of our invention the imparting of scent is effected in two stages. In a first stage, a 50:50 (weight:weight) polyepsilon caprolactone, e.g., PCL-700: polyethylene in molten form is admixed with a high percentage of one of the schiff bases of our invention and the mixture is solidified in the form of pellets or beads. These pellets or beads thus contain a high percentage of schiff bases (e.g., up to 45% by weight of the entire mixture) and may be used as 'master pellets' which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention at least one of the schiff bases of our invention is added to the polymer in a large closed container or drum which is maintained under controlled temperature conditions while the polymer in a melted condition is mixed with at least one of the schiff bases under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by at least one of the schiff bases of our invention is permitted to drip through the orifices onto a continuously moving, cooled conveyor upon which the polymer containing at least one of the schiff bases of our invention solidifies into small size pellets with the perfume imprisoned therein. The apparatus useful in conjunction with this process advantageously includes a conveyor of a material which will not adhere to the polymer which contains at least one of the schiff bases of our invention.

In order that the droplets form into uniform pellets or beads, the conveyor is continuously washed with a liquid such as water to maintain the surface relatively cool. The pellets are delivered by the conveyor into a container and packaged for shipment.

The following Examples I–X serve to illustrate processes for preparing the schiff bas of our invention. The examples following Example IX are illustrative of the organoleptic utilities of the schiff bases of our invention. All parts and percentages given herein are by weight unless otherwise specified.

EXAMPLE I

PREPARATION SCHIFF BASE OF METHYL ANTHRANILATE AND BERGAMAL

Reaction:

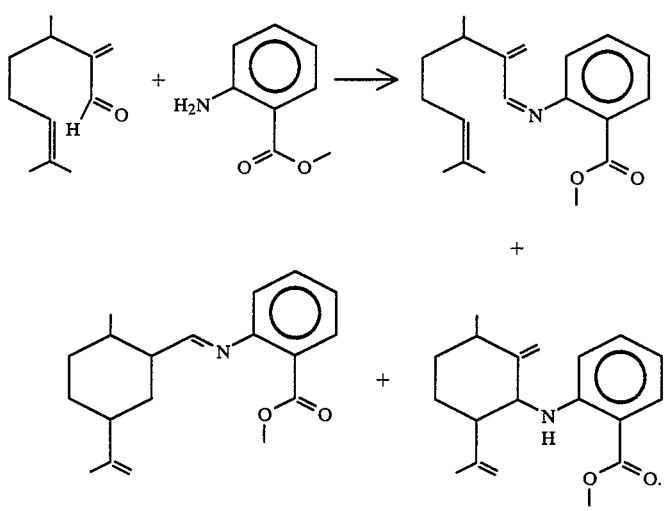

Into a 2 liter, 3 neck reaction flask equipped with stirrer, thermometer, glass "Y" adapter, 1 liter addition funnel, steam distillation head with a 45/50 bottom male joint attached to the reaction flask, head thermometer, curved fraction cutter with a 50 ml receiver, heating mantle controlled with a "Therm-O-Watch", dry ice trap, Bennert Manometer, vacuum bleed valve and vacuum pump is placed 302.0 grams of methyl anthranilate having the structure:

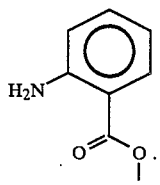

With stirring using the 1 liter addition funnel, 332.0 grams of Bergamal having the structure:

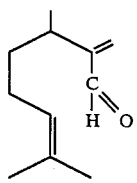

is added dropwise to the reaction mass over a one hour period while slowly heating the reaction mass to 50° C.

The 1 liter addition funnel is then removed from the reaction flask and vacuum (50.0 mm/Hg.) is applied to the system.

With stirring, the reaction mass is gradually heated to 100° C. over a 45 minute period.

Heating is continued at 100° C. for a period of eight hours while removing water at a vapor temperature of 35°–45° C.

The reaction flask is then cooled to 50° C.

The resulting product has an intense lemony and floral aroma.

FIG. 1 is the GLC profile for the reaction product. The peak indicated by reference numeral 101 is the peak for the Bergamal having the structure:

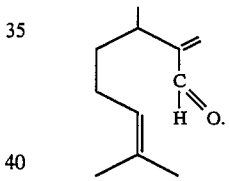

The peak indicated by reference numeral 102 is the peak for methyl anthranilate having the structures:

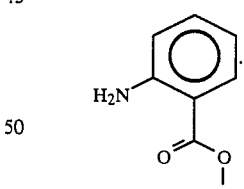

The peaks indicated by reference numerals 103 and 104 are the peaks for the schiff base reaction products having the structures:

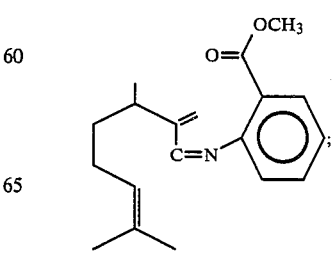

-continued

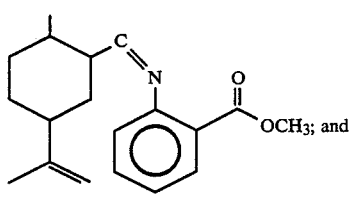

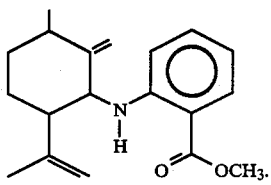

FIG. 2 is the NMR spectrum for a schiff base reaction product of Example I containing the compounds having the structures:

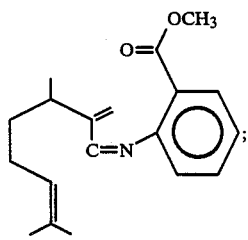

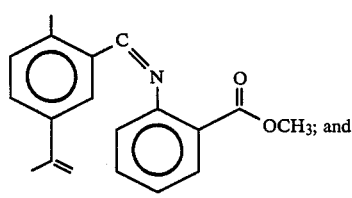

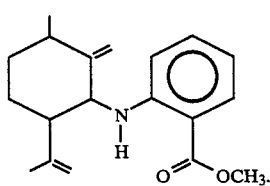

EXAMPLE II

PREPARATION OF SCHIFF BASE REACTION PRODUCT OF FLORALOZONE AND METHYL ANTHRANILATE

Reaction:

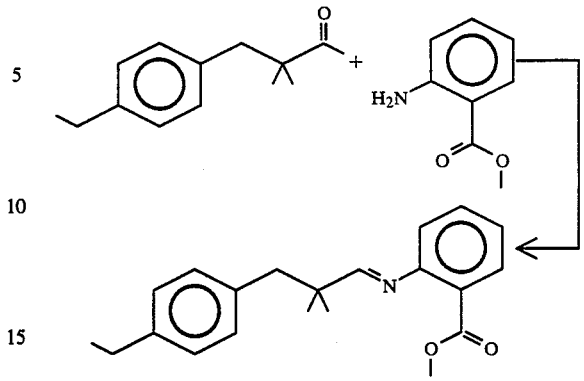

Into a 2 liter, 3 neck reaction flask equipped with mechanical stirrer, addition funnel, thermometer, reflux condenser and heating mantle is added 226.5 grams (1.5 moles) of methyl anthranilate having the structure:

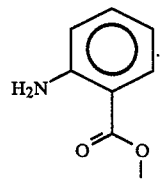

The reaction mass is heated to 50° C. and 285 grams (1.5 moles) of floralozone having the structure:

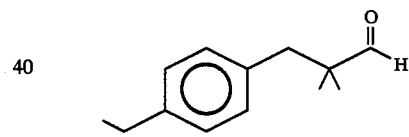

is added over an one hour period.

The reaction contents are then placed under 50 mm/Hg. of vacuum and heated to 140° C. for eleven hours.

After this period of time, the reaction mass is cooled and vacuum filtered through a bed of anhydrous magnesium sulfate. The total yield is 500 grams and NMR, IR, and mass spectral analyses yield the information that the reaction product has the structure:

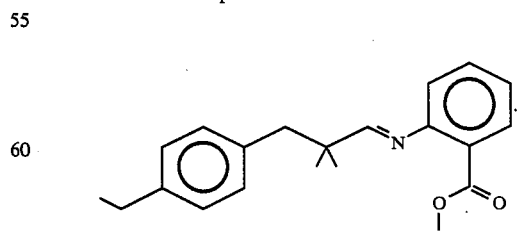

The reaction product (334 grams) is then distilled on a short path distillation column to yield the following fractions:

| Fraction No. | Vapor Temp. (0° C.) | Liquid Temp. (0° C.) | Vacuum mm/Hg. Pressure | Weight of Fraction |
|---|---|---|---|---|
| 1 | 74/73 | 110/117 | 3/3 | 49.77 |
| 2 | 72 | 126 | 3.0 | 47.13 |
| 3 | 69 | 123 | 3.0 | 47.58 |
| 4 | 156 | 210 | 2.0 | 14.82 |
| 5 | 169 | 212 | 2.0 | 30.65 |
| 6 | 169 | 221 | 2.0 | 71.98 |
| 7 | 168 | 244 | 2.0 | 64.57 |

FIG. 3 is the GLC profile for the reaction product of this example (Conditions: 60 m×0.32 mm OV-1 fused silica column, programmed at 60°-220° C. at 4° C. per minute). The peak indicated by reference numeral 301 is the peak for the reaction product having the structure:

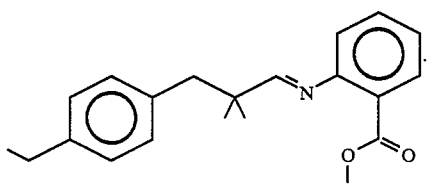

FIG. 4 is the NMR spectrum for the compound having the structure:

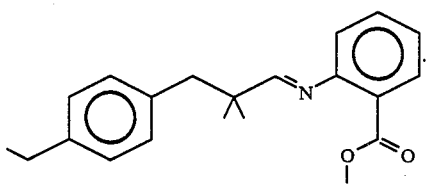

The resulting product has a green, floral and ozoney aroma profile with anisic topnotes.

EXAMPLE III

PREPARATION OF SCHIFF BASE REACTION PRODUCT OF METHYL ANTHRANILATE AND PINO ACETALDEHYDE

Reaction:

Into a 2 liter, 3 neck reaction flask equipped with mechanical stirrer, pot thermometer, glass "Y" adapter, 1 liter addition funnel, steam distillation head with a 45/50 bottom male joint attached to the reaction flask, head thermometer, curved fraction cutter with a 50 ml receiver, heating mantle controlled with a "Therm-O-Watch", dry ice trap, Bennert Manometer, vacuum bleed valve and vacuum pump is placed 302.0 grams of methyl anthranilate having the structure:

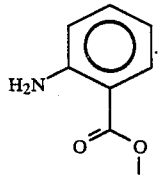

With stirring, via the one liter addition funnel, 454.0 grams of pino acetaldehyde having the structure:

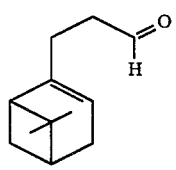

is added dropwise over a one hour period while slowly heating the reaction mass to 50° C.

The one liter addition funnel is then removed from the reaction flask and 50 mm vacuum is applied to the system.

With stirring over a period of 45 minutes, the reaction mass is heated to 115° C. The reaction mass is then heated with stirring at 115° C. for a seven hour period while removing water at a vapor temperature of 35°-45° C.

The reaction mass is then cooled to 50° C. The resulting product (weight: 720 grams) is then analyzed and it is determined to contain the compounds having the structures:

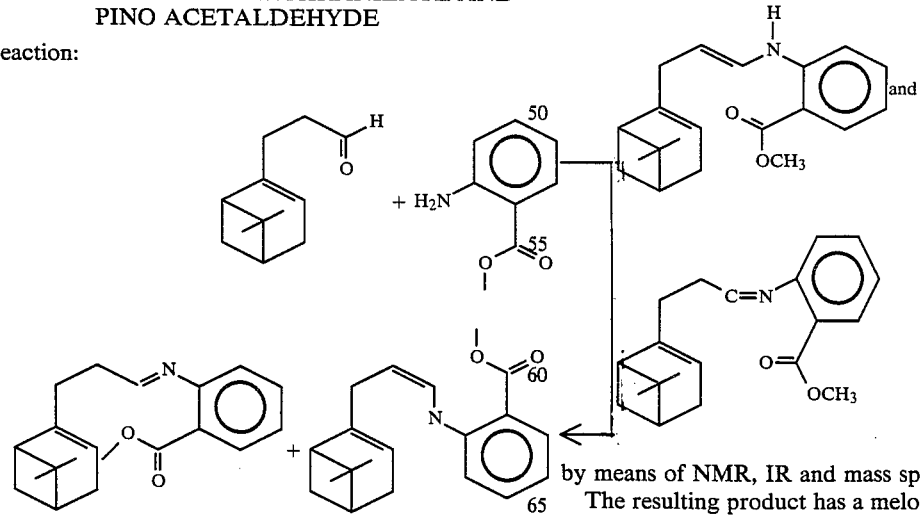

by means of NMR, IR and mass spectral analyses.

The resulting product has a melony and floral aroma profile.

FIG. 5 is the GLC profile for the crude reaction product. The peak indicated by reference numeral 501 is the peak for the methyl anthranilate reactant having the structure:

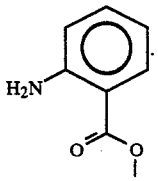

The peak indicated by reference numeral 502 is the peak for pino acetaldehyde having the structure.

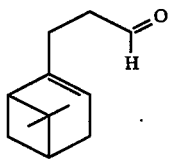

The peaks indicated by reference numerals 503, 504, 505 and 506 are for the schiff base reaction products and isomers thereof having the structures:

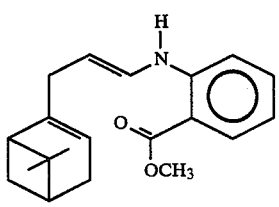

and

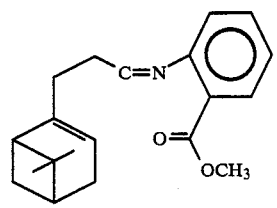

(Conditions: OV-1 fused silica column (50 m×0.32 mm) programmed at 60°-220° C. at 4° C. per minute).

FIG. 6 is the NMR spectrum for the compound having the structure:

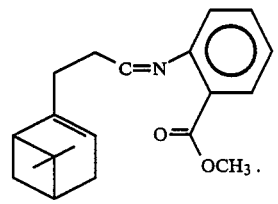

FIG. 7 is the NMR spectrum for the compound having the structure:

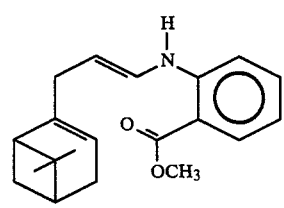

The resulting schiff base reaction product has an intense melony and floral aroma profile.

EXAMPLE IV

PREPARATION OF SCHIFF BASE REACTION PRODUCT OF PINO ACETALDEHYDE, HYDROXYCITRONELLAL AND METHYL ANTHRANILATE

Reaction:

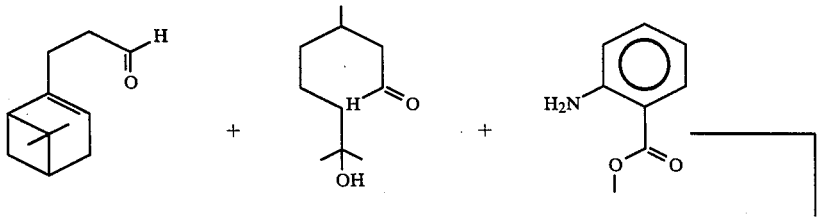

-continued

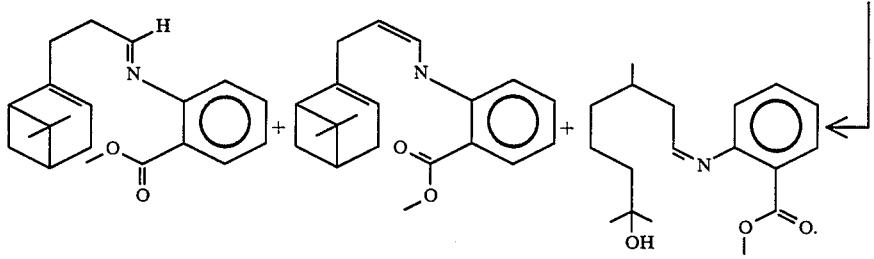

EXAMPLE IV(A) . . . Mole Ratio of Pino Acetaldehyde:Hydroxycitronellal:Methyl Anthranilate=1:2:3.

Into a 2 liter, 3 neck reaction flask equipped with mechanical stirrer, pot thermometer, glass "Y" adapter, one liter addition funnel, steam distillation head with a 45/50 bottom male joint attached to the reaction flask, head thermometer, curved fraction cutter with a 50 ml receiver, heating mantle controlled with a "Therm-O-Watch", dry ice trap, Bennert Manometer, vacuum bleed valve and vacuum pump is added 453.0 grams of methyl anthranilate (3.0 moles).

With stirring from the one liter addition funnel a mixture of 168.0 grams of pino acetaldehyde having the structure:

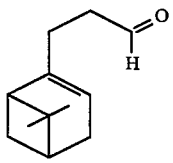

(1.0 moles) and 344.0 grams of hydroxycitronellal having the structure:

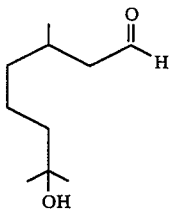

(2.0 moles) is added dropwise over an one hour period while slowly heating the reaction flask to 50° C.

The one liter addition funnel is then removed from the reaction flask.

50 mm/Hg. vacuum is then applied to the system.

With stirring the reaction mass is then heated over an one hour period to 125° C. and maintained at 125° C. for a period of eight hours. During the eight hour period, water of reaction is continually removed from the reaction mass at a vapor temperature of 40°-45° C.

The reaction mass is then cooled to 50° C. and the product is then analyzed. The reaction product contains the compounds having the structures:

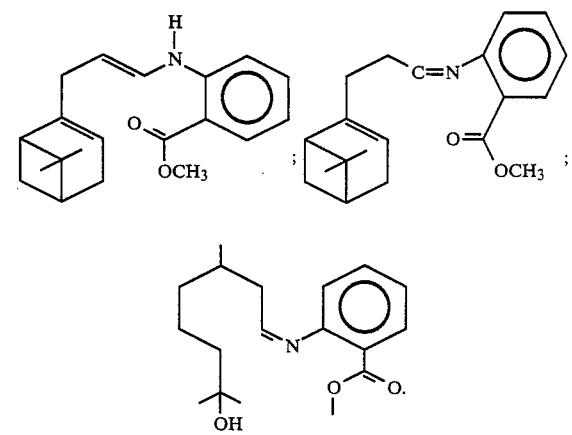

The resulting reaction product has an intense citrus, green and piney aroma profile with anisic, woody and floral undertones.

FIG. 8 is the GLC profile for the crude reaction product (Conditions: 50 m×0.32 mm OV-1 fused silica column, programmed at 60°-220° C. at 4° C. per minute).

The peak indicated by reference numeral 801 is the peak for hydroxycitronellal reactant having the structure:

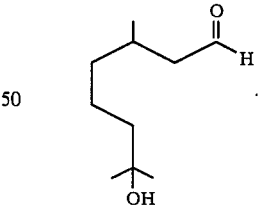

The peak indicated by reference numeral 802 is the peak for the methyl anthranilate reactant having the structure:

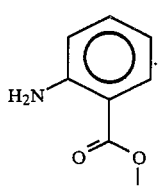

The peak indicated by reference numeral 803 is the peak for the pino acetaldehyde reactant having the structure:

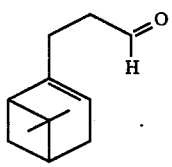

The peaks indicated by reference numerals 804, 805, 806 and 807 are the peaks for the schiff base reaction products having the structures:

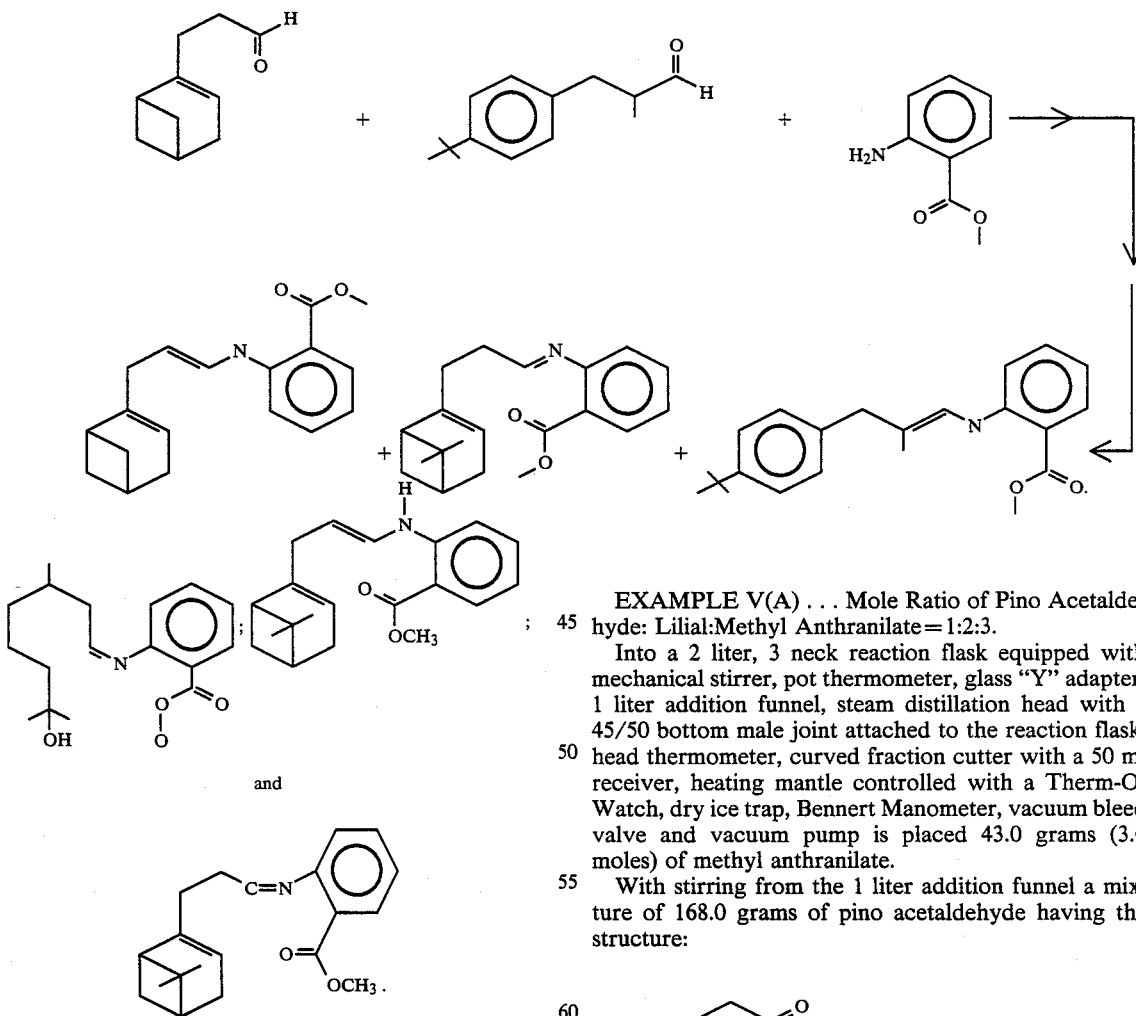

and

EXAMPLE IV(B) . . . Reaction Using a 1:1:2 Mole Ratio of Pino Acetaldehyde: Hydroxycitronellal:-Methyl Anthranilate.

Into a 2 liter reaction flask equipped with thermometer, 43dition funnel, mechanical stirrer, rushover head with fraction cutter and vacuum setup are placed 227 grams (1.5 moles) of methyl anthranilate. 129 Grams (2.75 moles) of hydroxy citronellal and 153 grams (2.7 moles) of pino acetaldehyde are then placed in the addition funnel. The resulting mixture is added to the reaction flask under atmospheric pressure over a 15 minute period.

The reaction mass is then heated to 50° C. After addition is complete the reaction mass is placed under a 50 mm/Hg. vacuum and heated to 125° C. The reaction mass is maintained at 125° C. for a period of six hours.

At the end of the six hour period, the reaction mass is cooled to room temperature and analyzed.

The resulting product has an intense, floral, ozoney, green and grape-like aroma profile.

EXAMPLE V

PREPARATION OF SCHIFF BASE REACTION PRODUCT OF LILIAL, PINO ACETALDEHYDE AND METHYL ANTHRANILATE

Reaction:

EXAMPLE V(A) . . . Mole Ratio of Pino Acetaldehyde: Lilial:Methyl Anthranilate=1:2:3.

Into a 2 liter, 3 neck reaction flask equipped with mechanical stirrer, pot thermometer, glass "Y" adapter, 1 liter addition funnel, steam distillation head with a 45/50 bottom male joint attached to the reaction flask, head thermometer, curved fraction cutter with a 50 ml receiver, heating mantle controlled with a Therm-O-Watch, dry ice trap, Bennert Manometer, vacuum bleed valve and vacuum pump is placed 43.0 grams (3.0 moles) of methyl anthranilate.

With stirring from the 1 liter addition funnel a mixture of 168.0 grams of pino acetaldehyde having the structure:

(1.0 moles) and 408.0 grams of lilial having the structure:

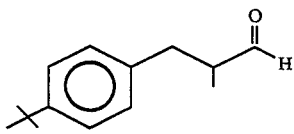

(2.0 moles) is added dropwise over a one hour period into the reaction mass while slowly heating the reaction mass to 50° C.

At the end of the additon, the 1 liter addition funnel is removed from the reaction flask.

Vacuum in an amount of 50 mm/Hg. is applied to the system.

With stirring, the reaction mass is gradually heated over a one hour period to 125° C.

The reaction mass is heated with stirring at 125° C. for a period of eight hours.

During the eight hour period, water of reaction is removed at a vapor temperature of 40°–45° C.

The reaction mass is cooled to 50° C.

Analysis using NMR, IR and mass spectral analyses yield the information that the reaction product contains the compounds having the structures:

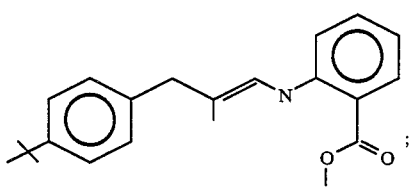

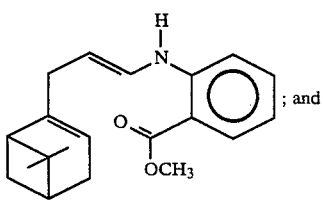
; and

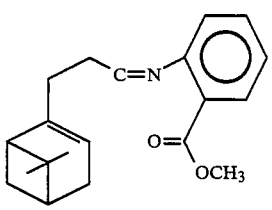

The resulting reaction product has an intense, floral and grape-like aroma profile with green and citrus undertones.

FIG. 9 is the GLC profile for the crude reaction product (Conditions: 50 m×0.32 mm OV-1 fused silica column, programmed at 60°–220° C. at 4° C. per minute). The peak indicated by reference numeral 901 is the peak for the methyl anthranilate reactant having the structure:

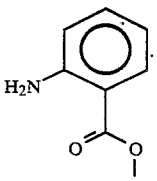

The peak indicated by reference numeral 902 is the peak for pino acetaldehyde reactant having the structure:

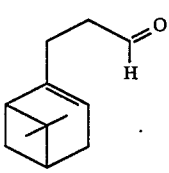

The peak indicated by reference numeral 903 is for lilial having the structure:

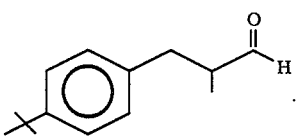

The peaks indicated by reference numerals 904, 905, 906, 907, 908 and 909 are for the schiff base reaction products and isomers thereof having the structures:

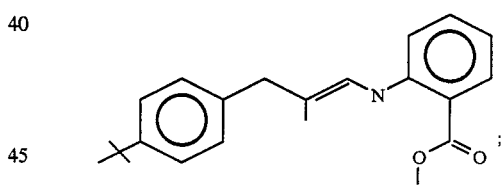
;

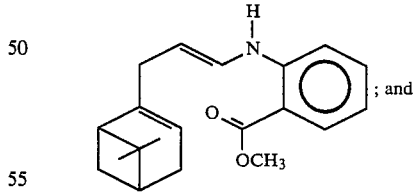
; and

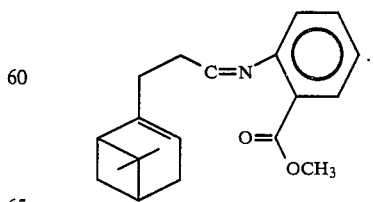

FIG. 10 is the NMR spectrum for the schiff base reaction products having the structure:

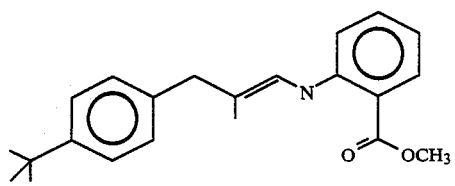

(E and Z isomers).

FIG. 11 is another NWR spectrum of the E and Z isomers of the schiff base reaction product having the structure:

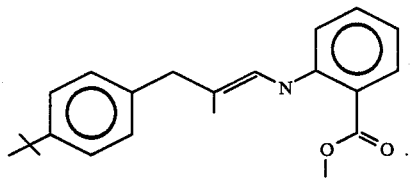

EXAMPLE V(B) . . . Mole Ratio of Lilial:Pino Acetaldehyde: Methyl Anthranilate=1:1:2.

Into a 2 liter reaction vessel equipped with stirrer, thermometer and vacuum pump setup and addition funnel is placed 227 grams (1.5 moles) of methyl anthranilate having the structure:

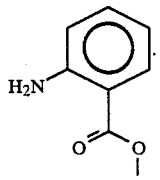

153 Grams (0.7 moles) of lilial having the structure:

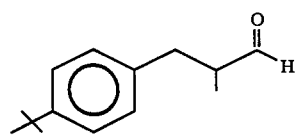

and 134 grams (0.75 moles) of pino acetaldehyde having the structure:

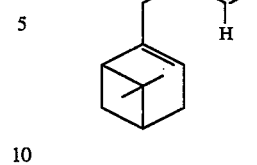

are then added from the addition funnel over a 15 minute period at atmospheric pressure.

The system is then put under 50 mm/Hg. vacuum and heated to 125° C. The system is maintained at 125° C. and 50 mm/Hg. vacuum over a period of eight hours.

At the end of the eight period, the reaction mass is cooled to 50° C.

The resulting product has a woody, piney and grape-like aroma profile with fresh cut wood and ozoney topnotes.

NMR, IR and mass spectral analyses yield the information that the resulting reaction products have the structures:

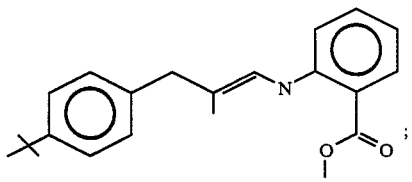

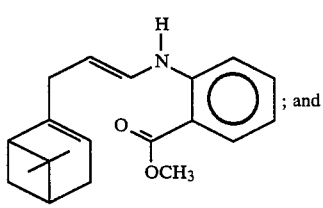

; and

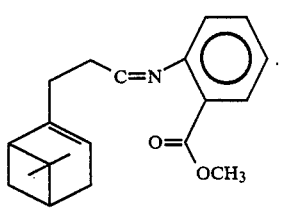

EXAMPLE VI

PREPARATION OF SCHIFF BASE OF PINO ACETALDEHYDE, LYRAL AND METHYL ANTHRANILATE

Reaction:

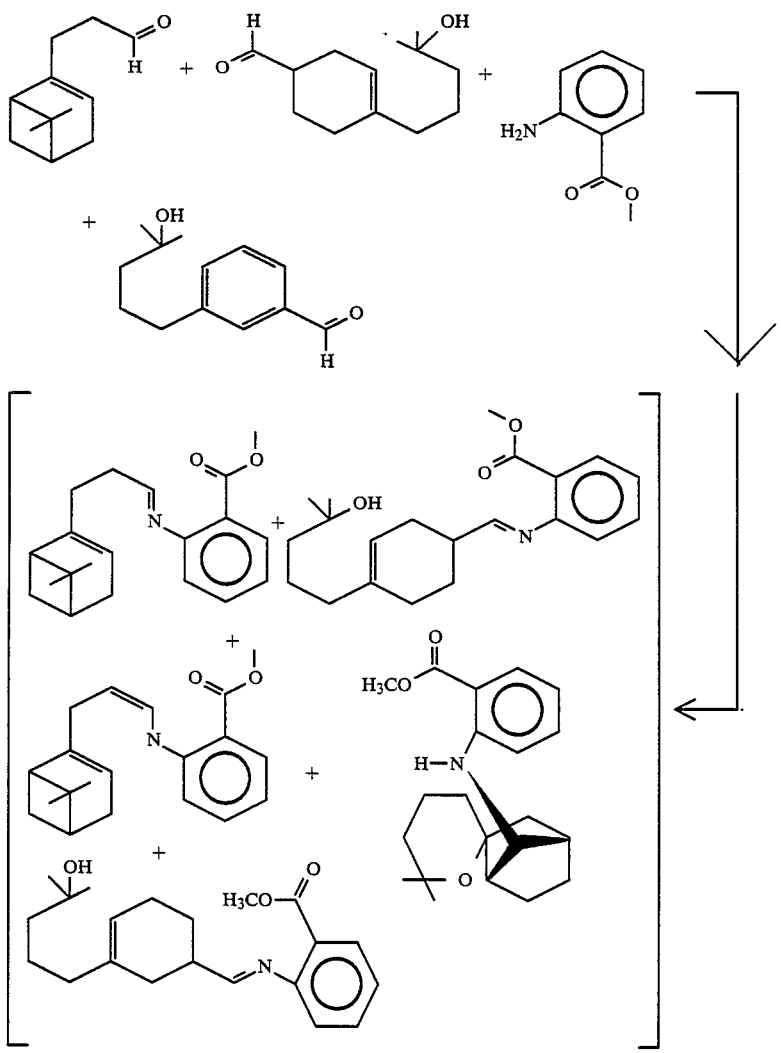

EXAMPLE VI(A) . . . Mole Ratio of Pino Acetaldehyde: Lyral:Methyl Anthranilate=1:2:3.

Into a 2 liter, 3 neck reaction flask equipped with mechanical stirrer, pot thermometer, glass "Y" adapter, one liter addition funnel, steam distillation head with a 45/50 bottom male joint attached to the reaction flask, head thermometer, curved fraction cutter with a 50 ml receiver, heating mantle controlled with a "Thermo-O-Watch", dry ice trap, Bennert Manometer, vacuum bleed valve and vacuum pump is placed 453.0 grams (3 moles) of methyl anthranilate having the structure:

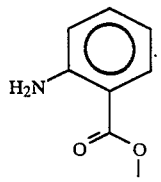

With stirring, from the one liter addition funnel, a mixture of 168.0 grams (1.0 moles) of pino acetaldehyde having the structure:

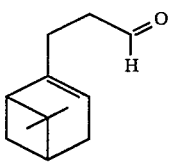

and 420.0 grams of lyral (2.0 moles), a mixture of compounds having the structures:

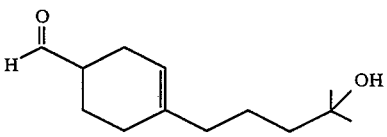

and

-continued

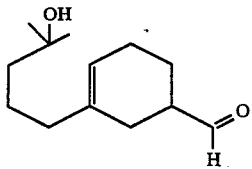

is added dropwise to the reaction mass over a period of one hour while slowly heating the reaction mass to a temperature of 50° C.

After the addition of the mixture of pino acetaldehyde and lyral, the addition funnel is removed from the reaction flask.

A vacuum of 50 mm/Hg. is then applied to the system.

With stirring, while maintaining the vacuum at 50 mm/Hg. the reaction mass is heated over a one hour period to 125° C.

The reaction mass is continued to be heated at 125° C. and 50 mm/Hg. vacuum for a period of eight hours while removing water of reaction at a vapor temperature of 40°–45° C.

The reaction mass is then cooled to 50° C. and analyzed

The resulting reaction product has an intense citrus, green and floral aroma profile with fresh air and ozoney topnotes.

NMR, IR and mass spectral analyses yield the information that the resulting reaction mass contains the compounds having the structures:

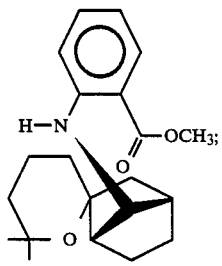

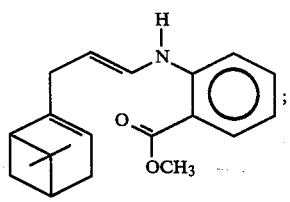

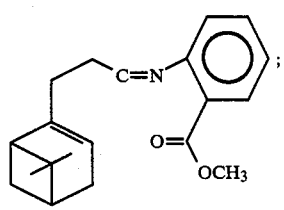

-continued

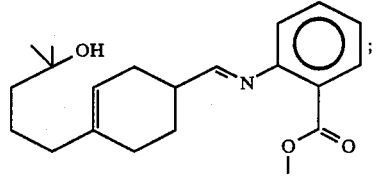

and

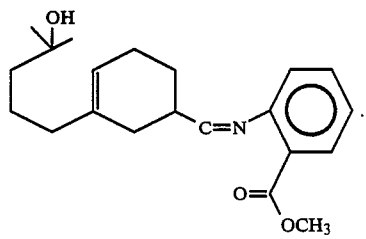

FIG. 12 is the GLC profile for the crude reaction product (Conditions: 50 m×0.32 mm OV-1 fused silica column, programmed at 60°–220° C. at 4° C. per minute).

The peak indicated by reference numeral 1201 is the peak for the methyl anthranilate reactant having the structure:

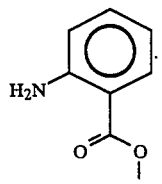

The peak indicated by reference numeral 1202 is the peak for pino acetaldehyde having the structure:

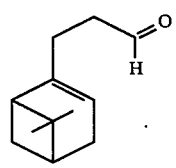

The peak indicated by reference numeral 1203 and reference numeral 1204 are peaks for the lyral isomers having the structures:

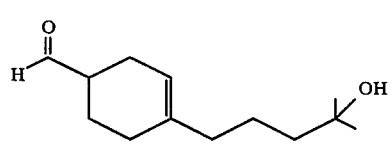

and

-continued

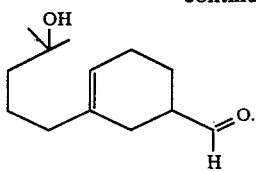

The peaks indicated by reference numerals 1205, 1206, 1207 and 1208 are for the schiff base reaction products having the structures:

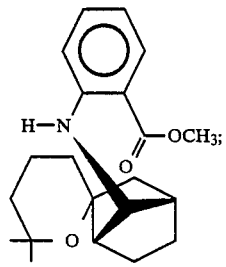

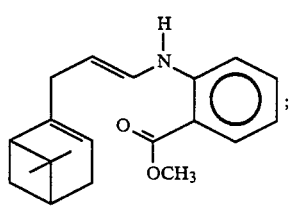

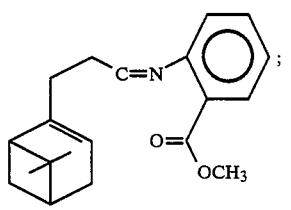

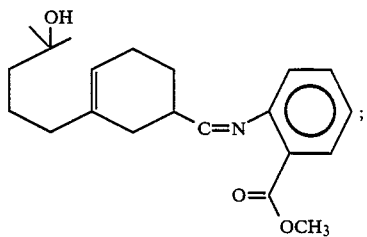

and

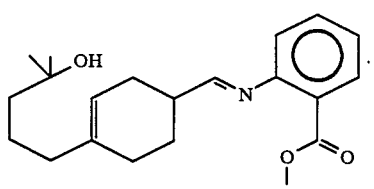

EXAMPLE VI(B) . . . Mole Ratio of Pino Acetaldehyde:Lyral:Methyl Anthranilate=1:1:2.

Into a 500 ml reaction flask equipped with stirrer, thermometer, heating mantle, addition funnel and vacuum pump are placed 28.2 grams (0.15 moles) of pino acetaldehyde having the structure:

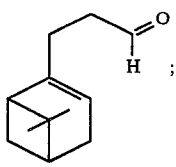

31.5 grams (0.15 moles) of lyral, a mixture of isomers having the structures:

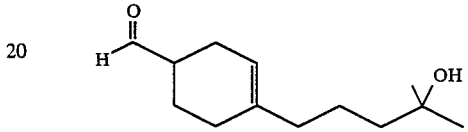

and

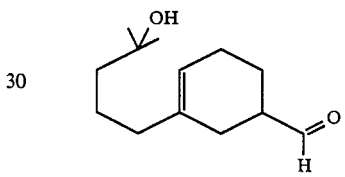

and 50 grams (0.33 moles) of methyl anthranilate having the structure:

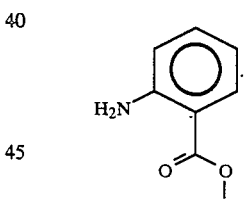

The reaction mass is put under 50 mm/Hg. vacuum and heated to 90° C. and maintained at that temperature and pressure for a period of ten hours.

At the end of the ten hour period, the reaction mass is cooled to 50° C.

The resulting reaction product has a sweet, citrus, green and melony aroma with ozoney and floral topnotes.

FIG. 13 is the GLC profile for the crude reaction product (Conditions: 3'×0.125" 10% SE-30 column programmed at 6° C. per minute). The peak indicated by reference numeral 1303 is the peak for a mixture of compounds having more than 50% of a compound having the structure:

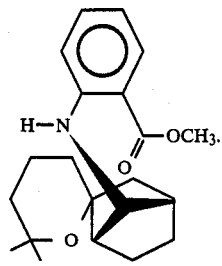

The peaks indicated by reference numerals 1301 and 1302 are peaks for mixtures of schiff base reaction products having the structures:

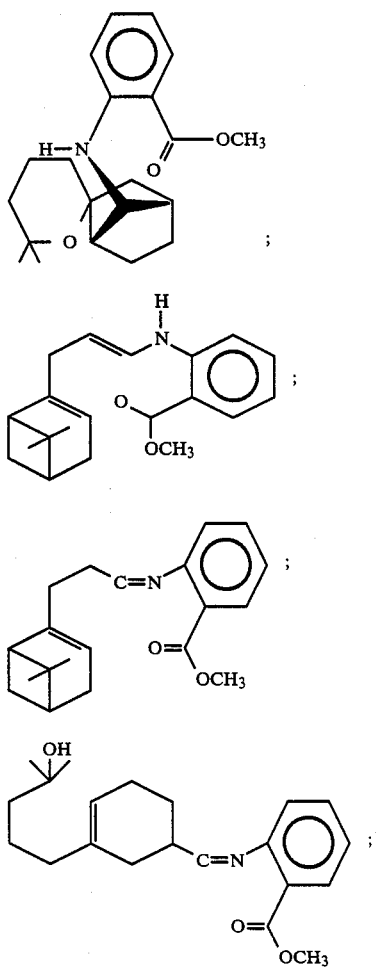

and

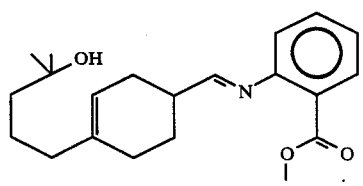

FIG. 14 is the NMR spectrum for the peak indicated by reference numeral 1303 on FIG. 13; that is, the NMR for a mixture of compounds containing more than 50% of the compound having the structure:

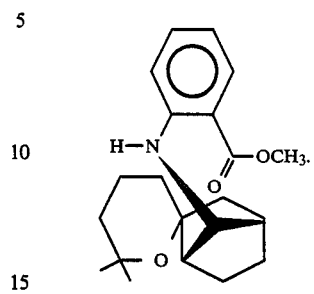

FIG. 15 is the NMR spectrum for the mixture of compounds indicated by reference numeral 1301 on the GLC profile of FIG. 13 containing a mixture of compounds having the structures:

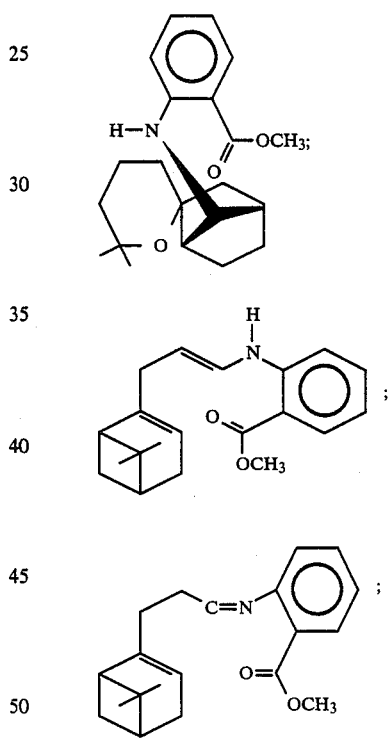

and

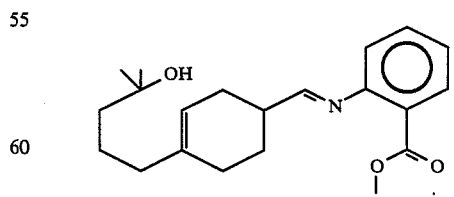

FIG. 16 is the NWR spectrum for the mixture of compounds of the peak indicated by reference numeral 1302 on FIG. 13; for a mixture of compounds having the structures:

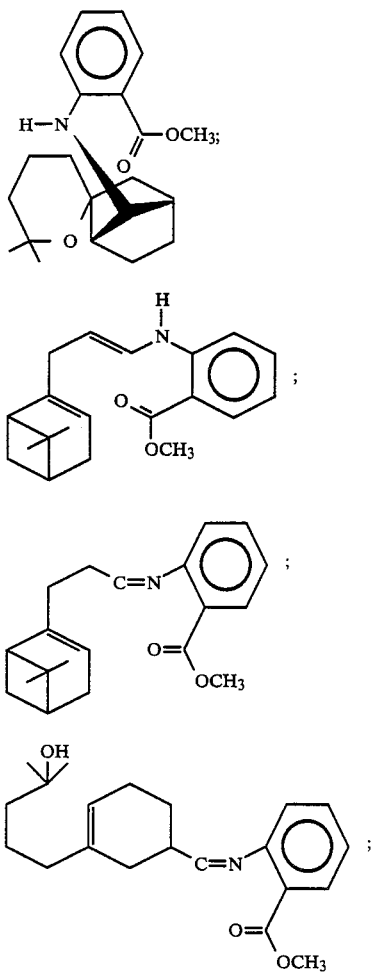

and

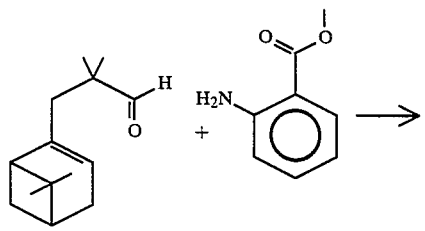

EXAMPLE VII

PREPARATION OF THE SCHIFF BASE OF METHYL ANTHRANILATE AND PINO ISOBUTYLALDEHYDE

Reaction:

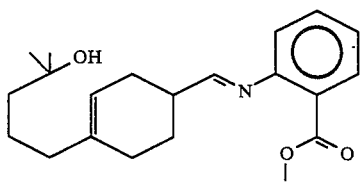

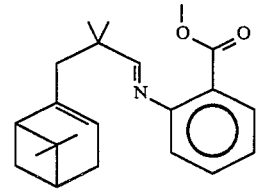

Into a 2 liter, 3 neck reaction flask equipped with mechanical stirrer, pot thermometer, glass "Y" adapter, one liter addition funnel, steam distillation head with a 40/50 bottom male joint attached to the reaction flask, head thermometer, curved fraction cutter with a 50 ml receiver, heating mantle controlled with a "Therm-O-Watch", dry ice trap, Bennert Manometer, vacuum bleed and vacuum pump is placed 302.0 grams (2.0 moles) of methyl anthranilate having the structure:

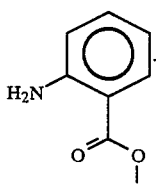

With stirring via the 1 liter addition funnel 412.0 grams (2.0 moles) of alpha-pino isobutylaldehyde having the structure:

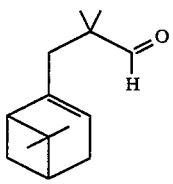

is added dropwise over a one hour period while slowly heating the reaction mass to 50° C.

When the addition is complete the one liter addition funnel is removed from the reaction system.

50 mm/Hg. Vacuum is applied to the reaction system.

With stirring while maintaining the 50 mm vacuum in the system, the reaction mass is heated to 115° C. over a period of 45 minutes.

The reaction mass is maintained at 115° C. and 50 mm/Hg. vacuum for a period of seven hours while removing water of reaction at a vapor temperature of 35°–45° C.

At the end of the seven hour reaction period, the reaction mass is cooled to 50° C.

The reaction mass is analyzed and determined by NWR, IR and mass spectral analyses to contain the compound having the structure:

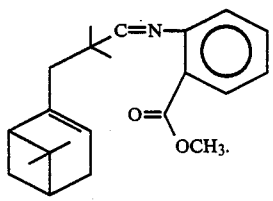

The reaction product has an interesting fresh and green aroma of high intensity and high substantivity.

FIG. 17 is the GLC profile for the crude reaction product (Conditions: 3'×0.125" 10% SE-30 column).

FIG. 18 is the NMR spectrum for the compound having the structure:

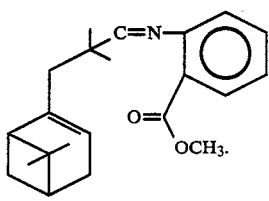

EXAMPLE VIII

PREPARATION OF SCHIFF BASE OF MELONAL AND METHYL ANTHRANILATE

Reaction:

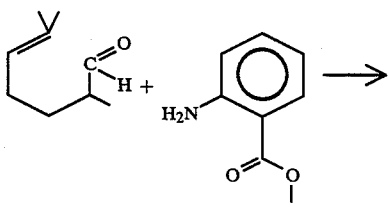

Into a 2 liter reaction flask equipped with addition funnel, thermometer, heating mantle, vacuum apparatus and stirrer are placed 302 grams (2.0 moles) of methyl anthranilate having the structure:

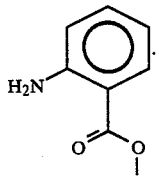

280 Grams of melonal (2 moles) having the structure:

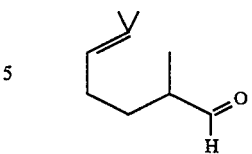

are placed into the addition funnel. The melonal is added dropwise from the addition funnel into the methyl anthranilate and the methyl anthranilate-melonal reaction mixture is heated to 50° C. at atmospheric pressure. When all of the melonal is added to the reaction mass, the reaction mass is put under a 50 mm/Hg. vacuum and is heated to 125° C. The reaction mass is maintained at 125° C. and 50 mm/Hg. vacuum for a period of seven hours.

At the end of the seven hour period, the reaction mass is cooled to 50° C. NMR, IR and mass spectral analyses yield the information that the reaction product has the structure:

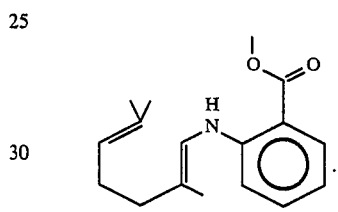

The resulting product has an intense and substantive muguet, fruity, green, melony and grape-like aroma profile with orange flower topnotes.

FIG. 22 is the GLC profile for the crude reaction product. The peaks indicated by reference numerals 2201 and 2202 are for the isomers of the compound having the structure:

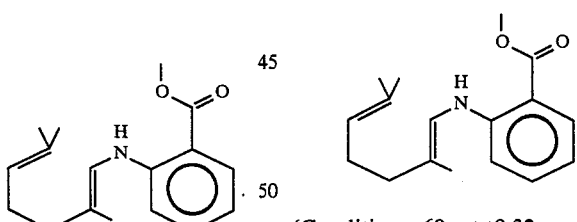

(Conditions: 60 m×0.32 mm OV-1 fused silica column, programmed at 60°–220° C. at 4° C. per-minute).

FIG. 23 is the GLC profile for the distillation product of the reaction product of Example VIII containing the compound having the structure:

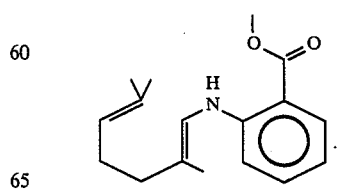

FIG. 24 is the NMR spectrum for the compound having the structure:

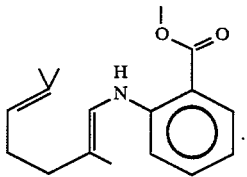

The crude reaction product is distilled on a one foot silver mirrored column yielding the following fractions:

| Fraction No. | Vapor Temp. (0° C.) | Liquid Temp. (0° C.) | Vacuum mm/Hg. Pressure | Weight of Fraction |
|---|---|---|---|---|
| 1 | 32/30 | 85/102 | 4/4 | 32.76 |
| 2 | 70 | 118 | 4.0 | 9.51 |
| 3 | 65 | 159 | 4.0 | 61.15 |
| 4 | 128 | 177 | 4.0 | 11.51 |
| 5 | 131 | 180 | 4.0 | 38.87 |
| 6 | 130 | 178 | 4.0 | 39.68 |
| 7 | 127 | 178 | 4.0 | 38.18 |
| 8 | 131/131 | 179/179 | 4.4 | 42.30 |
| 9 | 187 | 80 | 4.0 | 61.51 |
| 10 | 147 | 187 | 4.0 | 39.87 |
| 11 | 146 | 210 | 4.0 | 57.42 |
| 12 | 145 | 230 | 4.0 | 19.37 |

EXAMPLE IX

PREPARATION OF SCHIFF BASE OF CANTHOXAL AND METHYL ANTHRANILATE

Reaction:

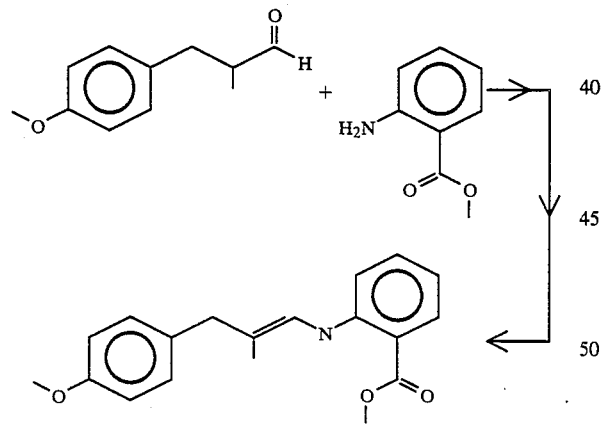

Into a 500 ml reaction flask equipped with stirrer, thermometer, vacuum apparatus and heating mantle is placed 48 grams of canthoxal having the structure:

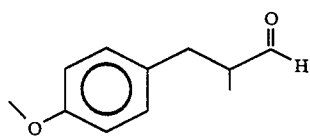

(0 25 moles) and 38 grams (0.25 moles) of methyl anthranilate. The resulting mixture exotherms and the reaction mass self-heats to 50° C.

The reaction mass is then heated to 100° C. and maintained at a temperature of 100° C. for a period of 6.5 hours.

At the end of the 6.5 hour period, the reaction mass is cooled to 50° C. and 80 grams of the reaction product having the structure:

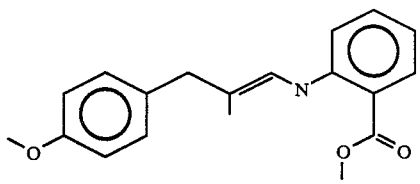

is recovered. The resulting product has an intense and substantive sweet, floral, fruity and ozoney aroma profile with anisic topnotes.

The resulting product also has an intense and aesthetically pleasing grape flavor at the level of 0.1 ppm causing it to be useful in grape and mandarin flavors.

A mixture of the reaction product of Example I and the reaction product of Example IX gives rise to an excellent intense grape flavor with lemon nuances which give rise to a very "natural-like" aroma and taste profile.

FIG. 25 is the GLC profile of the crude reaction product (Conditions: 2'×0.125" 5% SE-30 column programmed at 230° C. isothermal). The peak indicated by reference numeral 2501 is the peak for the compound having the structure:

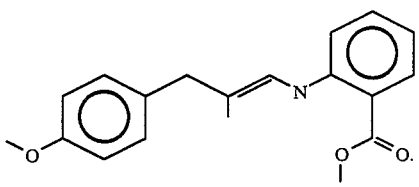

FIG. 26 is the NMR spectrum for the compound having the structure:

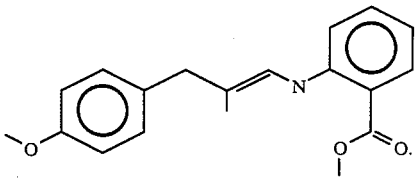

EXAMPLE X

FLORAL PERFUME COMPOSITIONS

The schiff bases of methyl anthranilate with Bergamal (produced according to Example I), floralozone (produced according to Example II) and pino acetaldehyde (produced according to Example III) have lemony, floral, green, ozoney and melony aromas with anisic topnotes. These materials have great warmth and richness and blend well with many floral concepts. Each of the schiff bases have rather unique floral notes of great value to perfumery. They may be demonstrated by the following floral fragrance whereby the schiff bases of Examples I, II and III are used to the extent of 5% by weight.

All three of these products perform quite well in fragrances and are judged to be very valuable fragrance materials:

TABLE II

| | FLORAL FRAGRANCE | | |
|---|---|---|---|
| | "A" | "B" | "C" |
| Citronellol | 12.3 | 12.3 | 12.3 |
| Geraniol | 2.5 | 2.5 | 2.5 |
| Amyl Cinnamic Aldehyde | 24.6 | 24.6 | 24.6 |
| Galaxolide ® 50 (Trademark for the Tricyclic Isochroman of International Flavors & Fragrances Inc.) | 9.8 | 9.8 | 9.8 |
| Vertenex High Cis (Cis-t-Butylcyclohexenyl Acetate; Para Isomer) | 7.4 | 7.4 | 7.4 |
| Rose Oxide | 0.7 | 0.7 | 0.7 |
| Cinnamic Alcohol | 19.6 | 19.6 | 19.6 |
| Aldehyde C-11 (n-Undecylenic Aldehyde) | 0.5 | 0.5 | 0.5 |
| Aldehyde C-12 (n-Dodecyl Aldehyde in 10% solution in diethyl phthalate) | 0.5 | 0.5 | 0.5 |
| Citronellal (10% solution in diethyl phthalate) | 0.5 | 0.5 | 0.5 |
| Phenyl Ethyl Acetate | 2.5 | 2.5 | 2.5 |
| Ylang Oil | 1.2 | 1.2 | 1.2 |
| Indisan (Hydrogenated derivative of reaction product of Camphene and Resorcinol) | 3.7 | 3.7 | 3.7 |
| Musk Ketone | 5.0 | 5.0 | 5.0 |
| Oakmoss Resin | 0.5 | 0.5 | 0.5 |
| Liatrix Absolute (10% in diethyl phthalate) | 2.5 | 2.5 | 2.5 |
| Vetiver Acetate | 1.2 | 1.2 | 1.2 |
| Diethyl Phthalate | 5.0 | 5.0 | 5.0 |
| The schiff base of the reaction product of Bergamal and methyl anthranilate of Example I. | 5.0 | 0 | 0 |
| The Schiff base of floralozone and methyl anthranilate of Example II. | 0 | 5.0 | 0 |
| The schiff base of pino acetaldehyde and methyl anthranilate of Example III. | 0 | 0 | 5.0 |

The schiff base of Bergamal and methyl anthranilate of Example I imparts to this floral fragrance a lemony undertone. Accordingly, the fragrance can be described as "floral with a lemony undertone".

The schiff base of Floralozone and methyl anthranilate of Example II imparts to this floral formulation a green and ozoney undertone with anisic topnotes. Accordingly, the fragrance thus produced can be described as "floral with ozoney and green undertones and anisic topnotes".

The schiff base of pino acetaldehyde and methyl anthranilate of Example III imparts to this floral formulation a melony undertone. Accordingly, the fragrance thus produced can be described as "floral with melony undertones".

EXAMPLE XI

FLORAL PERFUME COMPOSITIONS

The schiff base reaction product of pino acetaldehyde, hydroxycitronellal and methyl anthranilate with the mole ratio of pino acetaldehyde:hydroxycitronellal:methyl anthranilate being 1:2:3 produced according to Example IV(A) has a citrus, green and piney aroma with anisic, woody and floral undertones. The schiff base reaction product of pino acetaldehyde, hydroxycitronellal and methyl anthranilate with the mole ratio of pino acetaldehyde:hydroxycitronellal:methylanthranilate being 1:1:2 produced according to Example IV(B) has a floral, ozoney, green and grape-like aroma. The schiff base reaction product of pino acetaldehyde, lilial and methyl anthranilate produced according to Example V(A) with the mole ratio of pino acetaldehyde:lilial:methyl anthranilate being 1:2:3 has a floral and grape-like aroma with green and citrus undertones. The schiff base reaction product of pino acetaldehyde, lilial and methyl anthranilate with the mole ratio of pino acetaldehyde:lilial:methyl anthranilate being 1:1:2 has a woody, piney and grape-like aroma with fresh cut wood and ozoney topnotes. Each of these materials of Examples IV(A), IV(B), V(A) and V(B) have great warmth and richness and blend well with many floral concepts. They have rather unique floral notes of great value to perfumery.

All four of these products perform quite well in fragrances and are judged to be very valuable fragrance materials.

TABLE III

| | FLORAL FRAGRANCE | | | |
|---|---|---|---|---|
| | XI(A) | XI(B) | XI(C) | XI(D) |
| Citronellol | 12.3 | 12.3 | 12.3 | 12.3 |
| Geraniol | 2.5 | 2.5 | 2.5 | 2.5 |
| Amyl Cinnamic Aldehyde | 24.6 | 24.6 | 24.6 | 24.6 |
| Galaxolide ® 50 (Trademark for the Tricyclic Isochroman of International Flavors & Fragrances Inc.) | 9.8 | 9.8 | 9.8 | 9.8 |
| Vertenex High Cis (Cis-t-Butylcyclohexenyl Acetate; Para Isomer) | 7.4 | 7.4 | 7.4 | 7.4 |
| Rose Oxide | 0.7 | 0.7 | 0.7 | 0.7 |
| Cinnamic Alcohol | 19.6 | 19.6 | 19.6 | 19.6 |
| Aldehyde C-11 (n-Undecylenic Aldehyde) | 0.5 | 0.5 | 0.5 | 0.5 |
| Aldehyde C-12 (n-Dodecyl Aldehyde in 10% solution in diethyl phthalate) | 0.5 | 0.5 | 0.5 | 0.5 |
| Citronellal (10% solution in diethyl phthalate) | 0.5 | 0.5 | 0.5 | 0.5 |
| Phenyl Ethyl Acetate | 2.5 | 2.5 | 2.5 | 2.5 |
| Ylang Oil | 1.2 | 1.2 | 1.2 | 1.2 |
| Indisan (Hydrogenated derivative of reaction product of Camphene and Resorcinol) | 3.7 | 3.7 | 3.7 | 3.7 |
| Musk Ketone | 5.0 | 5.0 | 5.0 | 5.0 |
| Oakmoss Resin | 0.5 | 0.5 | 0.5 | 0.5 |
| Liatrix Absolute (10% in diethyl phthalate) | 2.5 | 2.5 | 2.5 | 2.5 |
| Vetiver Acetate | 1.2 | 1.2 | 1.2 | 1.2 |
| Diethyl Phthalate | 5.0 | 5.0 | 5.0 | 5.0 |
| Schiff base reaction product of pino acetaldehyde, hydroxycitronellal and methyl anthranilate with the mole ratio of pino acetaldehyde:hydroxycitronellal:methyl anthranilate being 1:2:3 of Example IV(A). | 5.0 | 0 | 0 | 0 |
| Schiff base reaction product of pino acetaldehyde, hydroxycitronellal and methyl anthranilate with the mole ratio of pino | | | | |

TABLE III-continued

| | FLORAL FRAGRANCE | | | |
|---|---|---|---|---|
| | XI(A) | XI(B) | XI(C) | XI(D) |
| acetaldehyde:hydroxy-citronellal:methyl anthranilate being 1:1:2. | 0 | 5.0 | 0 | 0 |
| Schiff base reaction product of pino acetaldehyde, lilial and methyl anthranilate of Example V(A) with the mole ratio of pino acetaldehyde:lilial:methyl anthranilate being 1:2:3. | 0 | 0 | 5.0 | 0 |
| Schiff base reaction product of pino acetaldehyde, lilial and methyl anthranilate of Example V(B) with the mole ratio of pino acetaldehyde:lilial:methyl anthranilate being 1:1:2. | 0 | 0 | 0 | 5.0 |

The schiff base reaction product of pino acetaldehyde, hydroxycitronellal and methyl anthranilate with the mole ratio of pino acetaldehyde:hydroxycitronellal:methyl anthranilate of 1:2:3 imparts to this floral fragrance a citrus, green and piney topnotes with anisic and woody undertones. Accordingly, the fragrance can be described as "floral with citrus, green and piney topnotes and anisic and woody undertones".

The schiff base reaction product of pino acetaldehyde, hydroxycitronellal and methyl anthranilate with the mole ratio of pino acetaldehyde:hydroxycitronellal:methyl anthranilate being 1:1:2 produced according to Example IV(B) imparts to this floral formulation a very ozoney, green and grape-like nuance. The ozoney, green and grape-like nuances appear as undertones. Accordingly, the fragrance thus produced can be described as "floral with ozoney, green and grape-like undertones".

The schiff base reaction product of pino acetaldehyde, lilial and methyl anthranilate with the mole ratio of pino acetaldehyde:lilial:methyl anthranilate of Example V(A) being 1:2:3 imparts to this floral formulation a grape-like topnote with green and citrus undertones. Accordigly, the fragrance can be described as "floral with grape-like topnotes and green and citrus undertones".

The schiff base reaction product of pino acetaldehyde, lilial and methyl anthranilate of Example V(B) with the mole ratio of pino acetaldehyde:lilial:methyl anthranilate being 1:1:2 imparts to this floral fragrance fresh cut wood and ozoney topnotes with woody, piney and grape undertones. Accordingly, the fragrance can be described as "floral with fresh cut wood and ozoney topnotes and woody, piney and grape-like undertones".

EXAMPLE XII

FLORAL PERFUME COMPOSITIONS

The schiff base reaction product of pino acetaldehyde, lyral and methyl anthranilate of Example VI(A) with the mole ratio of pino acetaldehyde:lyral:methyl anthranilate being 1:2:3 has a green, citrus and floral aroma with fresh air and ozoney topnotes. The schiff base reaction product of pino acetaldehyde, lyral and methyl anthranilate with the mole ratio of pino acetaldehyde:lyral:methyl anthranilate being 1:1:2 of Example VI(B) has a sweet, citrus, green and melony aroma profile with ozoney and floral topnotes.

The schiff base reaction product of pino isobutyraldehyde and methyl anthranilate of Example VII has a fresh, green aroma profile. Each of these materials has great warmth and richness and blends well with many floral concepts. They have rather unique floral notes of great value to perfumery.

All three of these products perform quite well in fragrances and are judged to be very valuable fragrance materials.

TABLE IV

| | FLORAL FRAGRANCE | | |
|---|---|---|---|
| | XI(A) | XI(B) | XI(C) |
| Citronellol | 12.3 | 12.3 | 12.3 |
| Geraniol | 2.5 | 2.5 | 2.5 |
| Amyl Cinnamic Aldehyde | 24.6 | 24.6 | 24.6 |
| Galaxolide ® 50 (Trademark for the Tricyclic Isochroman of International Flavors & Fragrances Inc.) | 9.8 | 9.8 | 9.8 |
| Vertenex High Cis (Cis-t-Butylcyclohexenyl Acetate; Para Isomer) | 7.4 | 7.4 | 7.4 |
| Rose Oxide | 0.7 | 0.7 | 0.7 |
| Cinnamic Alcohol | 19.6 | 19.6 | 19.6 |
| Aldehyde C-11 (n-Undecylenic Aldehyde) | 0.5 | 0.5 | 0.5 |
| Aldehyde C-12 (n-Dodecyl Aldehyde in 10% solution in diethyl phthalate | 0.5 | 0.5 | 0.5 |
| Citronellal (10% solution in diethyl phthalate) | 0.5 | 0.5 | 0.5 |
| Phenyl Ethyl Acetate | 2.5 | 2.5 | 2.5 |
| Ylang Oil | 1.2 | 1.2 | 1.2 |
| Indisan (Hydrogenated derivative of reaction product of Camphene and Resorcinol) | 3.7 | 3.7 | 3.7 |
| Musk Ketone | 5.0 | 5.0 | 5.0 |
| Oakmoss Resin | 0.5 | 0.5 | 0.5 |
| Liatrix Absolute (10% in diethyl phthalate) | 2.5 | 2.5 | 2.5 |
| Vetiver Acetate | 1.2 | 1.2 | 1.2 |
| Diethyl Phthalate | 5.0 | 5.0 | 5.0 |
| The schiff base reaction product of pino acetaldehyde, lyral and methyl anthranilate of Example IV(A) with the mole ratio of pino acetaldehyde:lyral:methyl anthranilate being 1:2:3. | 5.0 | 0 | 0 |
| The schiff base reaction product of pino acetaldehyde lyral and methyl anthranilate with the mole ratio of pino acetaldehyde:lyral:methyl anthranilate being 1:1:2 of Example VII(B). | 0 | 5.0 | 0 |
| The schiff base reaction product of pino isobutyraldehyde and methyl anthranilate of Example VII. | 0 | 0 | 5.0 |

The schiff base reaction product of pino acetaldehyde, lyral and methyl anthranilate with the mole ratio of pino acetaldehyde:lyral:methyl anthranilate being 1:2:3 of Example VI(A) imparts to this floral formulation green and citrus undertones with fresh air and ozoney topnotes. Accordingly, the fragrance can be described as "floral with fresh air and ozoney topnotes and green and citrus undertones".

The schiff base reaction product of pino acetaldehyde, lyral and methyl anthranilate of Example VI(B)

with the mole ratio of pino acetaldehyde:lyral:methyl anthranilate being 1:1:2 imparts to this floral fragrance ozoney topnotes with sweet, citrus, green and melony undertones. Accordingly, the fragrance can be described as "floral with ozoney topnotes and sweet, citrus, green and melony undertones".

The schiff base reaction product of pino isobutyraldehyde and methyl anthranilate produced according to Example VII imparts to this floral fragrance fresh, green undertones. Accordingly, the fragrance can be described as "floral with fresh, green undertones".

EXAMPLE XIII

FLORAL PERFUME COMPOSITIONS

The schiff base reaction product of melonal and methyl anthranilate produced according to Example VIII has a muguet, fruity, green, melony and grape-like aroma profile with orange flower topnotes. The schiff base reaction product of canthoxal and methyl anthranilate produced according to Example IX has a sweet, floral, fruity and ozoney aroma profile with anisic topnotes. These materials have great warmth and richness and blend well with many floral concepts. They are rather unique floral notes having great value to perfumery. Their use may be demonstrated by the following floral fragrances whereby each of the schiff base reaction products is used to the extent of 5% by weight.

These two products perform quite well and are judged to be very valuable fragrance materials.

TABLE V

| | FLORAL FRAGRANCE | |
|---|---|---|
| | XI(A) | XI(B) |
| Citronellol | 12.3 | 12.3 |
| Geraniol | 2.5 | 2.5 |
| Amyl Cinnamic Aldehyde | 24.6 | 24.6 |
| Galaxolide ® 50 (Trademark for the Tricyclic Isochroman of International Flavors & Fragrances Inc.) | 9.8 | 9.8 |
| Vertenex High Cis (Cis-t-Butylcyclohexenyl Acetate; Para Isomer) | 7.4 | 7.4 |
| Rose Oxide | 0.7 | 0.7 |
| Cinnamic Alcohol | 19.6 | 19.6 |
| Aldehyde C-11 (n-Undecylenic Aldehyde) | 0.5 | 0.5 |
| Aldehyde C-12 (n-Dodecyl Aldehyde in 10% solution in diethyl phthalate) | 0.5 | 0.5 |
| Citronellal (10% solution in diethyl phthalate) | 0.5 | 0.5 |
| Phenyl Ethyl Acetate | 2.5 | 2.5 |
| Ylang Oil | 1.2 | 1.2 |
| Indisan (Hydrogenated derivative of reaction product of Camphene and Resorcinol) | 3.7 | 3.7 |
| Musk Ketone | 5.0 | 5.0 |
| Oakmoss Resin | 0.5 | 0.5 |
| Liatrix Absolute (10% in diethyl phthalate) | 2.5 | 2.5 |
| Vetiver Acetate | 1.2 | 1.2 |
| Diethyl Phthalate | 5.0 | 5.0 |
| The schiff base reaction product of melonal and methyl anthranilate produced according to Example VIII. | 5.0 | 0 |
| The schiff base reaction product of canthoxal and methyl anthranilate produced according to Example IX. | 0 | 5.0 |

The schiff base reaction product of melonal and methyl anthranilate imparts to this floral fragrance orange flower topnotes with muguet, fruity, green, melony and grape-like undertones. Accordingly, the fragrance can be described as "floral with orange flower topnotes and muguet, fruity, green, melony and grape-like undertones".

The schiff base reaction product of canthoxal and methyl anthranilate imparts to this floral fragrance anisic topnotes with sweet, fruity and ozoney undertones. Accordingly, the fragrance can be described as "floral with anisic topnotes and sweet, fruity and ozoney undertones".

EXAMPLE XIV

PREPARATION OF COSMETIC POWDER COMPOSITIONS

Cosmetic powder compositions are prepared by mixing in a ball mill 100 grams of talcum powder with 0.25 grams of each of the substances set forth in Table VI below. Each of the cosmetic powder compositions has an excellent aroma as described in Table VI below:

TABLE VI

| Substance | Aroma Description |
|---|---|
| The schiff base reaction product of Example I of Bergamal and methyl anthranilate. | A lemony and floral aroma. |
| The schiff base reaction product of Floralozone and methyl anthranilate of Example II. | A green, floral and ozoney aroma profile with anisic topnotes. |
| The schiff base reaction product of pino acetaldehyde and methyl anthranilate produced according to Example III. | A melony and floral aroma profile. |
| The schiff base reaction product of pino acetaldehyde, hydroxycitronellal and methyl anthranilate of Example IV(A) with the mole ratio of pino acetaldehyde:hydroxycitronellal:methyl anthranilate being 1:2:3. | A citrus, green and piney aroma profile with anisic, woody and floral undertones. |
| The schiff base reaction product of pino acetaldehyde, hydroxycitronellal and methyl anthranilate of Example IV(B) with the mole ratio of pino acetaldehyde:hydroxycitronellal:methyl anthranilate being 1:1:2. | A floral, ozoney, green and grape-like aroma profile. |
| The schiff base reaction product of pino acetaldehyde, lilial and methyl anthranilate of Example V(A) with the mole ratio of pino acetaldehyde:lilial:methyl anthranilate being 1:2:3. | A floral and grape-like aroma profile with green and citrus undertones. |
| The schiff base reaction product of Example V(B) of pino acetaldehyde, lilial and methyl anthranilate with the mole ratio of pino acetaldehyde:lilial:methyl anthranilate being 1:1:2. | A woody, piney and grape-like aroma profile with fresh cut wood and ozoney topnotes. |
| The schiff base reaction product of pino acetaldehyde, lyral and methyl anthranilate of Example VI(A) with the mole ratio of pino acetaldehyde:lyral:methyl anthranilate being 1:2:3. | A green, citrus and floral aroma profile with fresh air and ozoney topnotes. |
| The schiff base reaction product of pino acetaldehyde, lyral and methyl anthranilate of Example VI(B) with the mole ratio of pino acetaldehyde:lyral:methyl anthranilate being 1:1:2. | A sweet, citrus, green and melony aroma profile with ozoney and floral topnotes. |
| The schiff base reaction product of pino isobutyraldehyde and methyl anthranilate produced according to Example VII. | A fresh and green aroma profile. |
| The schiff base reaction product of melonal and methyl anthranilate produced according to Example VIII | A muguet, fruity, green, melony and grape-like aroma profile with orange flower topnotes. |

TABLE VI-continued

| Substance | Aroma Description |
| --- | --- |
| The schiff base reaction product of canthoxal with methyl anthranilate produced according to Example IX. | A sweet, floral, fruity and ozoney aroma profile with anisic topnotes. |
| Fragrance produced according to Example X(A). | Floral with a lemony undertones. |
| Fragrance produced according to Example X(B). | Floral with ozoney and green undertones and anisic topnotes. |
| Fragrance produced according to Example X(C). | Floral with melony undertones. |
| Fragrance produced according to Example XI(A). | Floral with citrus, green and piney topnotes and anisic and woody undertones. |
| Fragrance produced according to Example XI(B). | Floral with ozoney, green and grape-like undertones. |
| Fragrance produced according to Example XI(C). | Floral with grape-like topnotes and green and citrus undertones. |
| Fragrance produced according to Example XI(D). | Floral with fresh cut wood and ozoney topnotes and woody, piney and grape-like undertones. |
| Fragrance produced according to Example XII(A). | Floral with fresh air and ozoney topnotes and green and citrus undertones. |
| Fragrance produced according to Example XII(B). | Floral with ozoney topnotes and sweet, citrus, green and melony undertones. |
| Fragrance produced according to Example XII(C). | Floral with fresh, green undertones. |
| Fragrance produced according to Example XIII(A). | Floral with orange flower topnotes and muguet, fruity, green, melony and grape-like undertones. |
| Fragrance produced according to Example XIII(B). | Floral with anisic topnotes and sweet, fruity and ozoney undertones. |

EXAMPLE XV

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table VI of Example XIV are prepared containing 0.10%, 0.15%, 0.20%, 0.25%, 0.30% and 0.35% of the substance set forth in Table VI of Example XIV. They are prepared by adding and homogeneously mixing the appropriate quantity of substance in Table VI of Example XIV in the liquid detergent. The detergents all possess excellent aromas as set forth in Table VI of Example XIV, the intensity increasing with greater concentrations of substance as set forth in Table VI of Example XIV.

EXAMPLE XVI

PREPARATION OF COLOGNES AND HANDKERCHIEF PERFUMES

Compositions as set forth in Table VI of Example XIV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table VI of Example XIV are imparted to the colognes and to the handkerchief perfumes at all levels indicated.

EXAMPLE XVII

PREPARATION OF SOAP COMPOSITIONS

One hundred grams of soap chips (per sample) (IVORY ®, produced by the Procter & Gamble Company of Cincinnati, Ohio), are each mixed with one gram sample of substances as set forth in Table VI of Example XIV until homogeneous compositions are obtained. In each of the cases, the homogeneous compositions are heated under 8 atmospheres pressure at 180° C. for a period of three hours and the resulting liquid are placed into soap molds. The resulting soap cakes, on cooling, manifest aromas as set forth in Table VI of Example XIV.

EXAMPLE XVIII

PREPARATION OF SOLID DETERGENT COMPOSITIONS

Detergents are prepared using the following ingredients according to Example I of Canadian Patent No. 1,007,948 (incorporated herein by reference):

| Ingredient | Percent by Weight |
| --- | --- |
| NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table VI of Example XIV. Each of the detergent samples has an excellent aroma as indicated in Table VI of Example XIV.

EXAMPLE XIX

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.);
   57% $C_{20-22}$ HAPS
   22% isopropyl alcohol
   20% antistatic agent
   1% of one of the substances as set forth in Table VI of Example XIV.

Fabric softening compositions prepared according to Example I a column 15 of U.S. Pat. No. 3,632,396 having aroma characteristics as set forth in Table VI of Example XIV, supra, consist of a substrate coating having a weight of about grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table VI of Example XIV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table VI of Example XIV, supra.

EXAMPLE XX

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| Ingredients | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table VI of Example XIV, supra. | 0.10 |

The perfume substances as set forth in Table VI of Example XIV add aroma characteristics as set forth in Table VI of Example XIV which are rather intense and aesthetically pleasing to the users of the soft-feel, good-hold pump hair sprays.

EXAMPLE XXI

CONDITIONING SHAMPOOS

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table VI of Example XIV is added to the mixture. The resulting mixture is cooled to 40° C. and blending is carried out for an additional one hour in each case. At the end of the blending period, the resulting material has a pleasant fragrance as indicated in Table VI of Example XIV.

EXAMPLE XXII

Each of the fragrance materials of Table VI of Example XIV, supra, are added to a 50:50 weight:weight mixture of low density polyethylene:polyepsilon caprolactone PCL-700 forming pellets with scents as set forth in Table VI of Example XIV, supra.

75 Pounds of a 50:50 mixture of PCL-700 polyepsilon caprolactone (manufactured by the Union Carbide Corporation of New York, N.Y. having a melting point of about 180°-190° F.):Low density polyethylene, are heated to about 250° F. in a container of the kind illustrated in FIGS. 20 and 21. 25 Pounds of each of the fragrance materials as set forth in Table VI of Example XIV, is then quickly added to the liquified polymer mixture, the lid 228 is put in place and the agitating means 273 are actuated. The temperature is then raised to about 260° F. and the mixing is continued for 5-15 minutes. The valve "V" is then opened to allow flow of the molten polymer enriched with perfume ingredient to exit through the orifices 234. The liquid falling through the orifices almost instantaneously upon impact with the moving cooled conveyor 238. Polymer beads or pellets 244 having pronounced scents as described in Table VI of Example XIV, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table VI of Example XIV, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table VI of Example XIV, supra.

EXAMPLE XXIII

CITRUS/GRAPE FLAVOR FORMULATIONS

The following citrus/grape flavor formulations are prepared:

| | Parts by Weight | | |
| --- | --- | --- | --- |
| Ingredients | "A" | "B" | "C" |
| The schiff base reaction product of canthoxal and methyl anthranilate produced according to Example IX. | 26.0 | 0 | 13.0 |
| The schiff base reaction product of Bergamal and methyl anthranilate produced according to Example I. | 0 | 26.0 | 13.0 |
| Natural Lemon Oil Terpeneless | 10.0 | 10.0 | 10.0 |
| Acetaldehyde | 0.6 | 0.6 | 0.6 |
| Alpha-Terpineol | 2.1 | 2.1 | 2.1 |
| Citral | 1.8 | 1.8 | 1.8 |
| Carvone | 0.24 | 0.24 | 0.24 |
| Terpinolene | 1.2 | 1.2 | 1.2 |
| Alpha-Terpinene | 0.25 | 0.25 | 0.25 |
| Diphenyl | 0.25 | 0.25 | 0.25 |
| Alpha-Fenchyl Alcohol | 0.25 | 0.25 | 0.25 |
| Limonene | 0.35 | 0.35 | 0.35 |

-continued

| Ingredients | Parts by Weight "A" | "B" | "C" |
|---|---|---|---|
| Linalool | 0.25 | 0.25 | 0.25 |
| Geranyl Acetate | 0.25 | 0.25 | 0.25 |
| Nootkatone | 0.25 | 0.25 | 0.25 |
| Neryl Acetate | 0.25 | 0.25 | 0.25 |
| Cyclohexyldisulfide | 2.5 | 0 | 2.5 |

The flavor formulation of Example "A" (hereinafter referred to as Example XXIII(A) has an intense citrusy and "natural" grape aroma and taste profile.

The flavor formulation of Example XXIII(B) has an intense citrusy "natural lemon" aroma and taste profile due to the presence of the schiff base of Bergamal and methyl anthranilate.

The flavor formulation of Example XXIII(C) has a "natural" grape and lemony aroma profile with the lemon nuances augmenting and enhancing the grape nuances and this is primarily due to the presence of the mixture of the schiff base reaction product of Bergamal and methyl anthranilate of Example I and of canthoxal and methyl anthranilate of Example IX.

EXAMPLE XXIV

A.

POWDER FLAVOR COMPOSITIONS

20 Grams of each of the flavor compositions of Examples XXIII(A), XXIII(B) and XXIII(C) containing schiff base reaction products of methyl anthranilate with Bergamal and/or canthoxal is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B.

SUSTAINED RELEASE FLAVORS

The following mixtures are prepared:

| Ingredients | Parts by Weight |
|---|---|
| Liquid Citrus Flavor Compositions of one of Examples XXIII(A), XXIII(B) or XXIII(C). | 20.0 |
| Propylene glycol | 9.0 |
| CAB-O-SIL ® M-5 Brand of Silica produced by the Cabot Corporation of 125 High Street, Boston, Massachusetts 02110: Physical Properties: | 5.00 |
| Surface area: 200 m$^2$/gm | |
| Nominal particle size: 0.012 microns | |
| Density: 2.3 lbs./cu.ft. | |

The Cab-O-Sil is dispersed in each of the liquid citrus flavor compositions of Examples XXIII(A), XXIII(B) and XXIII(C) with vigorous stirring, thereby resulting in a viscous liquid. 71 Parts by weight of each of the powder flavor compositions of Part A, supra, is then blended into the said viscous liquids, with stirring at 25° C. for a period of 30 minutes resulting in dry free flowing sustained release flavor powders.

EXAMPLE XXV

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of each of the liquid flavor compositions of Examples XXIII(A), XXIII(B) and XXIII(C) are separately added to the solution which is then homogenized to form an emulsion having particle size in the range of 5-40 microns. The material is kept at 120° F. under which conditions the gelatin will not gel.

Coacervation is induced by adding, slowly and uniformly 40 parts by weight of a 20% aqueous solution of sodium sulphate. During coacervation the gelatin molecules are deposited uniformly about each oil droplet as a nucleus.

Gelatin is effected by pouring the heated coacervate mixture into 1,000 parts by weight of 7% aqueous solution of sodium sulphate at 65° C. The resulting gelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XXVI

CHEWING GUMS

100 Parts by weight of chicle are mixed with 4 parts by weight of each of the flavors prepared in accordance with Example XXIV(B). 300 Parts of sucrose and 100 parts of corn syrup are added. Mixing is effected in a ribbon blender with jacketed side walls of the type manufactured by the Baker Perkins Company.

The resultant chewing gum is then manufactured into strips 1 inch in width and 0.1 inches in thickness. The strips are cut into lengths of 3 inches each. On chewing, the chewing gum has a pleasant, long lasting citrus flavor.

EXAMPLE XXVII

CHEWING GUMS

100 Parts by weight of chicle are mixed with 18 parts by weight of each of the flavors prepared in accordance with Example XXV. 300 Parts of sucrose and 100 parts of corn syrup are then added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gum has a pleasant, long lasting citrus flavor.

EXAMPLE XXVIII

TOOTHPASTE FORMULATIONS

The following separate groups of ingredients are prepared:

| Parts by Weight | Ingredients |
|---|---|
| Group "A" | |
| 30.200 | Glycerine |
| 15.325 | Distilled Water |
| .100 | Sodium Benzoate |

| Parts by Weight | Ingredients |
|---|---|
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N—Lauroyl Sarcosinate (foaming agent) |
| Group "D" | |
| 1.200 Example XXIV(B) | Each of the Flavor Materials of |

PROCEDURE

1. The ingredients in Group "A" are stirred and heated in a steam jacketed kettle to 160° F.;
2. Stirring is continued for an additional three to five minutes to form a homogeneous gel;
3. The powders of Group "B" are added to the gel, while mixing, until a homogeneous paste is formed;
4. With stirring, the flavor of "D" is added and lastly the sodium n-lauroyl sarcosinate;
5. The resultant slurry is then blended for one hour. The completed paste is then transferred to a three roller mill and then homogenized, and finally tubed.

The resulting toothpaste when used in a normal tooth brushing procedure yields a pleasant citrus flavor, of constant strong intensity throughout said procedure (1–1.5 minutes).

EXAMPLE XXIX

CHEWABLE VITAMIN TABLETS

Each of the flavor materials produced according to the process of Example XXIV(B) is added to a Chewable Vitamin Tablet Formulation at a rate of 10 gm/Kg which chewable vitamin tablet formulation is prepared as follows:

In a Hobart Mixer the following materials are blended to homogeneity:

| | Gms/1000 Tablets |
|---|---|
| Vitamin C (ascorbic acid) as ascorbic acid-sodium ascorbate mixture 1:1 | 70.00 |
| Vitamin $B_1$ (thiamine mononitrate) as ROCOAT ® thiamine mononitrate $33\frac{1}{3}\%$ (Hoffman La Roche) | 4.0 |
| Vitamin $B_2$ (riboflavin) as ROCOAT ® riboflavin $33\frac{1}{3}\%$ | 5.0 |
| Vitamin $B_6$ (pyridoxine hydrochloride) as ROCOAT ® pyridoxine hydrochloride $33\frac{1}{3}\%$ | 4.0 |
| Niacinamide as ROCOAT ® niacinamide $33\frac{1}{3}\%$ | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate $33\frac{1}{3}\%$ ROCHE ® | 6.6 |
| d-Biotin | 0.044 |
| Each of the flavor formulations of Example XXIV(B) | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 G dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong citrus flavor for a period of 12 minutes.

EXAMPLE XXX

CHEWING TOBACCO

Onto 100 pounds of tobacco for chewing (85% Wisconsin lead and 15% Pennsylvania leaf) the following casing is sprayed at a rate of 30%:

| Ingredients | Parts by Weight |
|---|---|
| Corn Syrup | 60.0 |
| Licorice | 10.0 |
| Glycerin | 20.0 |
| Fig Juice | 4.6 |
| Prune Juice | 5.0 |
| Each of the Flavor Materials of Example XXIV(B) | 0.4 |

The resultant product is redried to a moisture content of 20%. On chewing, this tobacco has an excellent substantially consistent, long-lasting citrus and licorice aroma and taste profile in conjunction with the tobacco note.

EXAMPLE XXXI

To 100 parts by weight of GOYA ® mango nectar (produced by the Goya Corporation of New York, N.Y.) is added 10 ppm of the schiff base reaction product of pino acetaldehyde and methyl anthranilate produced according to Example III. The resulting schiff base reaction product adds to the mango nectar a very natural nuance which although present in natural mango is lost in the canning process when mango nectar is prepared and canned in the usual manner.

EXAMPLE XXXII

A fabric washing deodorant detergent powder product is prepared by admixing the following ingredients:

| Ingredients | Parts by Weight |
|---|---|
| Linear alkylbenzene sulfonate | 9.0 |
| $C_{13}$–$C_{15}$ straight chain alcohols (30:30:40 mixture of $C_{13}$, $C_{14}$, and $C_{15}$ straight chain alcohol) | 4.0 |
| Sodium tripolyphosphate | 16.0 |
| ZEAOLIGHT | 8.0 |
| Sodium silicate | 4.0 |
| Magnesium silicate | 0.8 |
| Ethylene diamine | 0.6 |
| N,N,N',N'—[tetra(methylene phosphonic acid)] sodium carboxy methyl cellulose | 0.9 |
| Anti-foam | 1.5 |
| Sodium Perborate tetrahydrate | 14.0 |
| N,N,N',N'—Tetraacetyl Glycoluril | 4.2 |
| Schiff base reaction product of Bergamal and methyl anthranilate produced according to Example I. | 0.35 |
| Water | 45.0 |
| Sodium sulfate | 5.0 |

The resulting fabric washing deodorant detergent powder on use gives rise to a very pleasant "fresh air" aroma without any aesthetically displeasing aromas subsequent to washing of fabrics in the standard washing machine cycle.

When the foregoing composition is created wherein the Bergamal-methyl anthranilate schiff base is replaced in the same quantity by any of the following schiff bases, identical results are achieved:

(i) The schiff base of Floralozone and methyl anthranilate of Example II;

(ii) The schiff base of pino acetaldehyde and methyl anthranilate of Example III;

(iii) The schiff base of pino acetaldehyde, hydroxycitronellal and methyl anthranilate in the mole ratio of pino acetaldehyde: hydroxycitronellal:methyl anthranilate of 1:2:3 of Example IV(A);

(iv) The schiff base reaction product of pino acetaldehyde, hydroxycitronella and methyl anthranilate of Example IV with the mole ratio of pino acetaldehyde: hydroxycitronellal:methyl anthranilate being 1:1:2;

(V) The schiff base reaction product of pino acetaldehyde, lilial and methyl anthranilate of Example V(A) with the mole ratio of pino acetaldehyde: lilial:methyl anthranilate being in the mole ratio of 1:2:3.

(vi) The schiff base reaction product of pino acetaldehyde, lilial and methyl anthranilate of Example V(B) with the mole ratio of pino acetaldehyde:lilial: methyl anthranilate being in the mole ratio of 1:1:2;

(vii) The schiff base reaction product of pino acetaldehyde, lyral and methyl anthranilate of Example VI(A) with the mole ratio of pino acetaldehyde:lyral:methyl anthranilate being 1:2:3;

(viii) The schiff base reaction product of pino acetaldehyde, lyral and methyl anthranilate with the mole ratio of pino acetaldehyde:lyral: methyl anthranilate being 1:1:2 of Example VI(B);

(ix) The schiff base reaction product of pino isobutyraldehyde and methyl anthranilate of Example VII;

(x) The schiff base reaction product of melonal and methyl anthranilate of Example VIII;

(xi) The schiff base reaction product of canthoxal and methyl anthranilate of Example IX.

Deodorant detergent products have also been prepared according to Examples I-IX of U.S. Pat. No. 4,304,679 incorporated by reference herein.

Thus, exemplified herein by reference are the following:

(a) a deodorant detergent product comprising:
(i) from 0.5 to 99.99% by weight of a non-soap detergent active compound; and
(ii) from 0.01 up to 10% by weight of a deodorant weight of at least one of the schiff bases or schiff base compositions exemplified by Examples I-IX, supra, said schiff base components having a lipoxidase-inhibiting capacity of at least 50% or a Raoult variance ratio of at least 1.1 as stated in said U.S. Pat. No. 4,304,679, with the schiff base composition having a deodorant value of from 0.5 to 3.5 as measured by the deodorant value test as specifically set forth in said U.S. Pat. No. 4,304,679 and exemplified therein.

Furthermore, the examples of U.S. Pat. No. 4,663,068 are also incorporated herein by reference. Thus, exemplified herein are detergent powder products suitable for the washing of fabrics comprising:

(i) from 5 to 40% by weight of a non-soap detergent active compound comprising an anionic detergent active compound;

(ii) from 1 to 90% of a non-soap detergency builder;

(iii) from 1 to 30% by weight a peroxy bleach compound together with an activator therefor;

(iv) from 0.1 up to 10% by weight of a bleach stable perfume which comprises 50-100% by weight of a bleach stable schiff base component as exemplified by any one of Examples I-IX or mixtures thereof, having a Lipoxidase-inhibiting capacity of at least 50% or a Raoult variance ratio of at least 1.1 as defined according U.S. Pat. No. 4,663,068 incorporated by reference herein, with the schiff base reaction product as defined in any one of Examples I-IX being stable in the presence of sodium perborate tetrahydrate or any other alkali metal perborate tetrahydrate and N,N,N',N'-tetraacetyl ethylenediamine (TEAD) according to the bleach stability test as defined in said U.S. Pat. No. 4,663,068 incorporated by reference herein, the bleach stable deodorant schiff base having a Malodor Reduction Value of from 0.25 up to 3.0 as measured by the Malodor Reduction Value test defined in said U.S. Pat. No. 4,663,068 incorporated by reference herein.

The peroxy bleach activator may be exemplified by the following peroxy bleach activators:

N,N,N',N'-tetracetyl ethylenediamine;
N,N,N',N'-tetracetyl glycoluril;
Glucose pentaacetate;
Sodium acetoxybenzene sulphonate;
Sodium nonanoyloxybenzene sulphonate;
Sodium octanoyloxybenzene sulphonate; and mixtures thereof.

The non-soap anionic detergent active compound may be select from the group consisting of sodium and potassium alkyl sulphates, sodium potassium and ammonium alkyl benzene sulphonates, sodium alkyl glyceryl ether sulphates, sodium coconut oil fatty acids monoglyceride sulphates and sulphonates, sodium and potassium salts of sulphuric acid esters of higher ($C_9$–$C_{18}$) fatty alcohol-alkylene oxide, the reaction products of fatty acids esterified with isethionic acid and neutralized with sodium hydroxide, sodium and potassium salts of fatty acid amides of methyl taurine, alkane monosulphonates, olefin sulphonates and mixtures thereof.

The nonionic detergent active compound may be selected from the group consisting of reaction products of alkylene oxides with alkyl ($C_6$–$C_{22}$) phenols, the condensation products of aliphatic ($C_8$–$C_{18}$) primary or secondary linear or branched alcohols with ethylene oxide, products made by condensation of ethylene oxide with the reaction products of propylene oxide and ethylene diamine, long-chain tertiary amine oxides, long-chain phosphine oxides and dialkyl sulphoxides and mixtures thereof.

What is claimed is:

1. A process for augmenting or enhancing the aroma or taste of a foodstuff or chewing gum comprising the step of intimately admixing with a foodstuff or chewing gum base from 0.2 up to about 50 ppm by weight of a reaction product of methyl anthranilate and bergamal said reaction product being a mixture of compounds having the structures:

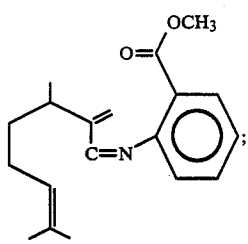
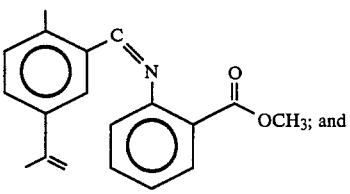
* * * * *